(12) United States Patent
Iwakiri et al.

(10) Patent No.: US 11,221,421 B2
(45) Date of Patent: Jan. 11, 2022

(54) RADIATION DETECTOR, RADIOGRAPHIC IMAGING DEVICE, AND RADIATION DETECTOR MANUFACTURING METHOD

(71) Applicant: FUJIFILM Corporation, Tokyo (JP)

(72) Inventors: Naoto Iwakiri, Kanagawa (JP); Munetaka Kato, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/018,357

(22) Filed: Sep. 11, 2020

(65) Prior Publication Data

US 2020/0408938 A1 Dec. 31, 2020

Related U.S. Application Data

(63) Continuation of application No. PCT/JP2019/009955, filed on Mar. 12, 2019.

(30) Foreign Application Priority Data

| Mar. 19, 2018 | (JP) | JP2018-051692 |
| Nov. 22, 2018 | (JP) | JP2018-219698 |
| Feb. 8, 2019 | (JP) | JP2019-022082 |

(51) Int. Cl.
*H01L 27/146* (2006.01)
*H01L 31/0392* (2006.01)
(Continued)

(52) U.S. Cl.
CPC ............ *G01T 1/20184* (2020.05); *A61B 6/00* (2013.01); *A61B 6/4208* (2013.01); *G01T 1/208* (2013.01);
(Continued)

(58) Field of Classification Search
CPC ....... A61B 6/00; A61B 6/4208; G01T 1/2018; G01T 1/20181; G01T 1/20184;
(Continued)

(56) References Cited

U.S. PATENT DOCUMENTS

| 6,414,315 B1 | 7/2002 | Wei et al. |
| 2006/0038132 A1 | 2/2006 | Hayashida |

(Continued)

FOREIGN PATENT DOCUMENTS

| JP | 2001-188086 A | 7/2001 |
| JP | 2006-058124 A | 3/2006 |

(Continued)

OTHER PUBLICATIONS

The extended European search report issued by the European Patent Office dated Mar. 16, 2021, which corresponds to European Patent Application No. 19772144.2-1001 and is related to U.S. Appl. No. 17/018,357.

(Continued)

*Primary Examiner* — Mark R Gaworecki
(74) *Attorney, Agent, or Firm* — Studebaker & Brackett PC

(57) ABSTRACT

A radiation detector includes a flexible substrate, plural pixels provided on the substrate and each including a photoelectric conversion element, a scintillator stacked on the substrate and including plural columnar crystals, and a bending suppression member configured to suppress bending of the substrate. The bending suppression member has a rigidity that satisfies $R \geq L - r/\tan \Phi + 4r \cdot \{(L - r/\tan \Phi)^2 - (d/2)^2\}^{1/2}/d$, wherein L is an average height of the columnar crystals, r is an average radius of the columnar crystals, d is an average interval between the columnar crystals, Φ is an (Continued)

average tip angle of the columnar crystals, and R is a radius of curvature of bending occurring in the substrate due to the weight of the scintillator.

20 Claims, 29 Drawing Sheets

(51) Int. Cl.
G01T 1/20 (2006.01)
G01T 1/202 (2006.01)
A61B 6/00 (2006.01)
G01T 1/208 (2006.01)

(52) U.S. Cl.
CPC .......... *G01T 1/2018* (2013.01); *G01T 1/2023* (2013.01); *G01T 1/20181* (2020.05); *H01L 27/14663* (2013.01); *H01L 27/14689* (2013.01); *H01L 31/03926* (2013.01)

(58) Field of Classification Search
CPC . G01T 1/2023; G01T 1/208; H01L 27/14663; H01L 27/14689; H01L 31/03926; Y02E 10/50
See application file for complete search history.

(56) References Cited

U.S. PATENT DOCUMENTS

| 2012/0219114 | A1 | 8/2012 | Iwakiri et al. |
|---|---|---|---|
| 2013/0043400 | A1 | 2/2013 | Nakatsugawa et al. |
| 2013/0112884 | A1* | 5/2013 | Osawa .................... G01T 1/202 |
| | | | 250/366 |
| 2013/0264461 | A1 | 10/2013 | Okada et al. |
| 2014/0014843 | A1 | 1/2014 | Ikeda et al. |
| 2014/0027637 | A1 | 1/2014 | Watano |
| 2017/0160405 | A1 | 6/2017 | Kim et al. |

FOREIGN PATENT DOCUMENTS

| JP | 2006058124 A | 3/2006 |
|---|---|---|
| JP | 2011128172 A | 6/2011 |
| JP | 2011-247826 A | 12/2011 |
| JP | 2012132768 A | 7/2012 |
| JP | 2012173275 A | 9/2012 |
| JP | 2012189487 A | 10/2012 |
| JP | 2013-217769 A | 10/2013 |
| JP | 2014-032170 A | 2/2014 |
| JP | 2015-062012 A | 4/2015 |

OTHER PUBLICATIONS

An Office Action; "Notice of Reasons for Refusal," mailed by the Japanese Patent Office dated May 25, 2021, which corresponds to Japanese Patent Application No. 2020-508242 and is related to U.S. Appl. No. 17/018,357 with with English translation.
"A New Dimensionally Stable Polyimide Film XENOMAX"; https://www.nagase.co.jp/display/english/pdf/fpd2014/toyobo.pdf Oct. 29, 2014.
Kazumasa Inoue et al.; "A study of materials Reducing Backscattered Radiations in X-ray for Diagnosis"; The Journal of Japan Academy of Health Sciences; 2004; pp. 218-224; vol. 7; No. 3.
International Search Report issued in PCT/JP2019/009955; dated Apr. 16, 2019.
International Preliminary Report On Patentability and Written Opinion issued in PCT/JP2019/009955; dated Sep. 22, 2020.

* cited by examiner

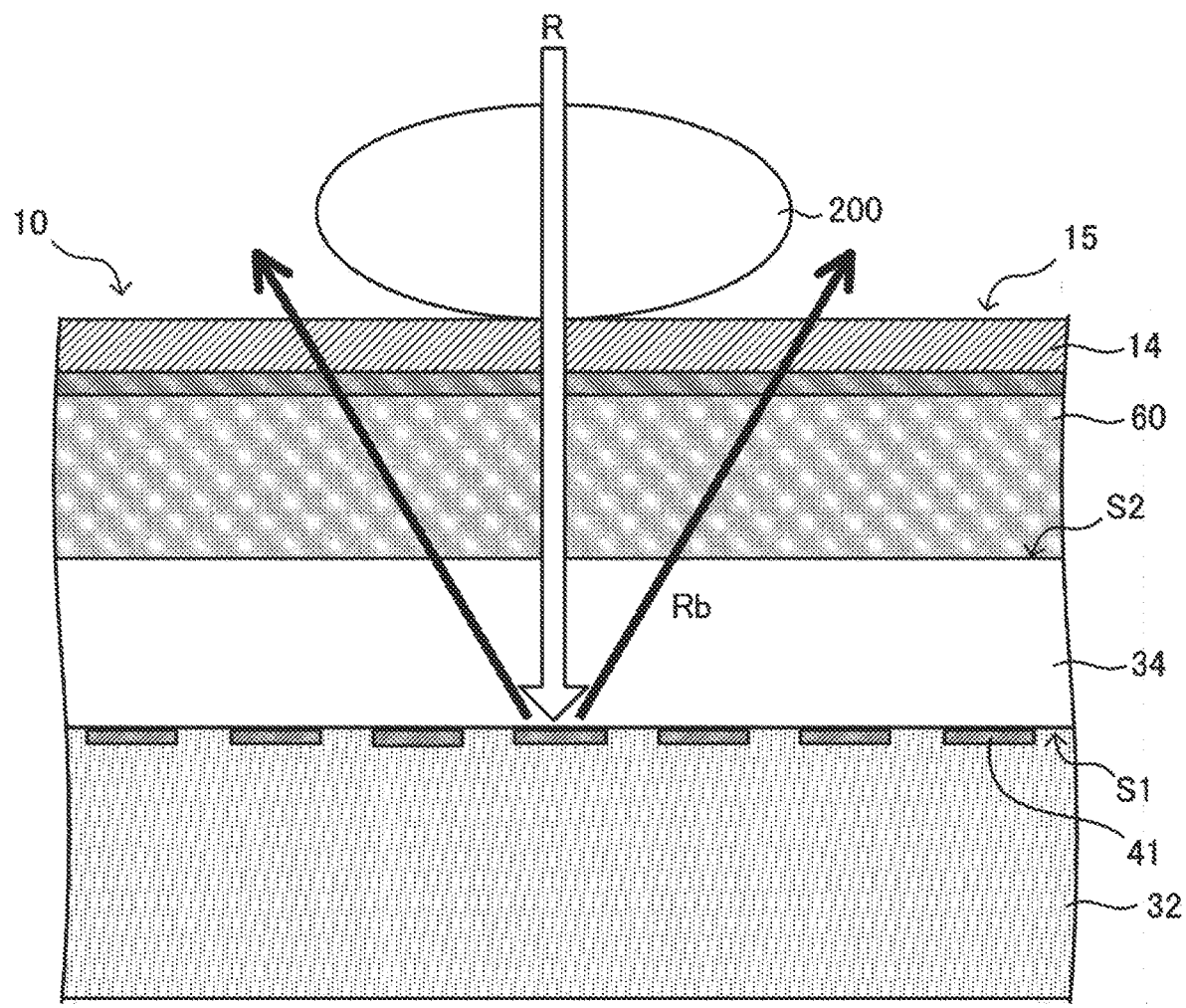

RADIATION DETECTOR, RADIOGRAPHIC IMAGING DEVICE, AND RADIATION DETECTOR MANUFACTURING METHOD

CROSS-REFERENCE TO RELATED APPLICATIONS

This application is a continuation application of International Application No. PCT/JP2019/009955 filed Mar. 12, 2019, the disclosure of which is incorporated herein by reference in its entirety. Further, this application claims priorities from Japanese Patent Application No. 2018-051692, filed Mar. 19, 2018, Japanese Patent Application No. 2018-219698, filed Nov. 22, 2018, and Japanese Patent Application No. 2019-022082, filed Feb. 8, 2019, the disclosures of which are incorporated herein by reference in their entirety.

TECHNICAL FIELD

Technology disclosed herein relates to a radiation detector, a radiographic imaging device, and a method of manufacturing a radiation detector.

RELATED ART

The following technology is an example of known technology related to a radiographic imaging device. Japanese Patent Application Laid-Open (JP-A) No. 2012-173275 (Patent Document 1) describes a radiographic imaging device equipped with a radiographic image detection device body including a scintillator and a light detection section provided at the radiation-incident side of the scintillator, and also equipped with a support member disposed at the radiation-incident side of the radiographic image detection device body to support an imaging subject. The light detection section includes a thin film section to detect fluorescence as an electrical signal, and a reinforcement member provided on the opposite side of the thin film section to the scintillator. The reinforcement member and the support member are joined together so as to cohere along a joining face.

JP-A No. 2012-189487 (Patent Document 2) describes a radiographic imaging device equipped with a scintillator panel including a scintillator and a support substrate to support the scintillator, a sensor panel including a light sensor configured to detect light converted by the scintillator and a sensor substrate provided with the light sensor, the sensor panel being stuck to the scintillator by a first bonding layer, and a reinforcing plate stuck to the support substrate by a second bonding layer.

JP-A No. 2012-132768 (Patent Document 3) describes a radiation detector panel equipped with a case, a scintillator housed inside the case, and a light detection section disposed on a light-emitting side of the scintillator inside the case. The case is provided with a top plate that bends under load at a surface exposed to radiation. The scintillator includes plural upright columnar crystals, and the scintillator distorts with bending of the top plate. In a plane in which the columnar crystals are provided, gaps between the columnar crystals provided at a peripheral edge portion are wider than gaps between the columnar crystals provided at a central portion.

A known radiation detector employed in a radiographic imaging device includes a substrate, plural pixels provided on a front surface of the substrate, each of the pixels including a photoelectric conversion element, and a scintillator stacked on the substrate. In recent years flexible materials such as resin films are being employed as radiation detector substrate materials. In cases in which the substrate is flexible, for example, a concern arises that comparatively large localized bending of the substrate might occur due to the weight of the scintillator stacked on the substrate when the substrate is handled during processes to manufacture the radiation detector. In cases in which the scintillator includes plural columnar crystals, there is a concern that the scintillator might sustain damage due to mutually adjacent columnar crystals to contacting each other were significant bending of the substrate to occur.

SUMMARY

An object of an aspect of technology disclosed herein is to reduce the risk of damage to a scintillator caused by a substrate bending due to the weight of the scintillator compared to cases lacking a bending suppression member having a rigidity prescribed according to the height, radius, and tip angle of columnar crystals configuring a scintillator as well as an interval between the columnar crystals.

A radiation detector according to a first aspect of technology disclosed herein includes a flexible substrate, plural pixels provided on the substrate and each including a photoelectric conversion element, a scintillator stacked on the substrate and including plural columnar crystals, and a bending suppression member configured to suppress bending of the substrate. The bending suppression member has a rigidity that satisfies $R \geq L - r/\tan \Phi + 4r \times \{(L - r/\tan \Phi)^2 - (d/2)^2\}^{1/2}/d$, wherein L is an average height of the columnar crystals, r is an average radius of the columnar crystals, d is an average interval between the columnar crystals, $\Phi$ is an average tip angle of the columnar crystals, and R is a radius of curvature of bending occurring in the substrate due to the weight of the scintillator

BRIEF DESCRIPTION OF DRAWINGS

FIG. 11B is a cross-section illustrating back scattering radiation generated inside a substrate lacking a fine particle layer.

DETAILED DESCRIPTION

Figure 1:
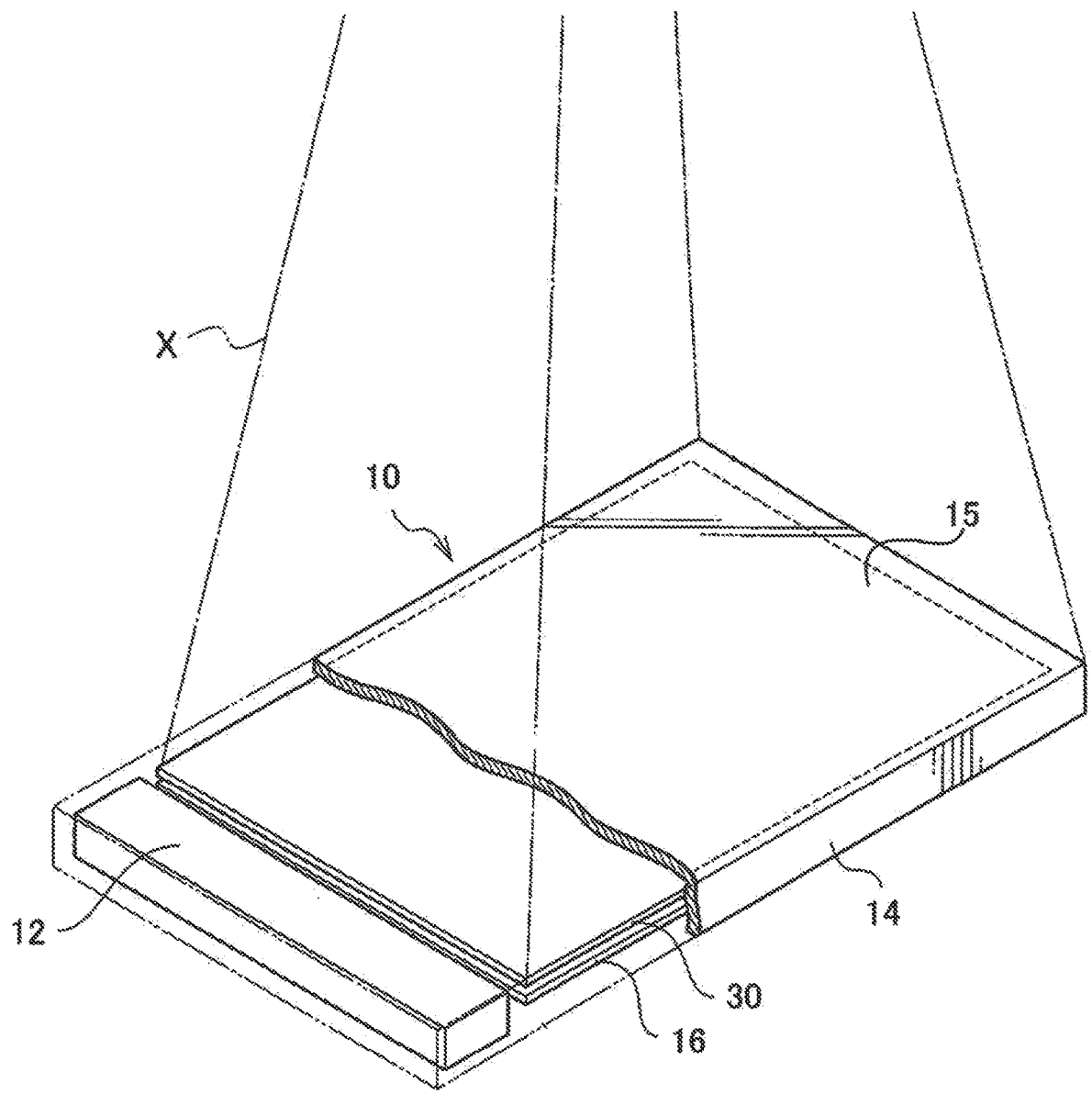
FIG. 1 is a perspective view illustrating an example of a configuration of a radiographic imaging device according to an exemplary embodiment of technology disclosed herein.

Explanation follows regarding examples of exemplary embodiments of technology disclosed herein, with reference to the drawings. Note that the same or equivalent configuration elements and portions are allocated the same reference numerals in each of the drawings.

First Exemplary Embodiment

FIG. 1 is a perspective view illustrating an example of configuration of a radiographic imaging device 10 according to an exemplary embodiment of technology disclosed herein. The radiographic imaging device 10 employs a portable electronic cassette format. The radiographic imaging device 10 is configured including a radiation detector 30 (flat panel detector (FPD)), a control unit 12, a support plate 16, and a case 14 housing the radiation detector 30, the control unit 12, and the support plate 16.

The case 14 has, for example, a monocoque structure configured from carbon fiber reinforced plastic, which X-ray radiation and the like readily permeates, and is lightweight and highly durable. Radiation emitted from a radiation source (not illustrated in the drawings) and transmitted through an imaging subject (not illustrated in the drawings) is incident to a radiation-incident face 15 configuring an upper face of the case 14. Inside the case 14, the radiation detector 30 and the support plate 16 are arranged in this sequence from the radiation-incident face 15 side.

The support plate 16 is fixed to the case 14, and supports a circuit board 19 (see FIG. 2) to which is mounted an integrated circuit (IC) chip for performing signal processing and the like. The control unit 12 is arranged at an end portion inside the case 14. The control unit 12 is configured including a battery (not illustrated in the drawings) and a controller 29 (see FIG. 3).

Figure 2:
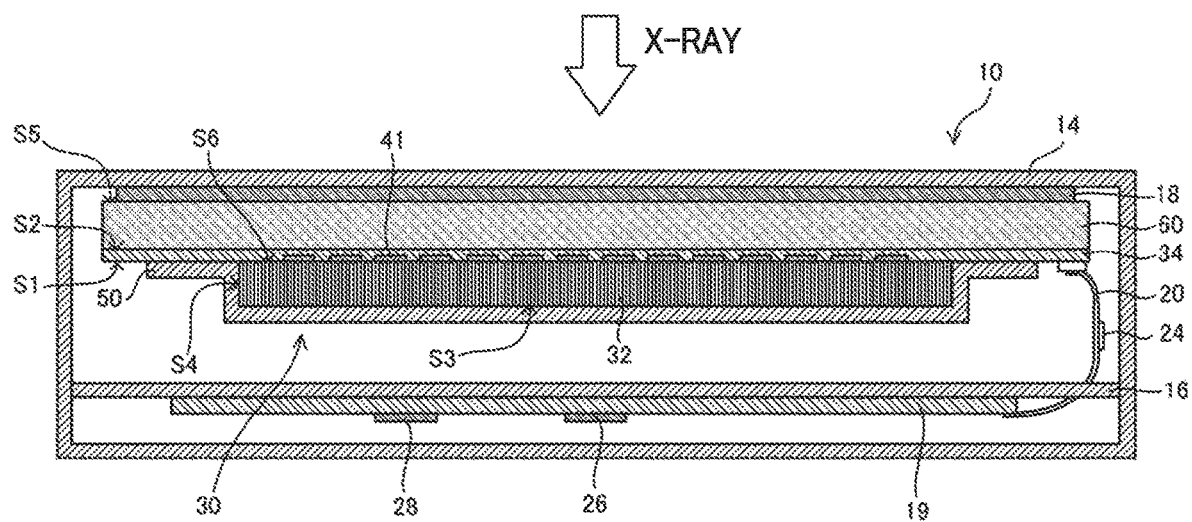
FIG. 2 is a cross-section illustrating an example of a configuration of a radiographic imaging device according to an exemplary embodiment of technology disclosed herein.

FIG. 2 is a cross-section illustrating an example of a configuration of the radiographic imaging device 10. The radiation detector 30 includes a flexible substrate 34, plural pixels 41 that are provided on a front surface of the substrate 34 and that each include a photoelectric conversion element 36 (see FIG. 3), and a scintillator 32 and a bending suppression member 60 to suppress bending of the substrate 34, both stacked on the substrate 34.

The substrate 34 is a flexible substrate that is capable of bending. In the present specification, reference to the substrate 34 being flexible means that when the rectangular substrate 34 is fixed at one side out of its four sides, then due to the weight of the substrate 34, a height at a position 10 cm away from the fixed side of the substrate 34 will be at least 2 mm lower than the height of the fixed side. For example, a resin substrate, a metal foil substrate, or a thin glass sheet having a thickness of about 0.1 mm may be employed as the material of the substrate 34. A resin film such as XENOMAX (registered trademark) or the like that is a highly heat-resistant polyimide film is particularly preferably employed therefor. Employing a resin film as the material of the substrate 34 enables a reduction in weight and a reduction in cost of the radiation detector 30 to be achieved compared to cases in which a glass substrate is employed as the material of the substrate 34, and furthermore, the risk of impact damage to the substrate 34 can also be reduced. The plural pixels 41 are respectively provided on a first surface S1 of the substrate 34.

The thickness of the substrate 34 depends on the hardness, size, and the like of the substrate 34, and may be any thickness that enables the desired flexibility to be achieved. In cases in which the substrate 34 is configured including a base member made from a resin material, the thickness of the substrate 34 is, for example, preferably from 5 µm to 125 µm, and is more preferably from 20 µm to 50 µm.

Note that the coefficient of thermal expansion (CTE) of the substrate 34 in a temperature range of from 300° C. to 400° C. is preferably approximately the same as the coefficient of thermal expansion of the material configuring the photoelectric conversion element 36 (amorphous silicon, for example) (±approximately 5 ppm/K), and specifically is preferably not more than 20 ppm/K. Moreover, a heat shrinkage ratio in a machine direction (MD) of the substrate 34 at 400° C. and at a thickness of 25 µm is preferably not more than 0.5%. Moreover, the substrate 34 preferably does not have a transition point in a temperature range of from 300° C. to 400° C., as is typical of an ordinary polyimide, and preferably has a modulus of elasticity at 500° C. of not less than 1 GPa. The substrate 34 with the above characteristics is able to withstand thermal processing when forming the pixels 41 on the substrate 34, and enables the pixels 41 to be formed on the substrate 34 in an appropriate manner.

Figure 10:
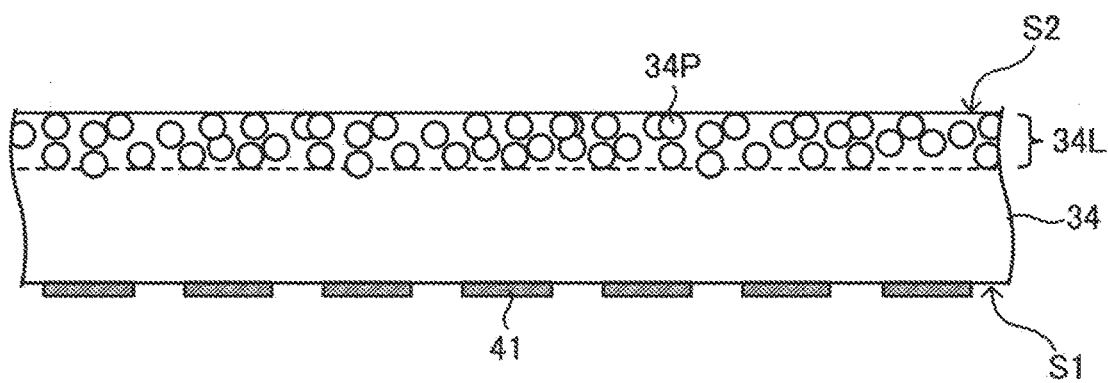
FIG. 10 is cross-section illustrating an example of a configuration of a substrate according to an exemplary embodiment of technology disclosed herein.

Moreover, in cases in which the substrate 34 is configured including abase member formed from a resin material such as a polyimide or the like, as illustrated in FIG. 10, the base member made from the resin material preferably includes a fine particle layer 34L containing plural fine particles 34P made from an inorganic material and having a mean particle size of from 0.05 µm to 2.5 µm. Moreover, the fine particle layer 34L is preferably provided on a second surface S2 of the substrate 34, this being on the opposite side of the substrate 34 to the first surface S1 provided with the pixels 41. Namely, the fine particles 34P are preferably present more toward the second surface S2 side of the substrate 34. The fine particles 34P may sometimes cause indentations and protrusions on the front surface of the substrate 34, making it difficult to form the pixels 41 on the front surface of the fine particle layer 34L. Arranging the fine particle layer 34L on the second surface S2 side of the substrate 34 enables the flatness of the first surface S1 to be secured, making it easier to form the pixels 41.

The material of the fine particles 34P is preferably an inorganic material including an element having an atomic number that is greater than the atomic number of each element configuring the base member of the substrate 34, but that is not more than 30. For example, in cases in which the base member of the substrate 34 is configured from a resin material such as an polyimide or the like including C, H, O, and N, the fine particles 34P are preferably configured of an inorganic material including an element that has an atomic number greater than the atomic numbers of the elements configuring the resin material (i.e. C, H, O, and N) but that is not more than 30. Specific examples of such fine particles 34P include $SiO_2$ that is an oxide of silicon of atomic number 14, MgO that is an oxide of Mg of atomic number 12, $Al_2O_3$ that is an oxide of Al of atomic number 13, and $TiO_2$ that is an oxide of Ti of atomic number 22. XENOMAX (registered trademark) is a specific example of a resin sheet having the characteristics listed above and containing a fine particle layer 34L.

Note that the above thicknesses in the present exemplary embodiment are measured using a micrometer. The coefficient of thermal expansion is measured according to JIS K7197:1991. In this measurement, test pieces are cut from a main face of the substrate 34 while changing the angle thereof by 15 degrees each time, the coefficient of thermal expansion is measured for each of the cut test pieces, and the highest value obtained is taken to be the coefficient of thermal expansion of the substrate 34. The measurements of the coefficient of thermal expansion in the machine direction (MD) and the transverse direction (TD) are performed at 10° C. intervals over a range of from −50° C. to 450° C. with ppm/° C. converted into ppm/K. A TMA4000S instrument made by MAC Science Co., Ltd. is employed to measure the coefficient of thermal expansion using a sample length of 10 mm, a sample width of 2 mm, an initial load of 34.5 g/mm$^2$, a speed of temperature increase of 5° C./min, and an argon atmosphere. The modulus of elasticity is measured according to K7171:2016. Note that in this measurement, test pieces are cut from a main face of the substrate 34 while changing the angle thereof by 15 degrees each time, a stretch test is performed on each of the cut test pieces, and the highest value obtained is taken to be the modulus of elasticity of the substrate 34.

The scintillator 32 is stacked on the first surface S1 side of the substrate 34. The scintillator 32 contains phosphors for converting irradiated radiation into light. The scintillator 32 is configured, for example, by an aggregation of columnar crystals including thallium-doped caesium iodide (CsI:Tl). The columnar crystals of CsI:Tl can be directly formed on the substrate 34 using, for example, a vapor phase epitaxial method. Forming the columnar crystals using a vapor phase epitaxial method enables stable formation of the columnar crystals. Note that the columnar crystals of CsI:Tl may be formed on a separate substrate from the substrate 34, and then stuck to the substrate 34. Each of the respective photoelectric conversion elements 36 (see FIG. 3) configuring the plural pixels 41 generates an electrical charge based on the light emitted from the scintillator 32.

A surface S3 of the scintillator 32 on the opposite side to a surface S6 that contacts the substrate 34, and a surface S4 of the scintillator 32 that intersects with the surface S3, are covered by a reflective film 50. The reflective film 50 has a function to reflect light generated in the scintillator 32 toward the substrate 34 side. Al$_2$O$_3$ may, for example, be employed as the material of the reflective film 50. The reflective film 50 covers the surface S3 and the surface S4 of the scintillator 32, and also covers the substrate 34 at portions in the vicinity of the scintillator 32. Note that the reflective film 50 may be omitted in cases in which a radiographic image of the desired quality can be obtained with the radiographic imaging device 10 without providing the reflective film 50.

In the present exemplary embodiment, the substrate 34 is arranged at the radiation-incident side and the radiographic imaging device 10 employs an irradiation side sampling (ISS) imaging method. Adopting the irradiation side sampling method enables the distance been positions of intense light emission in the scintillator 32 and the pixels 41 to be shortened compared to when employing a penetration side sampling (PSS) method, in which the scintillator 32 is arranged at the radiation-incident side. This thereby enables radiographic images to be obtained with higher resolution. Note that the radiographic imaging device 10 may employ penetration side sampling.

The support plate 16 is arranged at the opposite side of the scintillator 32 to the radiation-incident side. A gap is provided between the support plate 16 and the scintillator 32. The support plate 16 is fixed to side portions of the case 14.

The circuit board 19 is provided on the surface of the support plate 16 on the opposite side to the scintillator 32. The circuit board 19 is mounted with a signal processor 26 for generating image data, an image memory 28 for storing the image data generated by the signal processor 26, and the like.

The circuit board 19 and the substrate 34 are electrically connected together through a flexible cable 20 printed on a flexible printed circuit (FPC) and a tape carrier package (TCP) or a chip-on-film (COF). Charging amplifiers 24 for converting electrical charge read from the pixels 41 into electrical signals are mounted on the cable 20. A gate line driver 22 (see FIG. 3) that is electrically connected to the circuit board 19 and the substrate 34 is mounted to a separate flexible printed circuit not illustrated in FIG. 2.

The bending suppression member 60 is stacked on the second surface S2 side of the substrate 34 on the opposite side to the first surface S1. The bending suppression member 60 has the role of imparting the substrate 34 with the necessary rigidity for the substrate 34 to support the scintillator 32. Namely, providing the bending suppression member 60 suppresses the substrate 34 from bending due to the weight of the scintillator 32 compared to cases in which the bending suppression member 60 is omitted. The bending suppression member 60 extends over a wider range than an extension range of the scintillator 32. Namely, a surface area of the bending suppression member 60 is larger than a surface area of the scintillator 32 in plan view, and the scintillator 32 is arranged at the inside of the extension range of the bending suppression member 60. Thus, planar direction end portions of the bending suppression member 60 are positioned to the outside of planar direction end portions of the scintillator 32. This enhances the effect of suppressing the substrate 34 from bending due to the weight of the scintillator 32. The substrate 34 includes a connection region 80 where the flexible cable 20 is connected to an outer peripheral portion of the substrate 34. The bending suppression member 60 is provided in a region covering at least a portion of the connection region 80 and also covering the scintillator 32. Since the substrate 34 has a tendency to bend even in the connection region 80 where the cable 20 is connected, providing the bending suppression member 60 in the region covering at least a portion of the connection region 80 enables bending in the connection region 80 of the substrate 34 to be suppressed.

The bending suppression member 60 preferably has a higher rigidity than that of the substrate 34 from the perspective of being able to suppress bending of the substrate 34. The bending suppression member 60 is preferably a member employing a material having a bending elastic modulus from 1000 MPa to 3500 MPa. By configuring the bending suppression member 60 from a material having a bending elastic modulus of 1000 MPa or greater, functionality is effectively exhibited by the bending suppression member 60 to suppress bending of the substrate 34. Configuring the bending suppression member 60 from a material having a bending elastic modulus of 3500 MPa or lower means that, for example, after the bending suppression member 60 has been attached to the substrate 34 in a manufacturing process of the radiation detector 30, when detaching a support body (not illustrated in the drawings) supporting the substrate 34 from the substrate, the support body can be easily detached from the substrate 34 by appropriately bending the substrate 34. Note that the method employed to measure the bending elastic modulus may be the measurement method defined in JIS K 7171:2016. Moreover, the bending rigidity of the bending suppression member 60 is preferably from 3600 Pa·cm$^4$ to 196000 Pa·cm$^4$.

The thickness of the bending suppression member 60 is preferably approximately 0.1 mm.

The coefficient of thermal expansion of the bending suppression member 60 is preferably from 30 ppm/K to 80 ppm/K. Moreover, the coefficient of thermal expansion of the bending suppression member 60 is preferably close to the coefficient of thermal expansion of the scintillator 32. Specifically, a ratio of the coefficient of thermal expansion C2 of the bending suppression member 60 against the coefficient of thermal expansion C1 of the scintillator 32 (C2/C1) is preferably from 0.5 to 2. Making the coefficient of thermal expansion of the bending suppression member 60 satisfy the conditions listed above enables the risk of the substrate 34 and the scintillator 32 detaching from each other, such as when heating or when heat is generated, to be suppressed. For example, the coefficient of thermal expansion of the scintillator 32 is 50 ppm/K in cases in which the scintillator 32 is configured mainly from CsI:Tl. In such cases, the following materials may be employed as the material of the bending suppression member 60: polyvinyl chloride (PVC) having a coefficient of thermal expansion of from 60 ppm/K to 80 ppm/K, acrylic having a coefficient of thermal expansion of from 70 ppm/K to 80 ppm/K, polyethylene terephthalate (PET) having a coefficient of thermal expansion of from 65 ppm/K to 70 ppm/K, polycarbonate (PC) having a coefficient of thermal expansion of 65 ppm/K, TEFLON (registered trademark) having a coefficient of thermal expansion of from 45 ppm/K to 70 ppm/K, or the like. In consideration of the above bending elastic modulus, the material of the bending suppression member 60 preferably is a material including at least one out of acrylic, PET, or PC.

Other candidate materials that may be employed for the bending suppression member 60 include, for example, resins of polyphenylene sulfide (PPS), polyarylate (PAR), polysulfone (PSF), polyether sulfone (PES), polyetherimide (PEI), polyamide-imide (PAI), polyether ether ketone (PEEK), phenol resin, polytetrafluoroethylene, polychlorotrifluoroethylene, silicone resin, polyethylene naphthalate (PEN), and the like. A metal such as aluminum, iron, or an alloy thereof may also be employed as the material of the bending suppression member 60. A layered body configured by stacking layers of resin and metal may also be employed as the material of the bending suppression member 60. The surface S5 of the bending suppression member 60 on the opposite side to the face contacting the substrate 34 is stuck to an inner wall of the case 14 with a bonding layer 18 interposed therebetween.

Figure 3:
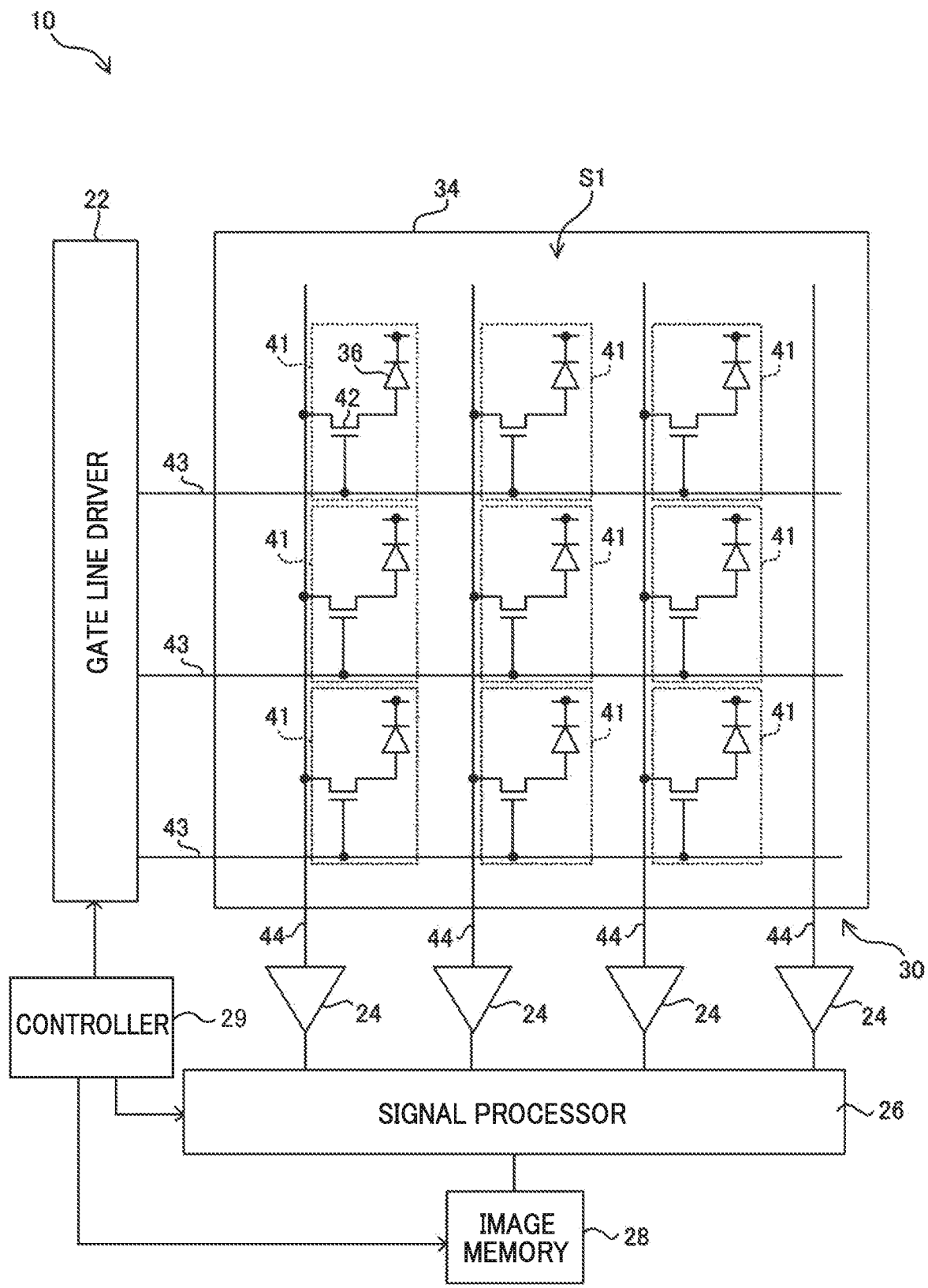
FIG. 3 is a diagram illustrating an example of an electrical configuration of a radiographic imaging device according to an exemplary embodiment of technology disclosed herein.

FIG. 3 is a diagram illustrating an example of an electrical configuration of the radiographic imaging device 10. Plural pixels 41 are arranged in a matrix formation on the first surface S1 of the substrate 34. Each of the pixels 41 includes a photoelectric conversion element 36 and a thin film transistor (TFT) 42. The photoelectric conversion element 36 generates electrical charge according to the light emitted from the scintillator 32. The TFT 42 serves as a switching element that is switched to an ON state in order to read the electrical charge generated in the photoelectric conversion element 36. The photoelectric conversion element 36 may, for example, be a photodiode configured from amorphous silicon.

Gate lines 43 and signal lines 44 are provided on the first surface S1 of the substrate 34. The gate lines 43 extend in one direction (a row direction) that the pixels 41 are arrayed along. The signal lines 44 extend in a direction (a column direction) intersecting with the extension direction of the gate lines 43. The pixels 41 are provided so as to correspond to the respective intersection portions between the gate lines 43 and the signal lines 44.

Each of the gate lines 43 is connected to the gate line driver 22. The gate line driver 22 performs reading of the electrical charge accumulated in the pixels 41 in response to a control signal supplied from the controller 29. Each of the signal lines 44 is connected to a charging amplifier 24. The charging amplifiers 24 are provided corresponding to each of the plural signal lines 44. The charging amplifiers 24 generate electrical signals based on the electrical charge read from the pixels 41. The output terminals of the charging amplifiers 24 are connected to the signal processor 26. Based on the control signals supplied from the controller 29, the signal processor 26 generates image data by performing specific processing on the electrical signals supplied from the charging amplifiers 24. The image memory 28 is connected to the signal processor 26. The image memory 28 stores the image data generated by the signal processor 26 based on the control signals supplied from the controller 29.

The controller 29 has a wired or wireless connection to a radiation source via a communication section (not illustrated in the drawings), performs communication with a console (not illustrated in the drawings), and controls operation of the radiographic imaging device 10 by controlling the gate line driver 22, the signal processor 26, and the image memory 28. The controller 29 may have a configuration including, for example, a microcomputer. Note that the gate line driver 22 is an example of a reading section of technology disclosed herein. The signal processor 26 is an example of a generation section of technology disclosed herein.

Explanation follows regarding an example of operation of the radiographic imaging device 10. When radiation emitted from the radiation source (not illustrated in the drawings) and transmitted through an imaging subject is incident through the radiation-incident face 15 of the radiographic imaging device 10, the scintillator 32 absorbs the radiation and emits visible light. The photoelectric conversion elements 36 configuring the respective pixels 41 convert the light emitted from the scintillator 32 into electrical charge. The electrical charge generated by each of the photoelectric conversion elements 36 is accumulated in the corresponding pixel 41. The amount of electrical charge generated by the photoelectric conversion element 36 is reflected in a pixel value of the corresponding pixel 41.

In order to generate a radiographic image, the gate line driver 22 supplies a gate signal to the TFTs 42 through gate lines 43 based on a control signal supplied from the controller 29. The TFTs 42 are switched to the ON state by the gate signal in row units. Due to the TFTs 42 being switched to the ON state, the electrical charge accumulated in each of the pixels 41 is read through the corresponding signal line 44, and is supplied to the corresponding charging amplifier 24. The charging amplifiers 24 generate electrical signals based on the electrical charges read from the signal lines 44 and supply the generated electrical signals to the signal processor 26.

The signal processor 26 is equipped with plural sample-and-hold circuits, a multiplexer, and an analogue-to-digital converter (none of which are illustrated in the drawings). The plural sample-and-hold circuits are provided so as to correspond to each of the respective plural signal lines 44. The electrical signals supplied from the charging amplifiers 24 are held in the sample-and-hold circuits. The electrical signals held in the individual sample-and-hold circuits are each input to the analogue-to-digital converter through the multiplexer to be converted into digital signals. The signal processor 26 generates, as image data, data in which the digital signals generated by the analogue-to-digital converter are associated with information about the positions of the respective pixels 41, and supplies this image data to the image memory 28. The image memory 28 stores the image data generated by the signal processor 26.

Due to the flexibility of the substrate 34, there is a concern that comparatively large localized bending might occur in the substrate 34 due to the weight of the scintillator 32 when, for example, the substrate 34 is handled during processes to manufacture the radiation detector 30. In cases in which the scintillator 32 includes plural columnar crystals, there is a concern that the scintillator 32 might sustain damage due to mutually adjacent columnar crystals contacting each other were significant bending of the substrate 34 to occur.

Figure 4:
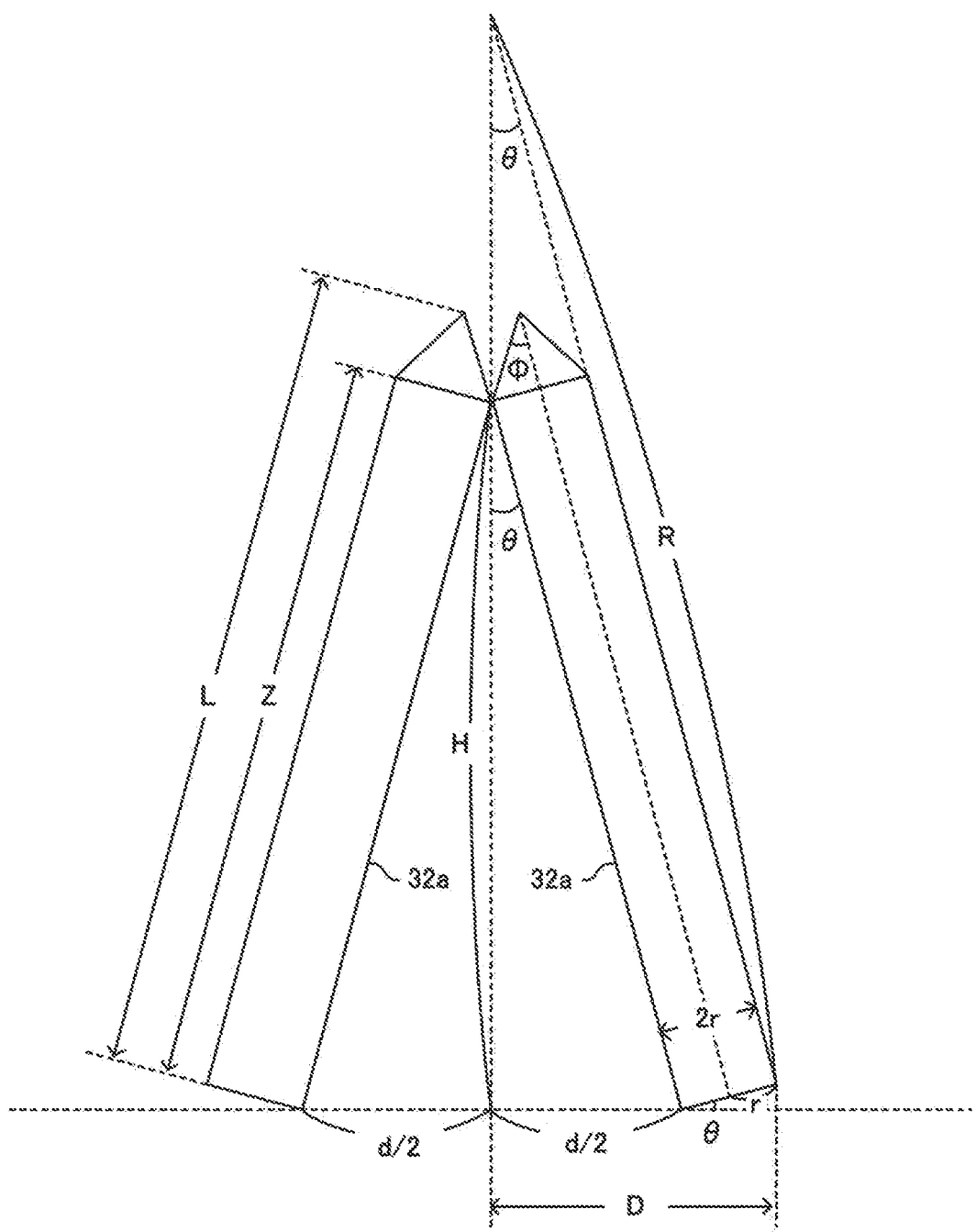
FIG. 4 is a diagram illustrating a state in which a substrate has been bent into a circular arc shape such that two mutually adjacent columnar crystals contact each other.

FIG. 4 is a diagram illustrating a state in which the substrate 34 has been bent into a circular arc shape such that two mutually adjacent columnar crystals 32*a* configuring the scintillator 32 contact each other. In FIG. 4, R is the radius of curvature of the bending of the substrate 34, and L is the average height of the columnar crystals 32*a* (also referred to as the average height L). Z is the average height of the columnar crystals 32*a* not including tips thereof. r is the average radius of the columnar crystals 32*a* (also referred to as the average radius r), $\Phi$ is the average angle of the tips of the columnar crystals 32*a* (also referred to as the average angle $\Phi$, and d is the average interval between mutually adjacent columnar crystals 32*a* (also referred to as the average interval d). $\theta$ is the slope angle of a columnar crystal 32*a* as a result of the bending of the substrate 34.

Since the interval d between the columnar crystals 32*a* corresponds to the length of the chord of a segment with a radius Z and a center angle of 2$\theta$, Equation (1) below can be derived, and Equation (2) can be derived from Equation (1).

$$d = 2Z \times \sin \theta \quad (1)$$

$$\sin \theta = d/2Z \quad (2)$$

Equation (3) below is established for the length D in FIG. 4.

$$D = d/2 + 2r \times \cos \theta = R \times \sin \theta \quad (3)$$

According to the Pythagoras theorem, Equation (4) below is established for the length h in FIG. 4.

$$h = \{Z^2 - (d/2)^2\}^{1/2} \quad (4)$$

Equation (5) below is established for cos $\theta$.

$$\cos \theta = h/Z = \{Z^2 - (d/2)^2\}^{1/2}/Z \quad (5)$$

Substituting Equation (3) in Equation (2) and Equation (5) enables Equation (6) below to be derived.

$$d/2 + 2r \times \{Z^2 - (d/2)^2\}^{1/2}/Z = R \times d/2Z \quad (6)$$

Equation (7) is obtained by solving Equation (6) for the radius of curvature R.

$$R = Z + 4r \times \{Z^2 - (d/2)^2\}^{1/2}/d \quad (7)$$

Equation (8) below is established for Z. Equation (9) is obtained by substituting Equation (7) in Equation (8).

$$Z = L - r/\tan \Phi \quad (8)$$

$$R = L - r/\tan(+4r \times \{(L - r/\tan \Phi)^2 - (d/2)^2\}^{1/2}/d \quad (9)$$

According to Equation (9), there is a high possibility that mutually adjacent columnar crystals 32*a* will contact each other if the radius of curvature R of bending occurring in the substrate 34 satisfies Equation (9). Accordingly, limiting the radius of curvature R to the range defined by Equation (10) enables the risk of damage to the scintillator 32 as a result of the columnar crystals 32*a* contacting each other due to bending of the substrate 34 to be reduced in comparison to cases in which Equation (10) is not satisfied.

$$R \geq L - r/\tan \Phi + 4r \times \{(L - r/\tan \Phi)^2 - (d/2)^2\}^{1/2}/d \quad (10)$$

For example, in a case in which the average radius r of the columnar crystals 32*a* is 5 µm, the average height L of the columnar crystals 32*a* is 500 µm, the average angle $\Phi$ of the tips of the columnar crystals 32*a* is 30°, and the average interval d between mutually adjacent columnar crystals 32*a* is no greater than 1 µm, then setting the radius of curvature R of bending of the substrate 34 to at least 10.318 mm enables the risk of damage to the scintillator 32 to be reduced. Since localized bending also presents a risk of damage, the use of a member capable of suppressing localized bending by preventing creases due to nicking or the like is also required.

In the radiation detector 30 according to the present exemplary embodiment, the rigidity of the bending suppression member 60 is set such that, in a fixed state to end portions of the substrate 34, the radius of curvature R of bending that occurs in the substrate 34 due to the weight of the scintillator 32 satisfies Equation (10). In other words, the rigidity of the bending suppression member 60 is adjusted such that, in a fixed state to end portions of the substrate 34, the radius of curvature R of the bending that occurs in the substrate 34 due to the weight of the scintillator 32 satisfies Equation (10). Namely, the rigidity of the bending suppression member 60 is prescribed according to the height, radius, and tip angle of the columnar crystals 32*a* configuring the scintillator 32, and also the interval between the columnar crystals 32*a*. Adopting this approach enables the risk of the scintillator 32 being damaged by bending of the substrate 34 due to the weight of the scintillator 32 when, for example, the substrate 34 is handled during processes to manufacture the radiation detector 30, to be reduced in comparison to cases in which Equation (10) is not satisfied. For example, since the permitted radius of curvature R becomes larger the greater the height L of the columnar crystals 32*a*, the higher the rigidity of the bending suppression member 60 employed.

The rigidity of the bending suppression member 60 may, for example, be adjusted using the thickness, density, elastic modulus, or the like of the bending suppression member 60. Moreover, the rigidity of the bending suppression member 60 may also be adjusted by the selection of the material configuring the bending suppression member 60.

Explanation follows regarding a method of manufacturing the radiation detector 30. FIG. 5A to FIG. 5D are cross-sections illustrating an example of a method of manufacturing the radiation detector 30.

Figure 5A:
FIG. 5A is a cross-section illustrating an example of a manufacturing method of a radiation detector according to an exemplary embodiment of technology disclosed herein.

Firstly, the plural pixels 41 are formed on the first surface S1 of the substrate 34 (FIG. 5A). Note that formation of the pixels 41 may be performed in a state in which the substrate 34 is supported by a support body (not illustrated in the drawings) to support the substrate 34.

Figure 5B:
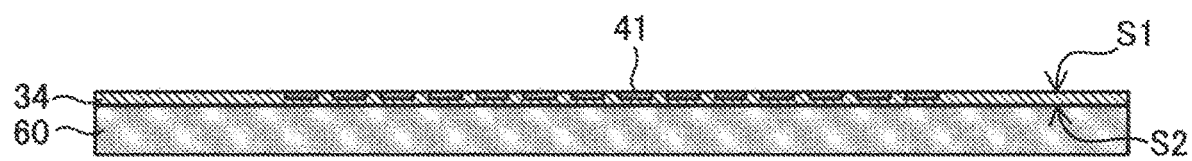
FIG. 5B a cross-section illustrating an example of a manufacturing method of a radiation detector according to an exemplary embodiment of technology disclosed herein.

Next, the bending suppression member 60 is stuck to the second surface S2 of the substrate 34 on the opposite side to the first surface S1 of the substrate 34 (FIG. 5B). The bending suppression member 60 has a rigidity such that the radius of curvature R of bending that occurs in the substrate 34 due to the weight of the scintillator 32 satisfies Equation (10). Namely, the rigidity of the bending suppression member 60 is adjusted according to the average height L of the columnar crystals 32*a*, the average radius r of the columnar crystals 32a, the average interval d between the columnar crystals 32a, and the average angle Φ of the tips of the columnar crystals 32a. For example, the rigidity of the bending suppression member 60 is set higher the greater the average height L of the columnar crystals 32a.

Figure 5C:
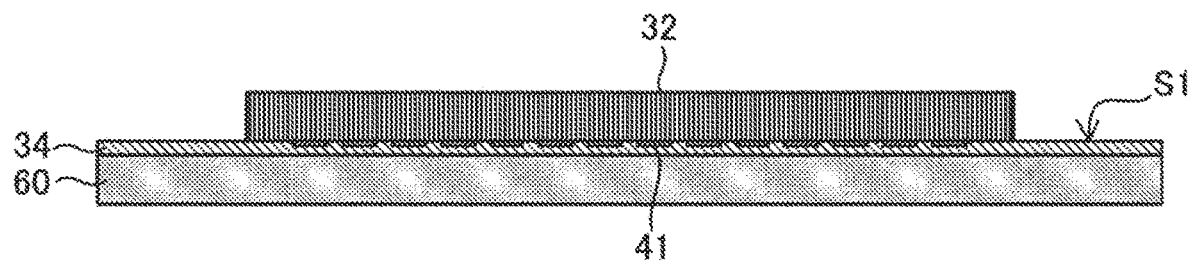
FIG. 5C is a cross-section illustrating an example of a manufacturing method of a radiation detector according to an exemplary embodiment of technology disclosed herein.

Next, the scintillator 32 is formed on the first surface S1 of the substrate 34 (FIG. 5C). The scintillator 32 may be formed using, for example, a vapor phase epitaxial method, so as to directly grow columnar crystals of Tl-doped CsI on the substrate 34.

Figure 6:
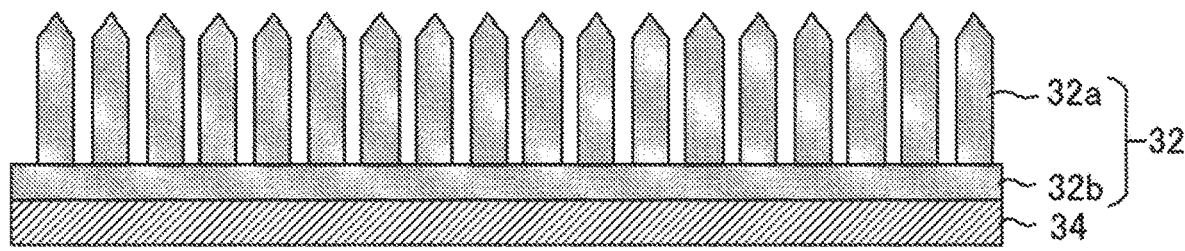
FIG. 6 is a cross-section illustrating columnar crystals formed on a substrate according to an exemplary embodiment of technology disclosed herein.

FIG. 6 is a cross-section illustrating the columnar crystals 32a formed on the substrate 34. In a vapor phase epitaxial method to form the columnar crystals 32a of CsI on the substrate 34 directly, a non-columnar portion 32b not configured by columnar crystals is formed on the substrate 34 in an initial growth stage, and the columnar crystals 32a are then formed on a foundation of the non-columnar portion 32b. In such cases, the non-columnar portion 32b is in contact with the substrate 34 and the tips of the columnar crystals 32a are disposed on a front surface side of the scintillator 32. Note that columnar crystals of CsI:Tl may be formed on a separate substrate to the substrate 34 and then stuck to the substrate 34. When employing such a method, the tips of the columnar crystals 32a contact the substrate 34 and the non-columnar portion 32b is on the front surface side of the scintillator 32. In cases in which the tips of the columnar crystals 32a are on the front surface side of the scintillator 32, the columnar crystals 32a are more susceptible to contacting each other due to bending of the substrate 34 than in cases in which the non-columnar portion 32b is on the front surface side of the scintillator 32. The technology disclosed herein is therefore particularly effective when the former case is applied.

Figure 5D:
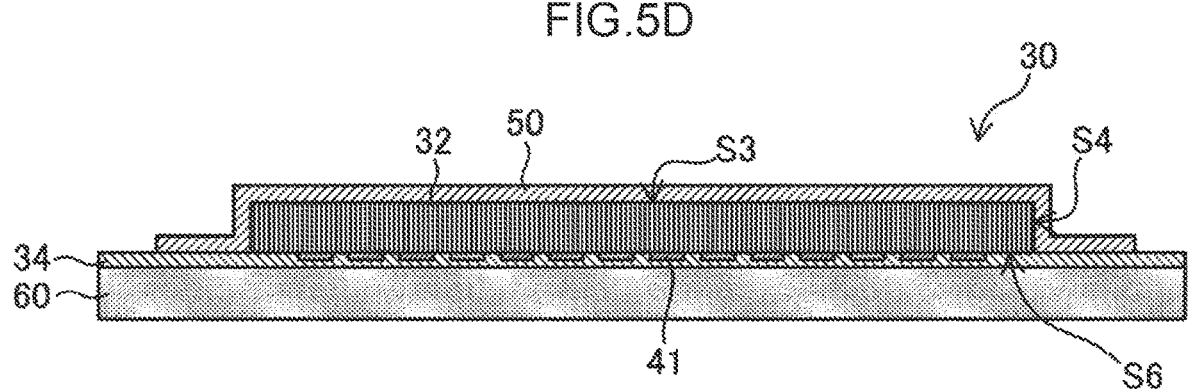
FIG. 5D is a cross-section illustrating an example of a manufacturing method of a radiation detector according to an exemplary embodiment of technology disclosed herein.

After forming the scintillator 32 on the substrate 34, the reflective film 50 is then formed so as to cover the surface S3 of scintillator 32 on the opposite side to the surface S6 contacting the substrate 34, and to cover the surface S4 that intersects with the surface S3 (FIG. 5D). $Al_2O_3$ may, for example, be employed as the material of the reflective film 50. The reflective film 50 is formed so as to cover the substrate 34 at portions as the vicinity of the scintillator 32.

In the radiation detector 30 and the radiographic imaging device 10 according to the exemplary embodiment of technology disclosed herein, the rigidity of the bending suppression member 60 is set such that the radius of curvature R of bending that occurs in the substrate 34 due to the weight of the scintillator 32 satisfies Equation (10). Thus the radius of curvature R of bending that occurs in the substrate 34 due to the weight of the scintillator 32 is limited to the range of Equation (10). This thereby enables the risk of the scintillator 32 being damaged due to mutually adjacent columnar crystals 32a contacting each other when, for example, the substrate 34 is handled during processes to manufacture the radiation detector 30 to be reduced, even when bending occurs in the substrate 34 due to the weight of the scintillator 32, compared to cases in which the technology disclosed herein is not applied.

Figure 11A:
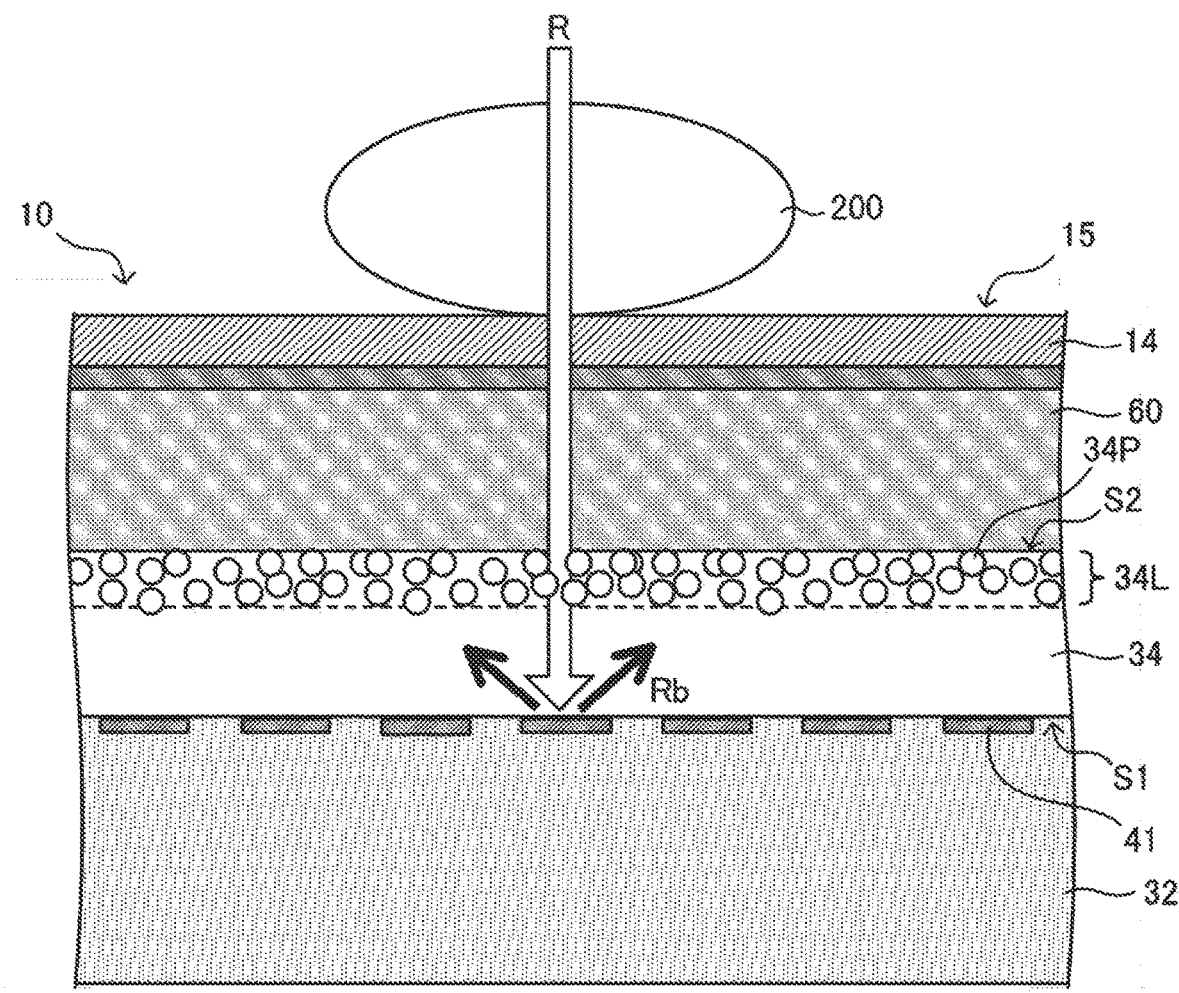
FIG. 11A is a cross-section illustrating back scattering radiation generated inside a substrate containing a fine particle layer.

FIG. 11A and FIG. 11B are cross-sections illustrating examples of a partial configuration of a radiographic imaging device 10 in which an ISS method is applied as the radiation sampling method. FIG. 11A and FIG. 11B each illustrate a case in which the substrate 34 is configured including a base member made from a resin material such as a polyimide or the like. FIG. 11A illustrates a case in which the substrate 34 contains the fine particle layer 34L, and FIG. 11B illustrates a case in which the substrate 34 does not contain a fine particle layer. In cases in which an ISS method is applied, from out of the substrate 34 and the scintillator 32 it is the substrate 34 that is arranged at the radiation-incident face 15 side of the case 14. Namely, the radiation R incident to the radiation-incident face 15 is transmitted through the substrate 34 before being incident to the scintillator 32.

When the radiation is incident to the substrate 34 containing a resin material with a configuration including elements having comparatively small atomic numbers, such as C, H, O, N, etc., a comparatively large amount of back scattering radiation Rb is generated by the Compton effect, which could leak out toward an imaging subject 200. As illustrated in FIG. 11A, by providing the substrate 34 with the fine particle layer 34L that includes fine particles 34P configured from inorganic material including an element that has an atomic number greater than the atomic numbers of the elements configuring the resin material (i.e. C, H, O, and N), back scattering radiation Rb generated in the substrate 34 can be absorbed by the fine particle layer 34L. This enables the amount of back scattering radiation Rb leakage to the imaging subject 200 side to be suppressed in comparison to cases in which the substrate 34 does not include a fine particle layer (see FIG. 11B). Note that the higher the atomic numbers of the elements configuring the fine particles 34P, the greater the effect of absorbing the back scattering radiation Rb increases. However, the amount of radiation absorbed also increases and thus the amount of radiation reaching the scintillator 32 decreases. The atomic numbers of the elements configuring the fine particles 34P are thus preferably not higher than 30.

Figure 7A:
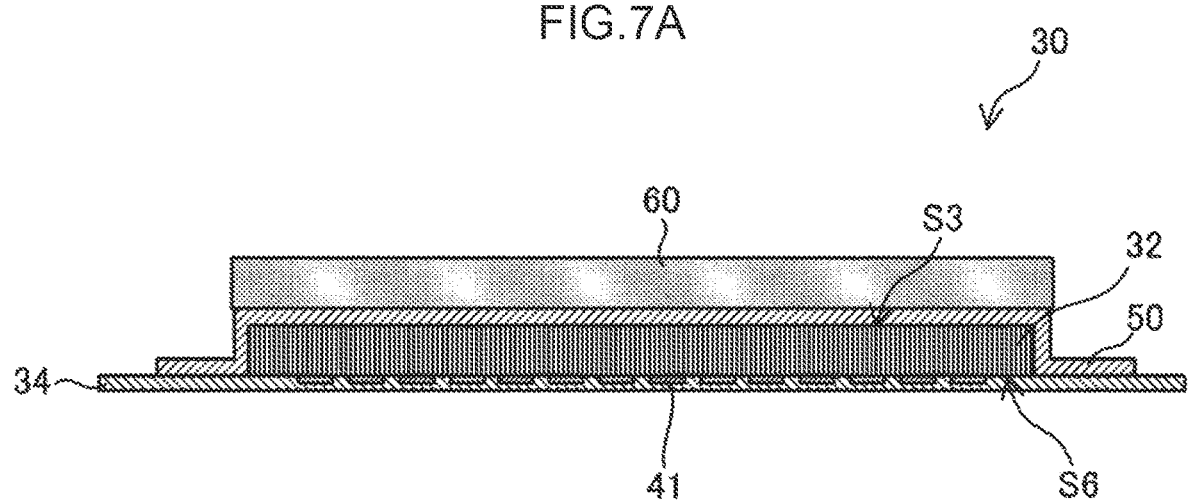
FIG. 7A is a cross-section illustrating an example of a configuration of a radiation detector according to an exemplary embodiment of technology disclosed herein.

Although an example has been described of a case in which the bending suppression member 60 is provided on the second surface S2 side of the substrate 34 in the exemplary embodiment described above, the technology disclosed herein is not limited this approach. For example, as illustrated in FIG. 7A, the bending suppression member 60 may be stacked on the surface S3 side of the scintillator 32 that is the opposite side to the surface S6 in contact with the substrate 34. Adopting such a configuration enables substantially the same advantageous effects to be obtained to cases in which the bending suppression member 60 is provided on the second surface S2 side of the substrate 34.

Figure 7B:
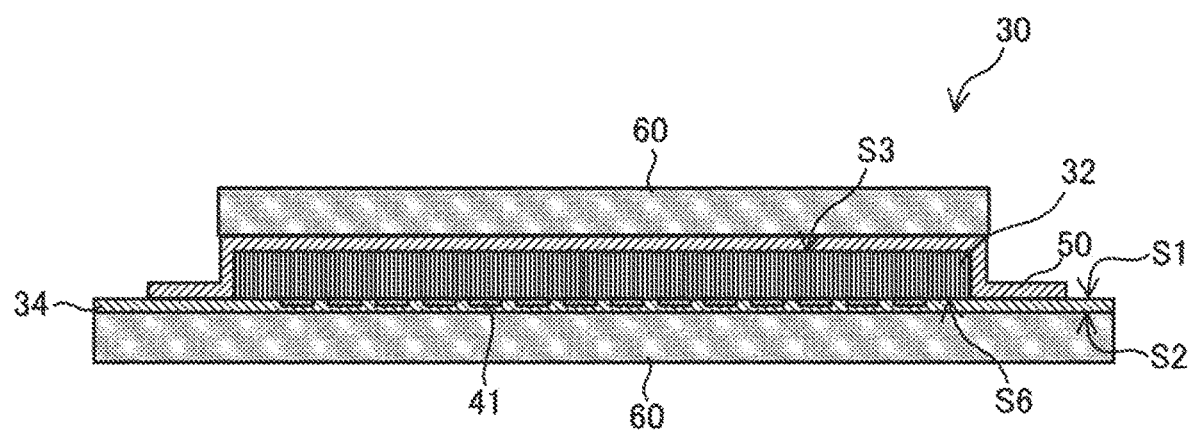
FIG. 7B is a cross-section illustrating an example of a configuration of a radiation detector according to an exemplary embodiment of technology disclosed herein.

Moreover, as illustrated in FIG. 7B, the bending suppression member 60 may be stacked on both the second surface S2 side of the substrate 34 and on the surface S3 side of the scintillator 32 that is the opposite side to the surface S6 in contact with the substrate 34. Stacking the bending suppression member 60 on at least one side from out of the second surface S2 side of the substrate 34 or the surface S3 side of the scintillator 32 that is the opposite side to the surface S6 in contact with the substrate 34 enhances the bending suppression effect exhibited by the bending suppression member 60. Moreover, as illustrated in FIG. 7B, stacking a bending suppression member 60 on both the second surface S2 side of the substrate 34 and the surface S3 side of the scintillator 32 enables the bending suppression effect exhibited by the bending suppression member 60 to be enhanced, enabling the risk of the scintillator 32 being damaged by bending of the substrate 34 to be reduced further. In cases in which bending suppression members 60 are stacked on both the second surface S2 side of the substrate 34 and the surface S3 side of the scintillator 32, the bending suppression member 60 stacked on the second surface S2 side of the substrate 34, this being the radiation-incident side, preferably absorbs a lower amount of radiation than the bending suppression member 60 stacked on the surface S3 side of the scintillator 32.

Second Exemplary Embodiment

Figure 8A:
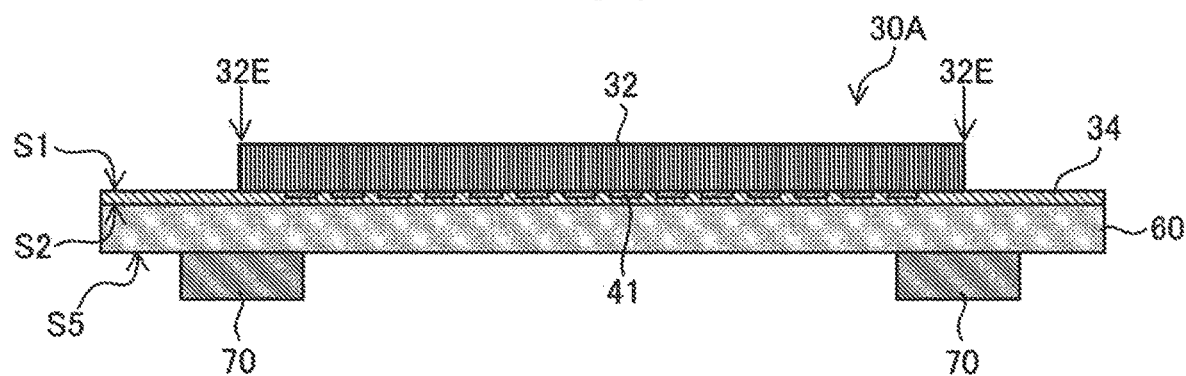
FIG. 8A is a cross-section illustrating an example of a configuration of a radiation detector according to an exemplary embodiment of technology disclosed herein.

FIG. 8A is a cross-section illustrating an example of a configuration of a radiation detector 30A according to a second exemplary embodiment of technology disclosed herein. The radiation detector 30A differs from the radiation detector 30 according to the first exemplary embodiment in the point that reinforcement members 70 are further included in order to reinforce the bending suppression effect of the bending suppression member 60.

In the configuration illustrated in FIG. 8A, the bending suppression member 60 is provided on the second surface S2 side of the substrate 34, and the reinforcement member 70 is provided on the surface S5 side of the bending suppression member 60, this being on the opposite side to the surface of the bending suppression member 60 contacting the substrate 34. The reinforcement members 70 are provided in regions straddling planar direction end portions (outer edges, edges) 32E of the scintillator 32. Namely, the reinforcement members 70 are provided to the bending suppression member 60 on the surface S5 side of the bending suppression member 60 in a state straddling a boundary between regions where the scintillator 32 is present and regions were the scintillator 32 is not present. The reinforcement members 70 preferably have a higher rigidity than that of the substrate 34 from the perspective of reinforcing the bending suppression effect of the bending suppression member 60. Preferable ranges for the bending elastic modulus and the coefficient of thermal expansion of the reinforcement members 70 are the same as those for the bending suppression member 60. The reinforcement members 70 may, for example, be configured from the same material as the bending suppression member 60, or may be configured from a material having a higher rigidity than that of the bending suppression member 60.

Figure 9:
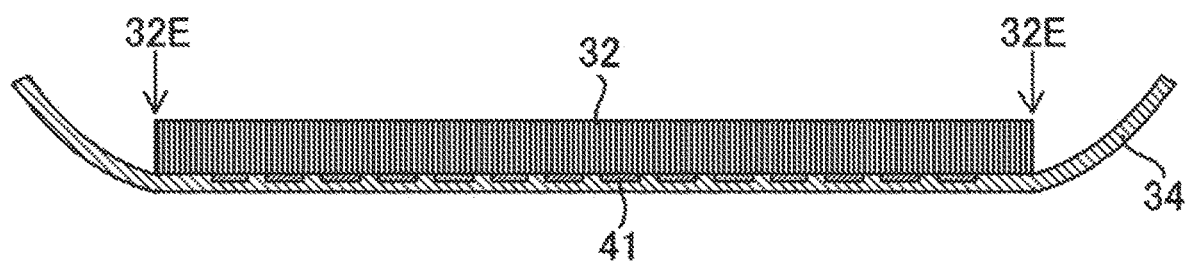
FIG. 9 is a cross-section illustrating an example of a state in which a substrate has bent due to the weight of a scintillator.

FIG. 9 is a cross-section illustrating an example of a state in which the substrate 34 has bent due to the weight of the scintillator 32. As illustrated in FIG. 9, at regions of the substrate 34 over which the scintillator 32 extends, the amount of bending of the substrate 34 is comparatively small due to the rigidity of the scintillator 32. However, at the portions of the substrate 34 corresponding to the end portions 32E of the scintillator 32, the amount of bending of the substrate 34 is comparatively large. At the portions where the amount of bending of the substrate 34 is large, the risk of the scintillator 32 being damaged is higher than at portions where the amount of bending is small.

In the radiation detector 30A according to the second exemplary embodiment of the technology disclosed herein, the reinforcement members 70 are provided in regions straddling the end portions 32E of the scintillator 32 in order to reinforce the bending suppression effect of the bending suppression member 60. This enables the bending of the portions of the substrate 34 corresponding to the end portions 32E of the scintillator 32 to be suppressed compared to cases in which the reinforcement members 70 are not provided. Thus the risk of the scintillator 32 being damaged can be reduced compared to cases in which the reinforcement members 70 are not provided.

Figure 8B:
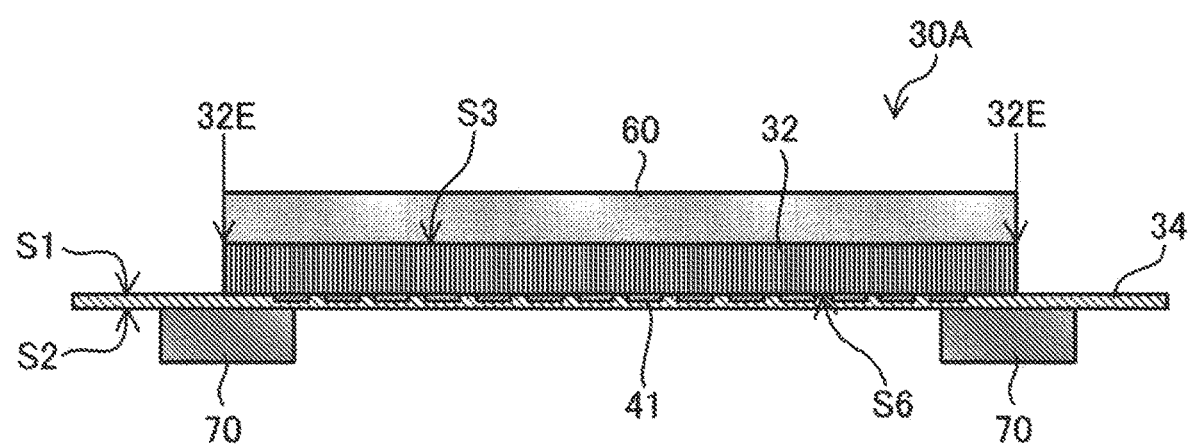
FIG. 8B is a cross-section illustrating an example of a configuration of a radiation detector according to an exemplary embodiment of technology disclosed herein.
Figure 8C:
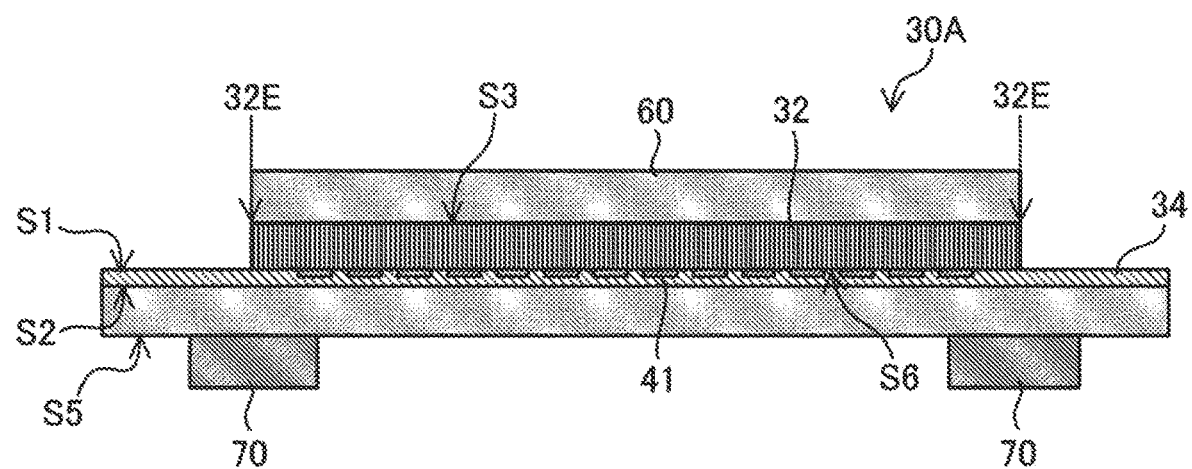
FIG. 8C is a cross-section illustrating an example of a configuration of a radiation detector according to an exemplary embodiment of technology disclosed herein.

Note that as illustrated in FIG. 8B, the reinforcement members 70 may be provided on the second surface S2 of the substrate 34 in cases in which the bending suppression member 60 is provided on the surface S3 of the scintillator 32 on the opposite side to the surface S6 in contact with the substrate 34. Moreover, as illustrated in FIG. 8C, the reinforcement members 70 may be provided on the surface S5 of the bending suppression member 60 on the opposite side to the side of the face in contact with the substrate 34 in cases in which the bending suppression members 60 are provided on both the second surface S2 of the substrate 34 and on the surface S3 of the scintillator 32. In either of the configurations illustrated in FIG. 8B and FIG. 8C, the reinforcement members 70 are provided in regions straddling the end portions (outer edges, edges) 32E of the scintillator 32. Namely, in the configuration illustrated in FIG. 8B, the reinforcement members 70 are provided to the substrate 34 on the second surface S2 side of the substrate 34 in a state straddling boundaries between the region where the scintillator 32 is present and regions where the scintillator 32 is not present. In the configuration illustrated in FIG. 8C, the reinforcement members 70 are provided to the bending suppression member 60 on the surface S5 side of the bending suppression member 60 in a state straddling boundaries between the region where the scintillator 32 is present and regions where the scintillator 32 is not present.

Third Exemplary Embodiment

Figure 12:
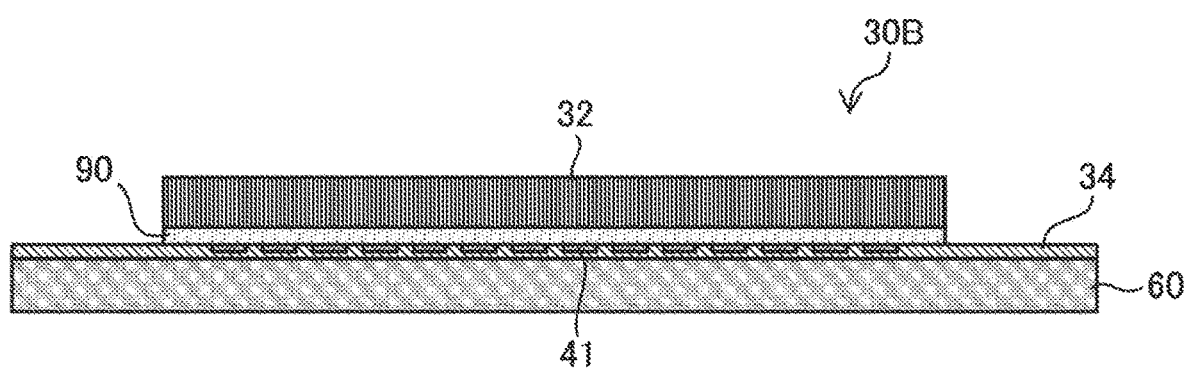
FIG. 12 is a cross-section illustrating an example of a configuration of a radiation detector according to an exemplary embodiment of technology disclosed herein.

FIG. 12 is a cross-section illustrating an example of a configuration of a radiation detector 30B according to a third exemplary embodiment of technology disclosed herein. The radiation detector 30B includes a buffer layer 90 provided between the substrate 34 and the scintillator 32. The buffer layer 90 has a coefficient of thermal expansion lying between the coefficient of thermal expansion of the substrate 34 and the coefficient of thermal expansion of the scintillator 32. A polyimide film or a parylene film may be employed, for example, as the buffer layer 90. In cases in which XENOMAX (registered trademark) is employed as the material of the substrate 34, there is a larger difference between the coefficients of thermal expansion of the substrate 34 and the scintillator 32 than in cases in which, for example, a glass substrate is employed as the substrate 34. Thermal stress acting at the interface between the substrate 34 and the scintillator 32 would accordingly be excessive. Providing the buffer layer 90 between the substrate 34 and the scintillator 32 enables such thermal stress to be suppressed from acting at the interface between the substrate 34 and the scintillator 32.

Other Exemplary Embodiments

FIG. 13 to FIG. 33 are each cross-sections illustrating examples of installation embodiments of the bending suppression member 60 in cases in which the bending suppression member 60 is stacked on the side of the surface of the scintillator 32 on the opposite side to the surface in contact with the substrate 34. In FIG. 13 to FIG. 33, a region where plural pixels 41 are provided on the substrate 34 is denoted a pixel region 41A.

In cases in which the scintillator 32 is formed using a vapor deposition method, as illustrated in FIG. 13 to FIG. 33, the scintillator 32 is formed with a slope with a gradually decreasing thickness on progression toward an outer edge thereof. In the following explanation, a central region of the scintillator 32 where the thickness may be regarded as substantially constant if manufacturing error and measurement error are ignored is referred to as a central portion 33A. Moreover, an outer peripheral region of the scintillator 32 where the thickness is, for example, not more than 90% of the average thickness of the central portion 33A of the scintillator 32 is referred to as a peripheral edge portion 33B. Namely, the scintillator 32 includes a sloping face that slopes with respect to the substrate 34 at the peripheral edge portion 33B.

As illustrated in FIG. 13 to FIG. 33, an adhesion layer 51, a reflective film 50, a bonding layer 52, a protective layer 53, and a bonding layer 54 may be provided between the scintillator 32 and the bending suppression member 60.

The adhesion layer 51 covers the entire front surface of the scintillator 32, including the central portion 33A and the peripheral edge portion 33B of the scintillator 32. The adhesion layer 51 includes a function to fix the reflective film 50 to the scintillator 32. The adhesion layer 51 preferably has light-transmitting properties. Examples of materials that may be employed for the adhesion layer 51 include acrylic-based adhesives, hot-melt-based adhesives, silicone-based bonding agents, and the like. Examples of acrylic-based adhesives include, for example, urethane acrylates, acrylic resin acrylates, epoxy acrylates, and the like. Examples of hot-melt-based adhesives include thermoplastic plastics such as copolymer resins of ethylene vinyl acetate (EVA), copolymer resins of ethylene and acrylic acid (EAA), copolymer resins of ethylene and ethyl acrylate (EEA), copolymers of ethylene/methyl methacrylate (EMMA), and the like. The thickness of the adhesion layer 32 is preferably from 2 µm to 7 µm. Making the thickness of the adhesion layer 32 not less than 2 µm enables the effect of fixing the reflective film 50 to the scintillator 32 to be sufficiently exhibited. Furthermore, this also enables the risk of an air layer being formed between the scintillator 32 and the reflective film 50 to be suppressed. Were an air layer to be formed between the scintillator 32 and the reflective film 50, then there would be concern that multiple reflection of the light emitted from the scintillator 32 might occur, with the light being repeatedly reflected between the air layer and the scintillator 32, and between the air layer and the reflective film 50. Moreover, making the thickness of the adhesion layer 51 not greater than 7 µm enables a reduction in modulation transfer function (MTF) and detective quantum efficiency (DQE) to be suppressed.

The reflective film 50 covers the entire front surface of the adhesion layer 51. The reflective film 50 has a function of reflecting the light converted in the scintillator 32. The reflective film 50 is preferably configured from an organic material. Examples of materials that may be employed for the reflective film 50 include white polyethylene terephthalate (PET), $TiO_2$, $Al_2O_3$, foamed white PET, polyester-based high reflectivity sheets, specular reflective aluminum, and the like. Note that white PET is PET to which a white pigment, such as $TiO_2$, barium sulfate, or the like, has been added. Moreover, polyester-based high reflectivity sheets are sheets (films) having a multi-layer structure of plural superimposed thin polyester sheets. Foamed white PET is white PET having a porous surface. The thickness of the reflective film 50 is preferably from 10 µm to 40 µm.

The bonding layer 52 covers the entire front surface of the reflective film 50. The end portion of the bonding layer 52 also extends as far as the front surface of the substrate 34. Namely, the bonding layer 52 is bonded to the substrate 34 at these end portions. The bonding layer 52 has a function to fix the reflective film 50 and the protective layer 53 to the scintillator 32. The same materials as may be employed in the adhesion layer 51 may be employed as the material of the bonding layer 52. However, the bonding strength of the bonding layer 52 is preferably greater than the bonding strength of the adhesion layer 51.

The protective layer 53 covers the entire front surface of the bonding layer 52. Namely, the protective layer 53 is provided so as to cover the entirety of the scintillator 32, and an end portion of the protective layer 53 also covers a portion of the substrate 34. The protective layer 53 functions as a moisture-proof film to prevent the ingress of moisture into the scintillator 32. Examples of materials that may be employed as the material of the protective layer 53 include organic films including an organic material, such as PET, polyphenylene sulfide (PPS), oriented polypropylene (OPP), polyethylene naphthalate (PEN), polyimide (PI), and the like. Moreover, an ALPET (registered trademark) sheet in which an aluminum layer such as an aluminum foil is bonded to an insulating sheet (film) such as polyethylene terephthalate may be employed as the protective layer 53.

The bending suppression member 60 is provided on the front surface of the protective layer 53, with the bonding layer 54 interposed therebetween. The same materials as may be employed in the adhesion layer 51 and the bonding layer 52 may, for example, be employed as the material of the bonding layer 54.

Figure 13:
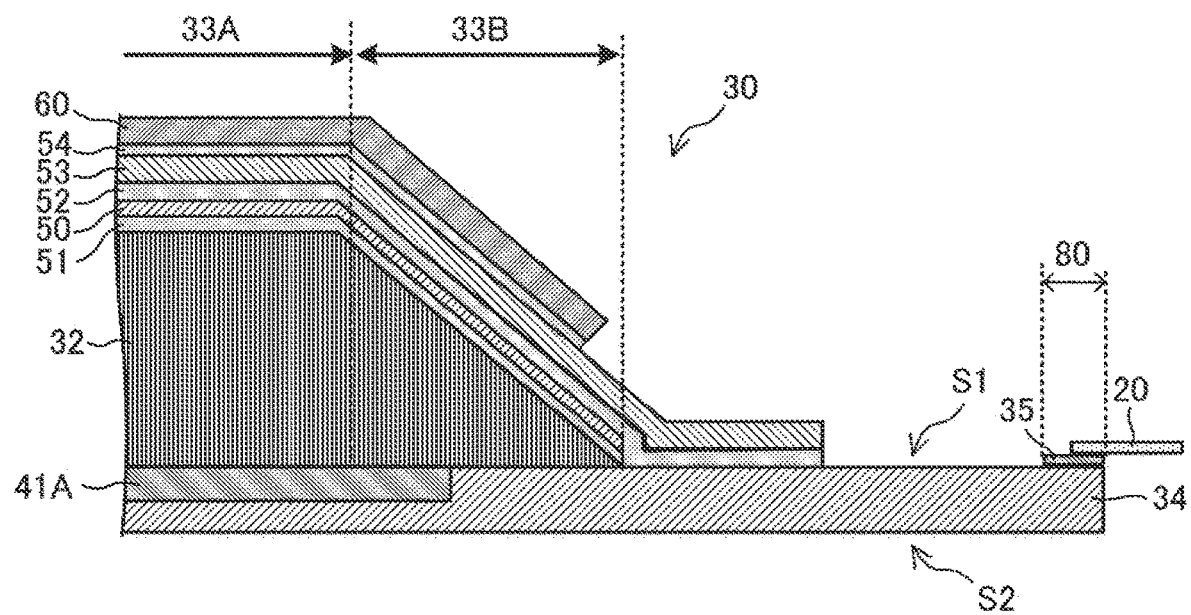
FIG. 13 is a cross-section illustrating an example of a configuration of a radiation detector according to an exemplary embodiment of technology disclosed herein.

In the example illustrated in FIG. 13, the bending suppression member 60 extends over regions corresponding to the central portion 33A and the peripheral edge portion 33B of the scintillator 32, with an outer peripheral portion of the bending suppression member 60 angled so as to follow the slope of the peripheral edge portion 33B of the scintillator 32. The bending suppression member 60 is bonded to the protective layer 53 through the bonding layer 54 at both the region corresponding to the central portion 33A of the scintillator 32 and the region corresponding to the peripheral edge portion 33B of the scintillator 32. In the example illustrated in FIG. 13, an end portion of the bending suppression member 60 is disposed in a region corresponding to the peripheral edge portion 33B of the scintillator 32.

Figure 14:
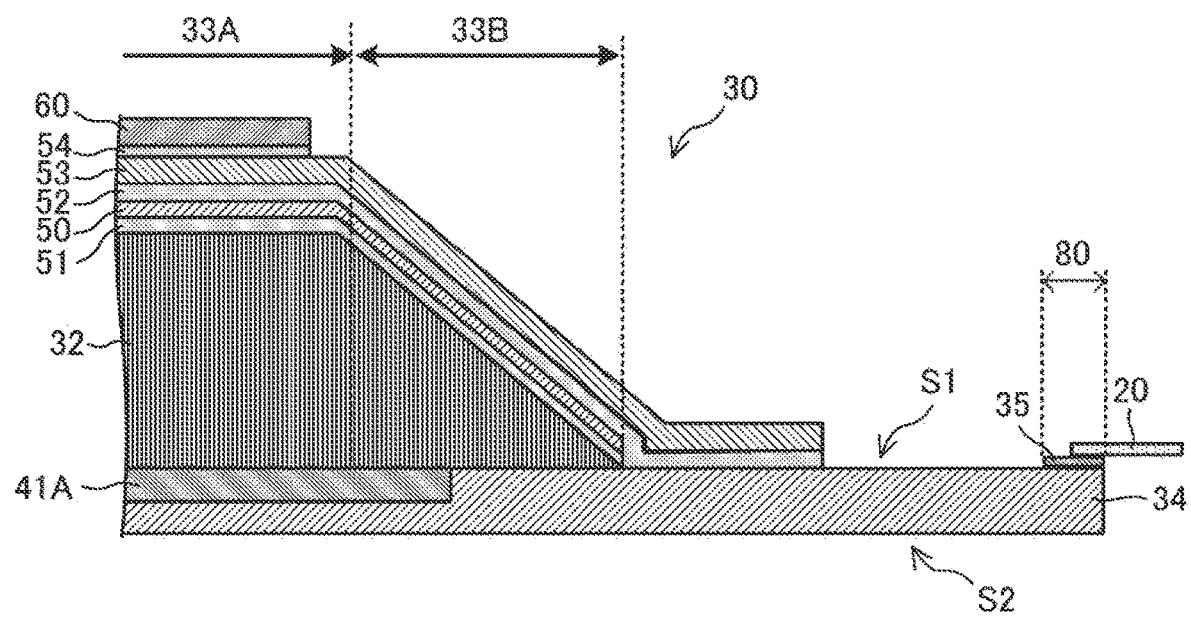
FIG. 14 is a cross-section illustrating an example of a configuration of a radiation detector according to an exemplary embodiment of technology disclosed herein.

As illustrated in FIG. 14, the bending suppression member 60 may be provided only in the region corresponding to the central portion 33A of the scintillator 32. In such cases, the bending suppression member 60 is bonded to the protective layer 53 through the bonding layer 54 in the region corresponding to the central portion 33A of the scintillator 32.

Figure 15:
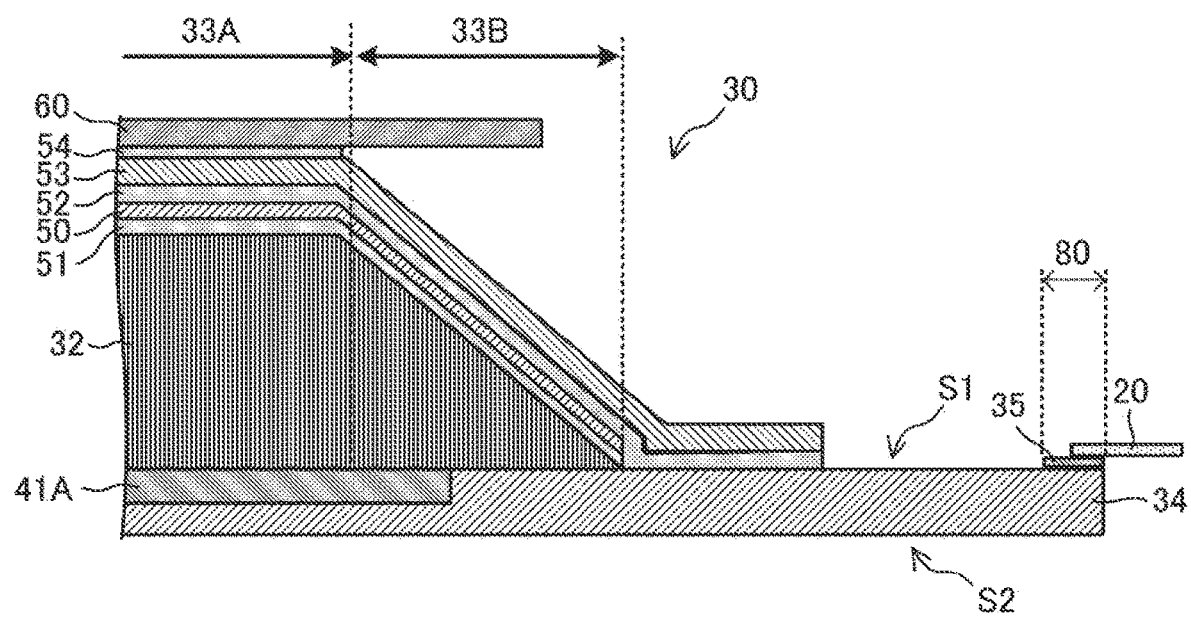
FIG. 15 is a cross-section illustrating an example of a configuration of a radiation detector according to an exemplary embodiment of technology disclosed herein.

As illustrated in FIG. 15, in cases in which the bending suppression member 60 extends over regions corresponding to both the central portion 33A and the peripheral edge portion 33B of the scintillator 32, the bending suppression member 60 may be configured without providing an angled portion to follow the slope of the outer peripheral portions of the scintillator 32. In such cases, the bending suppression member 60 is bonded to the protective layer 53 through the bonding layer 54 in the region corresponding to the central portion 33A of the scintillator 32. A space corresponding to the slope of the peripheral edge portion 33B of the scintillator 32 is formed between the scintillator 32 (the protective layer 53) and the bending suppression member 60 in the region corresponding to the peripheral edge portion 33B of the scintillator 32.

In this example the cable 20 is connected to terminals 35 provided in the connection region 80 at the outer peripheral portion of the substrate 34. The substrate 34 is connected to a control board (see FIG. 45) through the cable 20. There is a concern that the cable 20 might detach from the substrate 34 or positional misalignment might arise were bending of the substrate 34 to occur. In such cases it would be necessary to perform a task to reconnect the cable 20 and the substrate 34. This task to reconnect the cable 20 and the substrate 34 is called re-work. As illustrated in FIG. 13 to FIG. 15, by arranging the end portion of the bending suppression member 60 at the inside of the end portion of the scintillator 32, re-work can be performed more easily than in cases in which the bending suppression member 60 extends to the vicinity of the connection region 80.

As illustrated in FIG. 16 to FIG. 19, the end portion of the bending suppression member 60 may be disposed outside the end portion of the scintillator 32, and the end portions of the bonding layer 52 and the protective layer 53 that both extend onto the substrate 34 may be provided so as to be aligned with each other. Note that there is no need for the position of the end portion of the bending suppression member 60 to align exactly with the position of the end portions of the bonding layer 52 and the protective layer 53.

Figure 16:
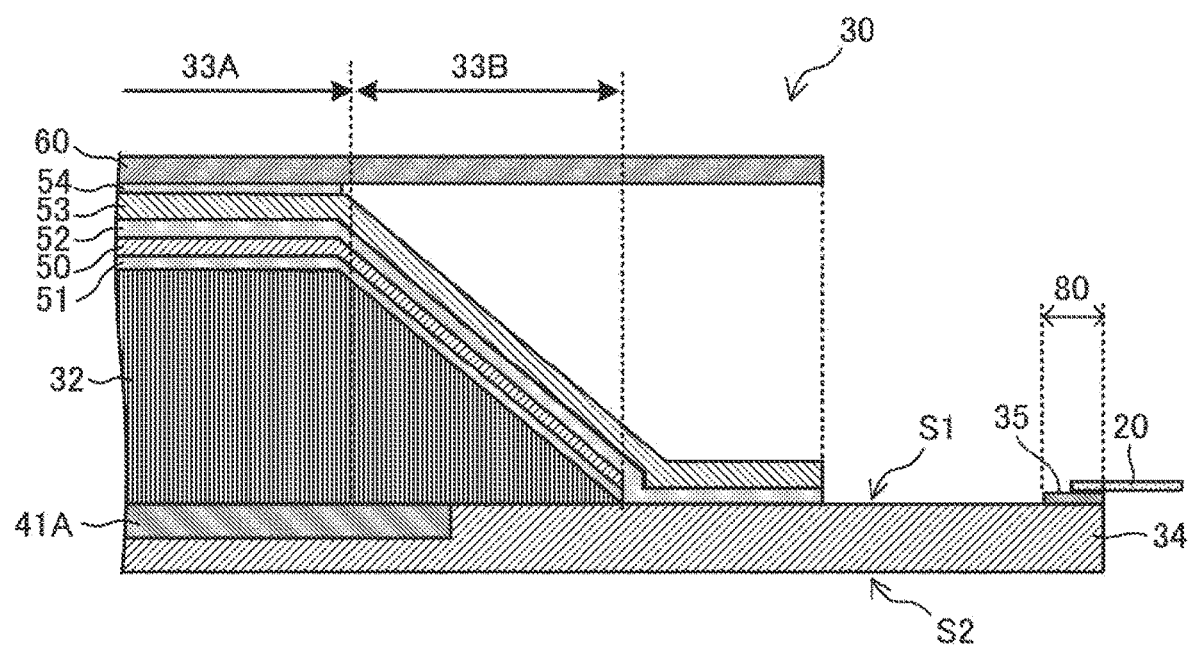
FIG. 16 is a cross-section illustrating an example of a configuration of a radiation detector according to an exemplary embodiment of technology disclosed herein.

In the example illustrated in FIG. 16, the bending suppression member 60 is bonded to the protective layer 53 through the bonding layer 54 in the region corresponding to the central portion 33A of the scintillator 32, and a space corresponding to the slope at the peripheral edge portion 33B of the scintillator 32 is formed between the scintillator 32 (the protective layer 53) and the bending suppression member 60 in the region corresponding to the peripheral edge portion 33B of the scintillator 32 and also in a region further to the outside thereof.

Figure 17:
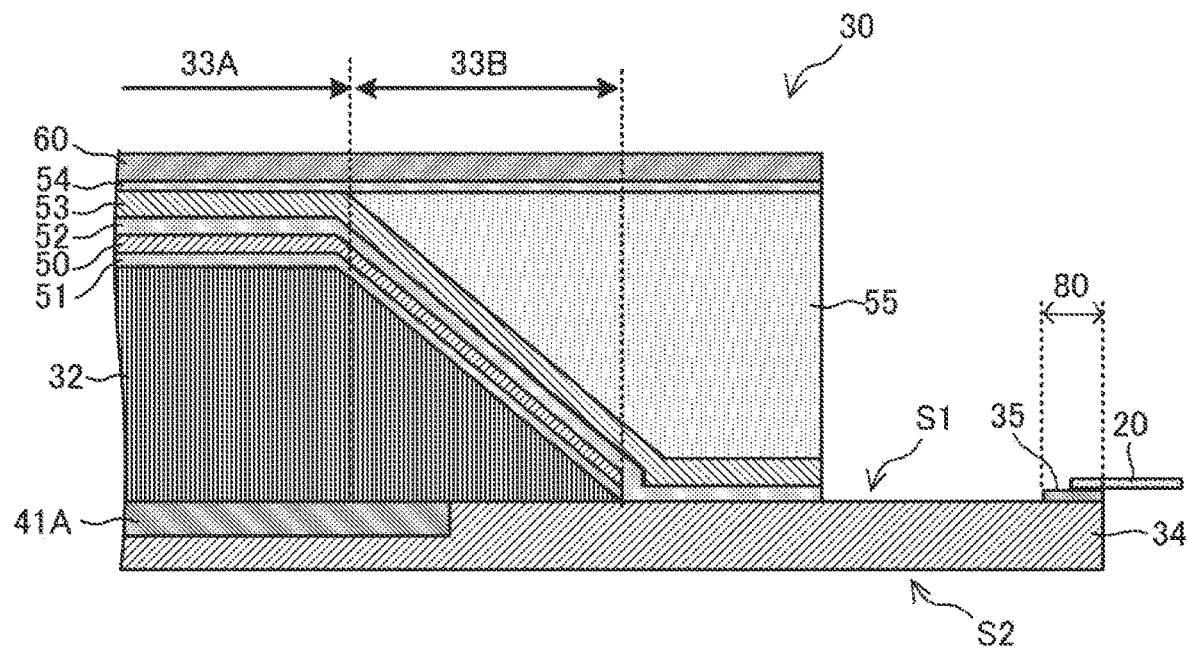
FIG. 17 is a cross-section illustrating an example of a configuration of a radiation detector according to an exemplary embodiment of technology disclosed herein.

In the example illustrated in FIG. 17, a filler 55 is provided in the space formed between the scintillator 32 (the protective layer 53) and the bending suppression member 60 at the region corresponding to the peripheral edge portion 33B of the scintillator 32 and also at the region further to the outside thereof. The material of the filler 55 is not particularly limited, and examples of materials that may be employed therefor include, for example, resins. Note that in the example illustrated in FIG. 17 the bonding layer 54 is provided in the entire region between the bending suppression member 60 and the filler 55 in order to fix the bending suppression member 60 to the filler 55.

The method of forming the filler 55 is not particularly limited. For example, after forming the bonding layer 54 and the bending suppression member 60 in sequence on the scintillator 32 covered by the adhesion layer 51, the reflective film 50, the bonding layer 52, and the protective layer 53, a flowable filler 55 may be poured into be the space formed between the scintillator 32 (the protective layer 53) and the bending suppression member 60, and the filler 55 then cured. Moreover, for example, after forming the scintillator 32, the adhesion layer 51, the reflective film 50, the bonding layer 52, and the protective layer 53 in sequence on the substrate 34, the filler 55 may be formed, and the bonding layer 54 and the bending suppression member 60 may then be formed in sequence so as to cover the scintillator 32 covered by the adhesion layer 51, the reflective film 50, the bonding layer 52, and the protective layer 53 and also cover the filler 55.

By filling the filler 55 into the space formed between the scintillator 32 (the protective layer 53) and the bending suppression member 60 in this manner, the bending suppression member 60 and the scintillator 32 (the protective layer 53) can be better suppressed from detaching from one another than in the embodiment illustrated in FIG. 16. Furthermore, due to adopting a structure in which the scintillator 32 is fixed to the substrate 34 by both the bending suppression member 60 and the filler 55, the scintillator 32 from the substrate 34 can be suppressed from detaching from one another.

Figure 18:
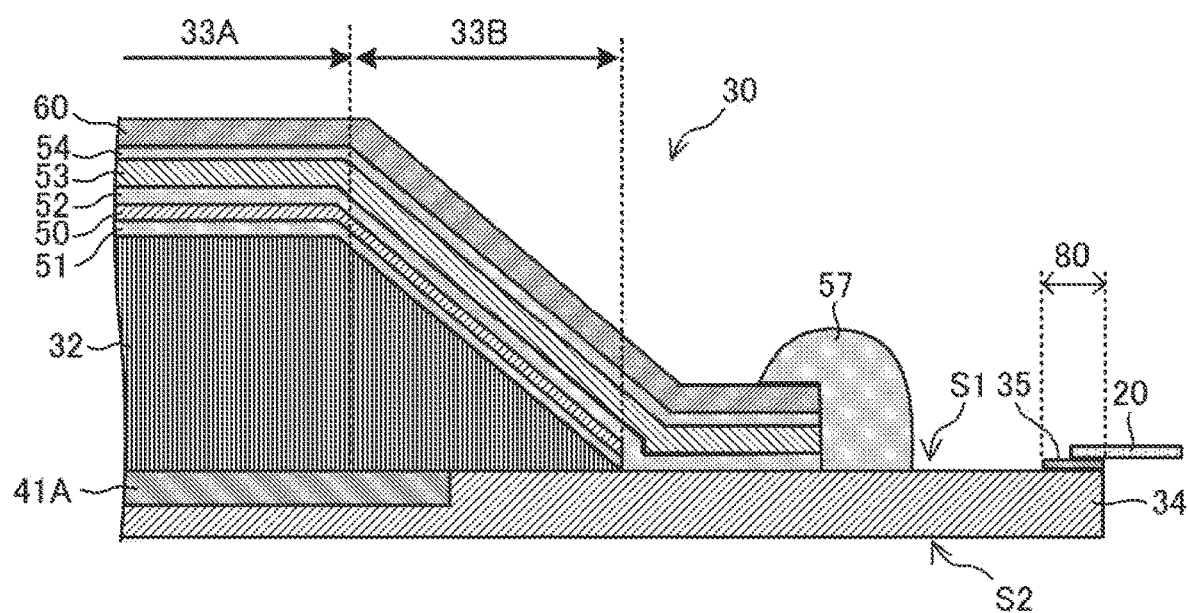
FIG. 18 is a cross-section illustrating an example of a configuration of a radiation detector according to an exemplary embodiment of technology disclosed herein.

In the example illustrated in FIG. 18, the outer peripheral portion of the bending suppression member 60 is angled so as to follow the slope of the peripheral edge portion 33B of the scintillator 32, and so as also to cover the portions of the bonding layer 52 and the protective layer 53 that cover the substrate 34. Moreover, the end portion of the bending suppression member 60 and the end portions of the bonding layer 52 and the protective layer 53 are aligned with each other. Note that there is no need for the position of the end portion of the bending suppression member 60 to align exactly with the position of the end portions of the bonding layer 52 and the protective layer 53.

The end portions of the bending suppression member 60, the bonding layer 54, the protective layer 53, and the bonding layer 52 are sealed with a sealing member 57. The sealing member 57 is preferably provided in a region spanning from the front surface of the substrate 34 to the front surface of the bending suppression member 60, and in a region not covering the pixel region 41A. Resins may be employed as the material of the sealing member 57, and thermoplastic resins are particularly preferably employed therefor. Specifically glues such as acrylic glues, urethane based glues, and the like may be employed as the sealing member 57. The bending suppression member 60 has a higher rigidity than that of the protective layer 53, and there is a concern that recovery force due to the angle attempting to straighten out at the angled portion of the bending suppression member 60 might act to cause the protective layer 53 to detach. Sealing the end portions of the bending suppression member 60, the bonding layer 54, the protective layer 53, and the bonding layer 52 using the sealing member 57 enables such detachment of the protective layer 53 to be suppressed.

Figure 19:
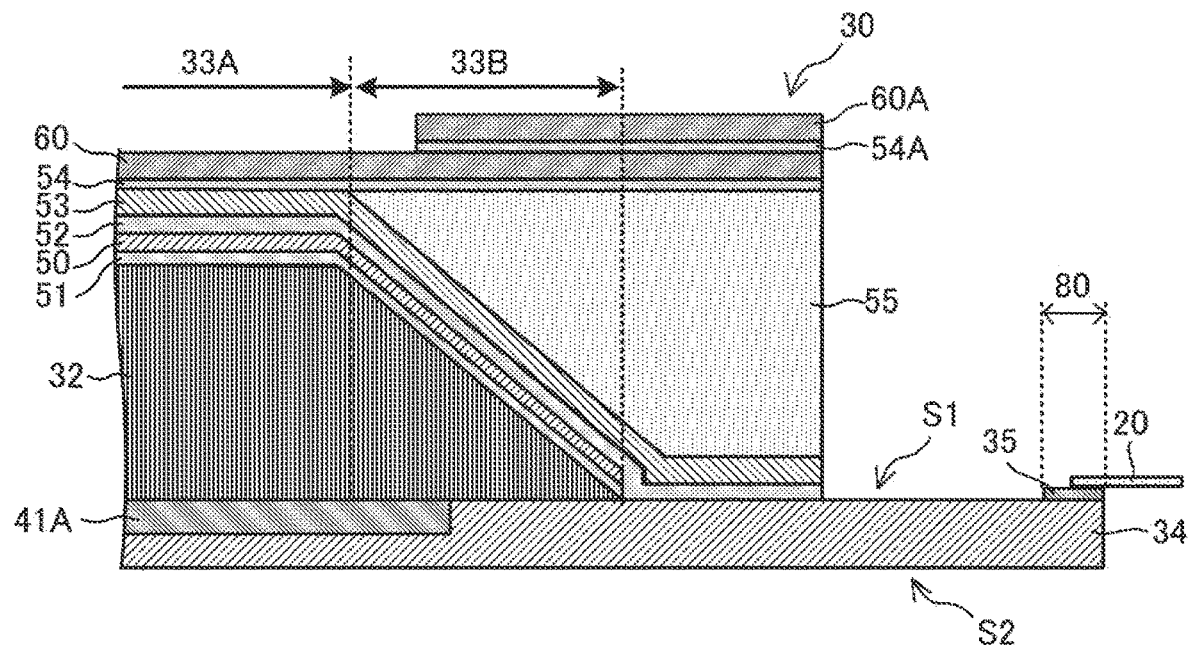
FIG. 19 is a cross-section illustrating an example of a configuration of a radiation detector according to an exemplary embodiment of technology disclosed herein.

Similarly to in the embodiment illustrated in FIG. 17, in the example illustrated in FIG. 19, the filler 55 is provided in a space formed between the scintillator 32 (the protective layer 53) and the bending suppression member 60 at the region corresponding to the peripheral edge portion 33B of the scintillator 32 and also at the region further to the outside thereof. Moreover, in the region corresponding to the end portion of the scintillator 32 an additional and separate bending suppression member 60A is stacked on the front surface of the bending suppression member 60 with a bonding layer 54A interposed therebetween. More specifically, the bending suppression member 60A is provided in a region straddling the end portion (outer edge, edge) of the scintillator 32. The bending suppression member 60A may be configured from the same materials as the bending suppression member 60. As illustrated in FIG. 9, the amount of bending of the substrate 34 is comparatively large at the end portions of the scintillator 32. Forming a multi-layer structure using the bending suppression members 60 and 60A at the region corresponding to the end portion of the scintillator 32 enables the effect of suppressing bending of the substrate 34 at the end portion of the scintillator 32 to be enhanced.

As illustrated in FIG. 16 to FIG. 19, in cases in which the end portion of the bending suppression member 60 is arranged further to the outside than the end portion of the scintillator 32 and is provided so as to be aligned with the end portions of the bonding layer 52 and the protective layer 53, re-work can also be performed more easily than in cases in which the bending suppression member 60 extends as far as the vicinity of the connection region 80.

As illustrated in FIG. 20 to FIG. 23, a configuration may be adopted in which the end portion of the bending suppression member 60 is provided so as to be positioned further outside than the end portions of the bonding layer 52 and the protective layer 53 that extend onto the substrate 34, and so as to be positioned at the inside of the end portion of the substrate 34.

Figure 20:
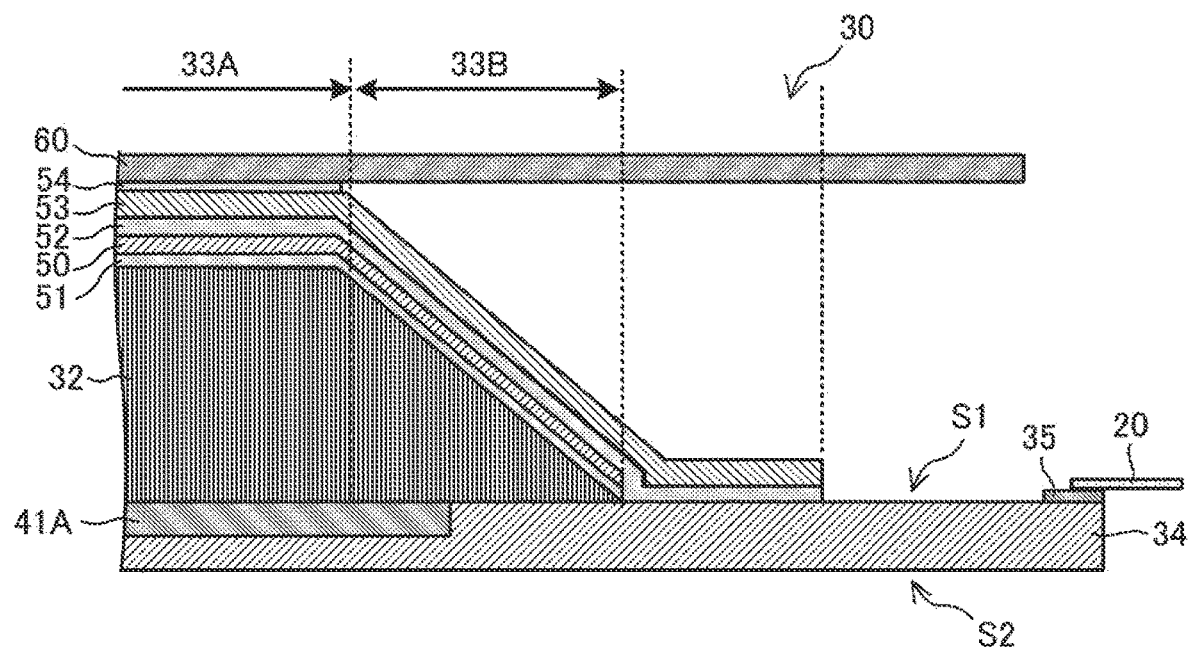
FIG. 20 is a cross-section illustrating an example of a configuration of a radiation detector according to an exemplary embodiment of technology disclosed herein.

In the example illustrated in FIG. 20, the bending suppression member 60 is bonded to the protective layer 53 through the bonding layer 54 at the region corresponding to the central portion 33A of the scintillator 32, and in the region corresponding to the peripheral edge portion 33B of the scintillator 32 and also in the region further to the outside thereof a space corresponding to the slope of the peripheral edge portion 33B of the scintillator 32 is formed between the scintillator 32 (the protective layer 53) and the bending suppression member 60, and between the substrate 34 and the bending suppression member 60.

Figure 21:
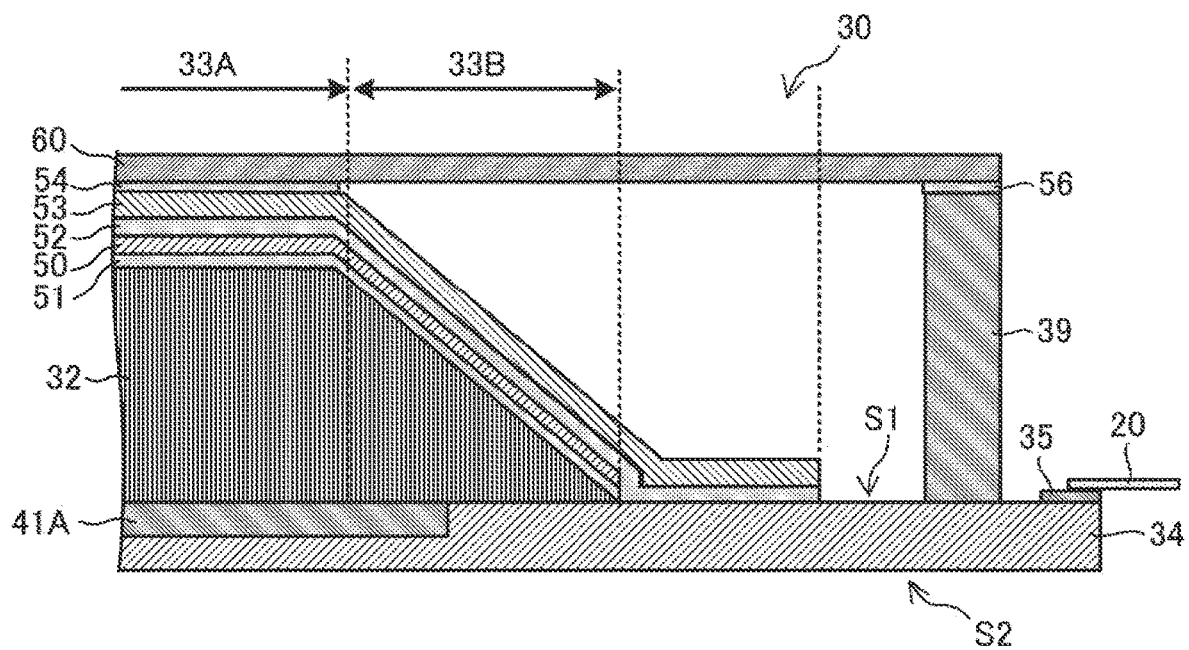
FIG. 21 is a cross-section illustrating an example of a configuration of a radiation detector according to an exemplary embodiment of technology disclosed herein.

In the example illustrated in FIG. 21, the end portion of the bending suppression member 60 is supported by a spacer 39. Namely, one end of the spacer 39 is connected to the first surface S1 of the substrate 34, and the other end of the spacer 39 is connected to the end portion of the bending suppression member 60 through a bonding layer 56. By supporting the end portion of the bending suppression member 60 that extends so as to form a space between itself and the substrate 34 using the spacer 39, detachment of the bending suppression member 60 can be suppressed. Moreover, the bending suppression effect from the bending suppression member 60 can be caused to act as far as the vicinity of the end portion of the substrate 34. Note that instead of providing the spacer 39, a filler may be filled into the space formed between the scintillator 32 (the protective layer 53) and the bending suppression member 60, and between the substrate 34 and the bending suppression member 60, in a similar manner to the example illustrated in FIG. 17.

Figure 22:
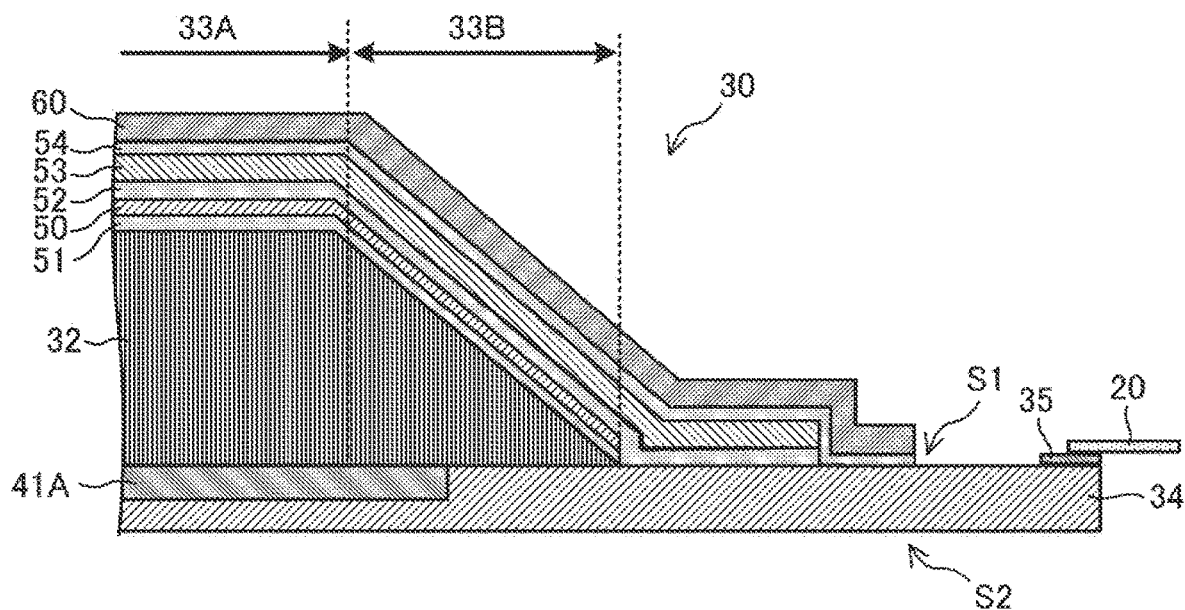
FIG. 22 is a cross-section illustrating an example of a configuration of a radiation detector according to an exemplary embodiment of technology disclosed herein.

In the example illustrated in FIG. 22, the outer peripheral portion of the bending suppression member 60 is angled so as to follow the slope at the peripheral edge portion 33B of the scintillator 32, and the outer peripheral portion of the bending suppression member 60 covers the portion where the bonding layer 52 and the protective layer 53 cover the substrate 34 and also covers the substrate 34 at the outside thereof. Namely, the end portions of the bonding layer 52 and the protective layer 53 are sealed by the bending suppression member 60. The portions of the bending suppression member 60 that extend over the substrate 34 are bonded to the substrate 34 though the bonding layer 54. By covering the end portions of the bonding layer 52 and the protective layer 53 using the bending suppression member 60 in this manner, detachment of the protective layer 53 can be suppressed. Note that a sealing member may be employed to seal the end portions of the bending suppression member 60, in a similar manner to the example illustrated in FIG. 18.

Figure 23:
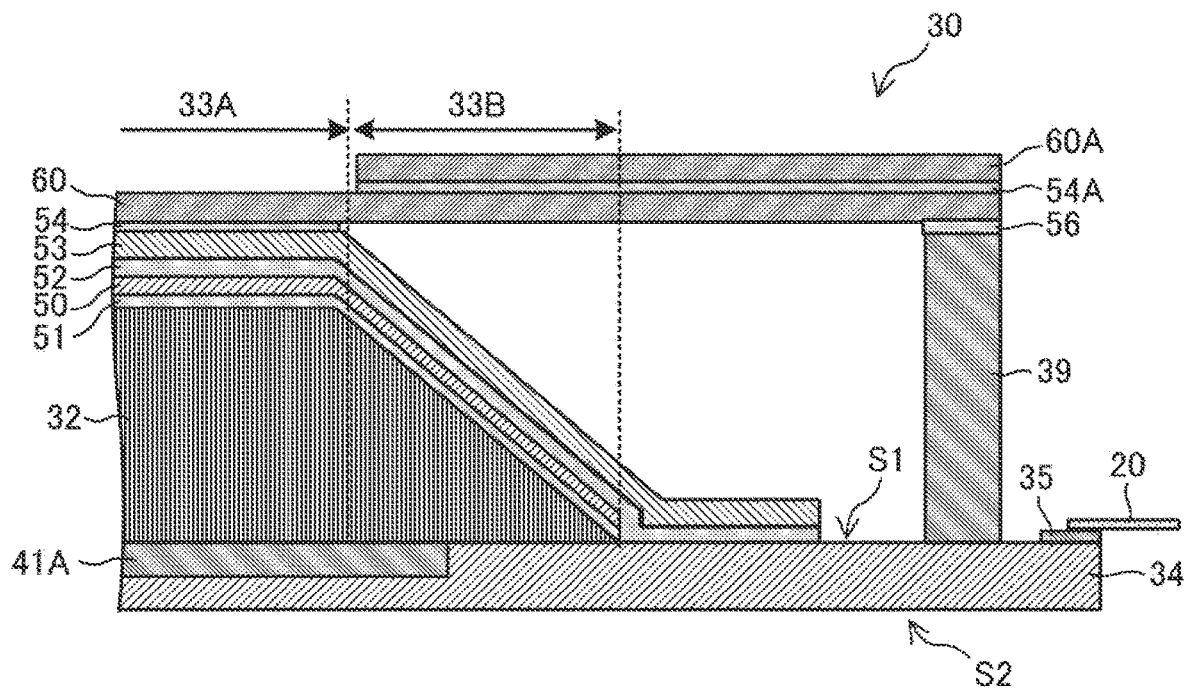
FIG. 23 is a cross-section illustrating an example of a configuration of a radiation detector according to an exemplary embodiment of technology disclosed herein.

In the example illustrated in FIG. 23, in an embodiment in which the end portion of the bending suppression member 60 is supported by the spacer 39, an additional and separate bending suppression member 60A is stacked on a front surface of the bending suppression member 60 at a region corresponding to the end portion of the scintillator 32, with a bonding layer 54A interposed therebetween. More specifically, the bending suppression member 60A is provided in a region straddling the end portion (outer edge, edge) of the scintillator 32. The bending suppression member 60A may be configured from the same materials as the bending suppression member 60. As illustrated in FIG. 9, the amount of bending of the substrate 34 is comparatively large at the end portions of the scintillator 32. Forming a multi-layer structure using the bending suppression members 60 and 60A at the region corresponding to the end portion of the scintillator 32 enables the effect of suppressing bending of the substrate 34 to be enhanced at the end portion of the scintillator 32. Note that instead of providing the spacer 39, a filler may be filled into the space formed between the scintillator 32 (the protective layer 53) and the bending suppression member 60, and between the substrate 34 and the bending suppression member 60, in a similar manner to the example illustrated in FIG. 17.

As illustrated in FIG. 24 to FIG. 28, the end portion of the bending suppression member 60 may be provided so as to be aligned with the end portion of the substrate 34. Note that there is no need for the position of the end portion of the bending suppression member 60 to align exactly with the position of the end portion of the substrate 34.

Figure 24:
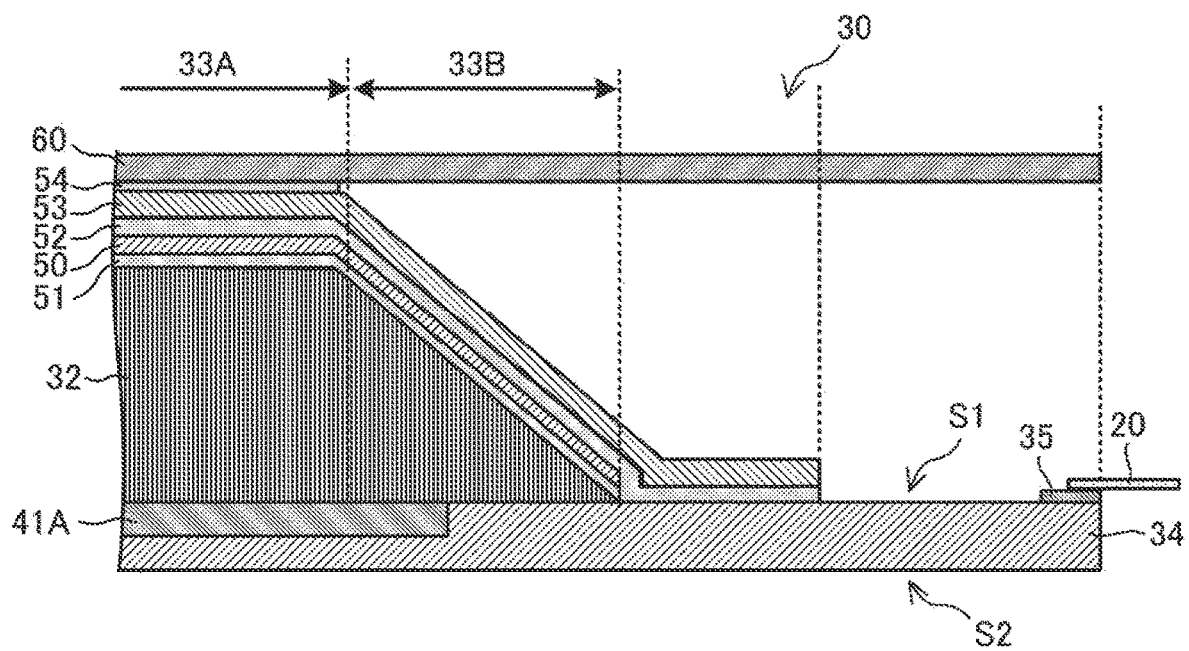
FIG. 24 is a cross-section illustrating an example of a configuration of a radiation detector according to an exemplary embodiment of technology disclosed herein.

In the example illustrated in FIG. 24, the bending suppression member 60 is bonded to the protective layer 53 through the bonding layer 54 at a region corresponding to the central portion 33A of the scintillator 32, and a space corresponding to the slope of the peripheral edge portion 33B of the scintillator 32 is formed between the scintillator 32 (the protective layer 53) and the bending suppression member 60, and between the substrate 34 and the bending suppression member 60, at a region corresponding to the peripheral edge portion 33B of the scintillator 32 and also at a region further to the outside thereof.

Figure 25:
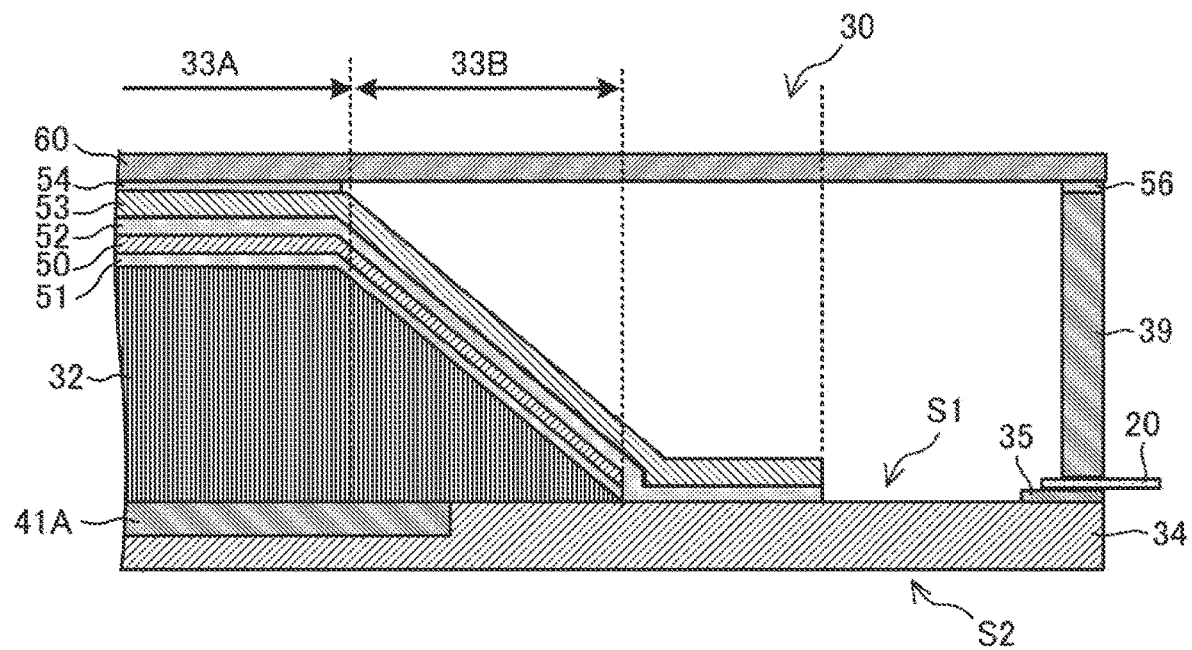
FIG. 25 is a cross-section illustrating an example of a configuration of a radiation detector according to an exemplary embodiment of technology disclosed herein.

In the example illustrated in FIG. 25, the end portion of the bending suppression member 60 is supported by the spacer 39. Namely, one end of the spacer 39 is connected to the cable 20 provided at the end portion of the substrate 34, and the other end of the spacer 39 is connected to the end portion of the bending suppression member 60 through a bonding layer 56. By using the spacer 39 to support the end portion of the bending suppression member 60 that extends so as to form a space between itself and the substrate 34, detachment of the bending suppression member 60 can be suppressed. Moreover, the bending suppression effect from the bending suppression member 60 can be caused to act as far as the vicinity of the end portion of the substrate 34.

Figure 26:
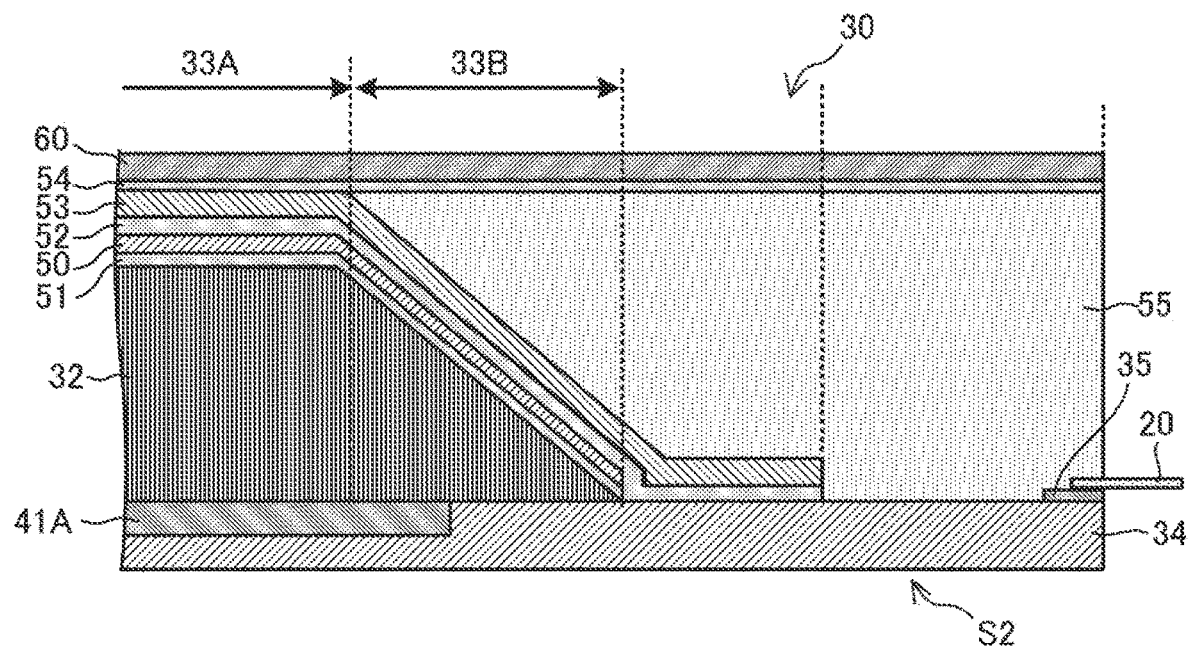
FIG. 26 is a cross-section illustrating an example of a configuration of a radiation detector according to an exemplary embodiment of technology disclosed herein.

In the example illustrated in FIG. 26, the space formed between the scintillator 32 (the protective layer 53) and the bending suppression member 60, and between the substrate 34 and the bending suppression member 60, is filled by the filler 55. In the present exemplary embodiment the connection portions between the cable 20 and the terminals 35 are covered by the filler 55. Thus by filling the space formed between the scintillator 32 (the protective layer 53) and the bending suppression member 60, and between the substrate 34 and the bending suppression member 60, with the filler 55, the bending suppression member 60 and the scintillator 32 (the protective layer 53) can be better suppressed from detaching from one another than in the embodiment illustrated in FIG. 24. Furthermore, due to the scintillator 32 having a structure fixed to the substrate 34 by both the bending suppression member 60 and the filler 55, the scintillator 32 and the substrate 34 can be suppressed from detaching from one another. Moreover, since the connection portions between the cable 20 and the terminals 35 are covered by the filler 55, detachment of the cable 20 can also be suppressed.

Figure 27:
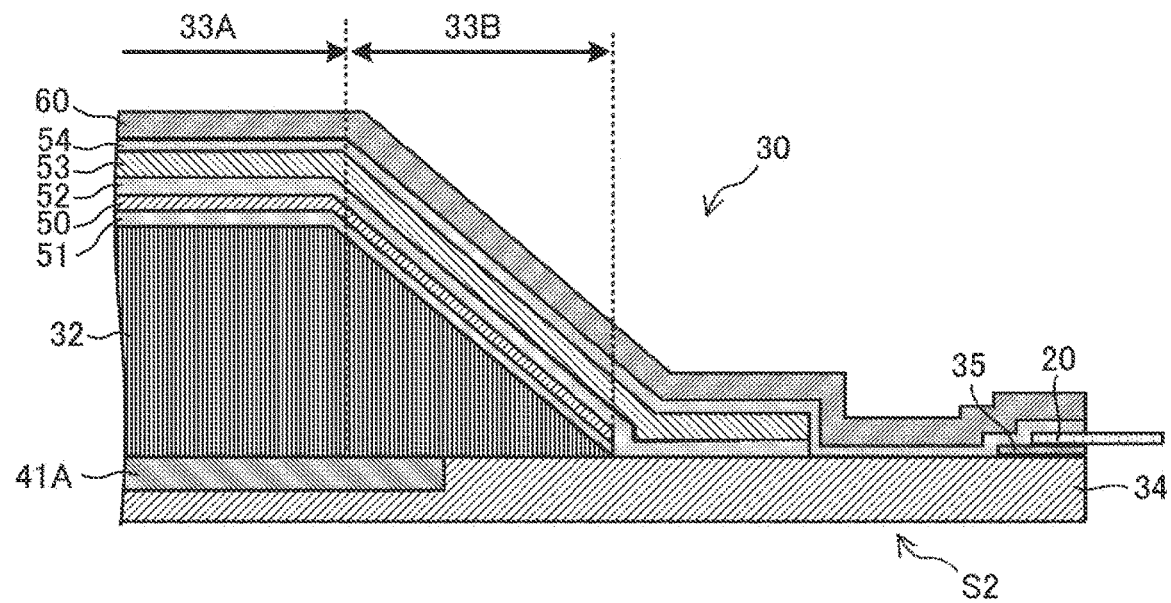
FIG. 27 is a cross-section illustrating an example of a configuration of a radiation detector according to an exemplary embodiment of technology disclosed herein.

In the example illustrated in FIG. 27, the outer peripheral portion of the bending suppression member 60 is angled so as to follow the slope of the peripheral edge portion 33B of the scintillator 32. The outer peripheral portion of the bending suppression member 60 also covers a portion where the bonding layer 52 and the protective layer 53 cover the substrate 34, a portion of the substrate at the outside thereof, and the connection portion between the cable 20 and the terminals 35. The portions of the bending suppression member 60 extending over the substrate 34 and over the cable 20 are respectively bonded to the substrate 34 and the cable 20 through the bonding layer 54. The connection portions between the cable 20 and the terminals 35 are covered by the bending suppression member 60, enabling detachment of the cable 20 to be suppressed. Moreover, since the other end of the cable 20 is anticipated to be connected to a control board mounted with electronic components, there is a concern regarding comparatively large bending of the substrate 34 occurring at the connection portions between the cable 20 and the terminals 35. The connection portions between the cable 20 and the terminals 35 are covered by the bending suppression member 60, enabling bending of the substrate 34 at these portions to be suppressed.

Figure 28:
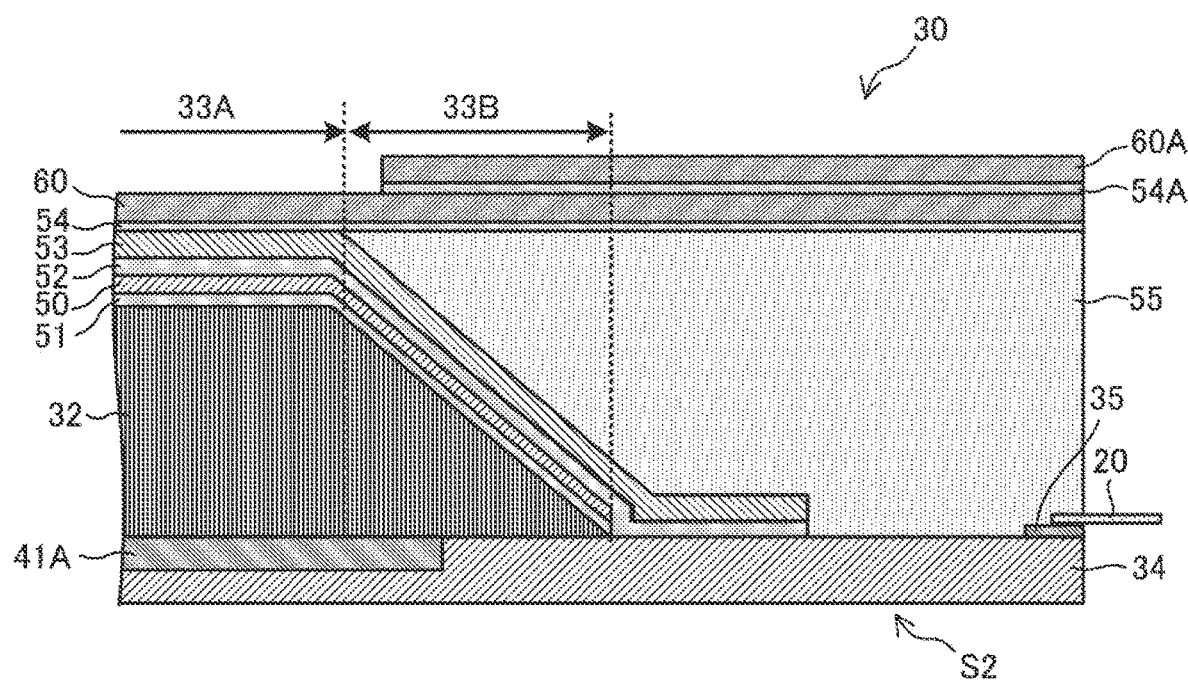
FIG. 28 is a cross-section illustrating an example of a configuration of a radiation detector according to an exemplary embodiment of technology disclosed herein.

In the example illustrated in FIG. 28, a space formed between the scintillator 32 (the protective layer 53) and the bending suppression member 60, and between the substrate 34 and the bending suppression member 60, is filled with the filler 55. Moreover, an additional and separate bending suppression member 60A is stacked on a front surface of the bending suppression member 60 at a region corresponding to the end portion of the scintillator 32, with a bonding layer 54A interposed therebetween. More specifically, the bending suppression member 60A is provided in a region straddling the end portion (outer edge, edge) of the scintillator 32. The bending suppression member 60A may be configured from the same materials as the bending suppression member 60. As illustrated in FIG. 9, the amount of bending of the substrate 34 is comparatively large at the end portions of the scintillator 32. Forming a multi-layer structure using the bending suppression members 60 and 60A at the region corresponding to the end portion of the scintillator 32 enables the effect of suppressing bending of the substrate 34 to be enhanced at the end portion of the scintillator 32.

As illustrated in FIG. 29 to FIG. 33, the end portion of the bending suppression member 60 may be provided so as to be in a position further outside than the end portion of the substrate 34.

Figure 29:
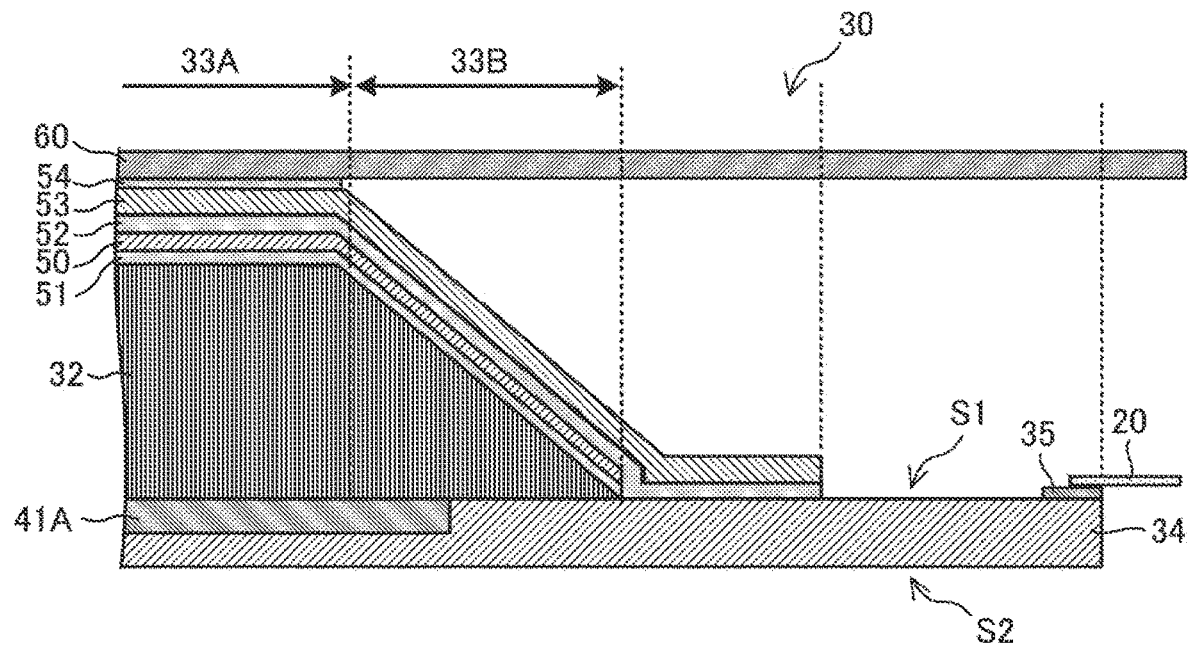
FIG. 29 is a cross-section illustrating an example of a configuration of a radiation detector according to an exemplary embodiment of technology disclosed herein.

In the example illustrated in FIG. 29, the bending suppression member 60 is bonded to the protective layer 53 through the bonding layer 54 at a region corresponding to the central portion 33A of the scintillator 32, and a space corresponding to the slope of the peripheral edge portion 33B of the scintillator 32 is formed between the scintillator 32 (the protective layer 53) and the bending suppression member 60, and between the substrate 34 and the bending suppression member 60, at the region corresponding to the peripheral edge portion 33B of the scintillator 32 and also at the region further to the outside thereof.

Figure 30:
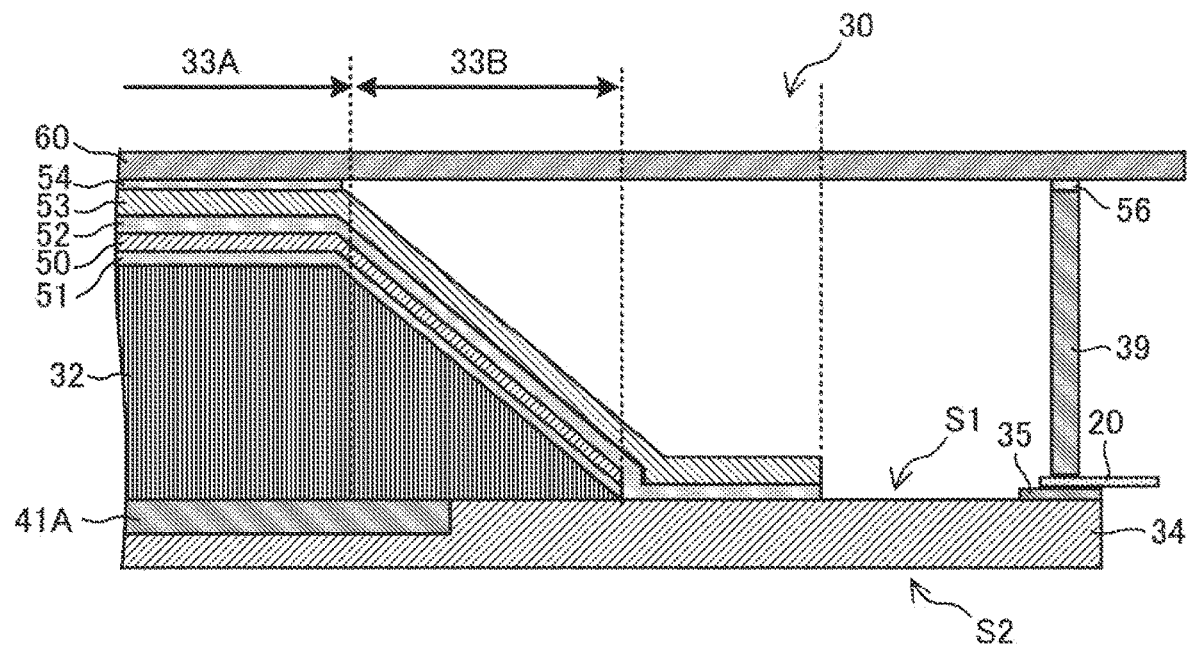
FIG. 30 is a cross-section illustrating an example of a configuration of a radiation detector according to an exemplary embodiment of technology disclosed herein.

In the example illustrated in FIG. 30, the end portion of the bending suppression member 60 is supported by the spacer 39. Namely, one end of the spacer 39 is connected to the cable 20 provided at the end portion of the substrate 34, and the other end of the spacer 39 is connected to the end portion of the bending suppression member 60 through a bonding layer 56. By using the spacer 39 to support the end portion of the bending suppression member 60 that extends so as to form the space between itself and the substrate 34, detachment of the bending suppression member 60 can be suppressed. Moreover, the bending suppression effect from the bending suppression member 60 can be caused to act as far as the vicinity of the end portion of the substrate 34.

Figure 31:
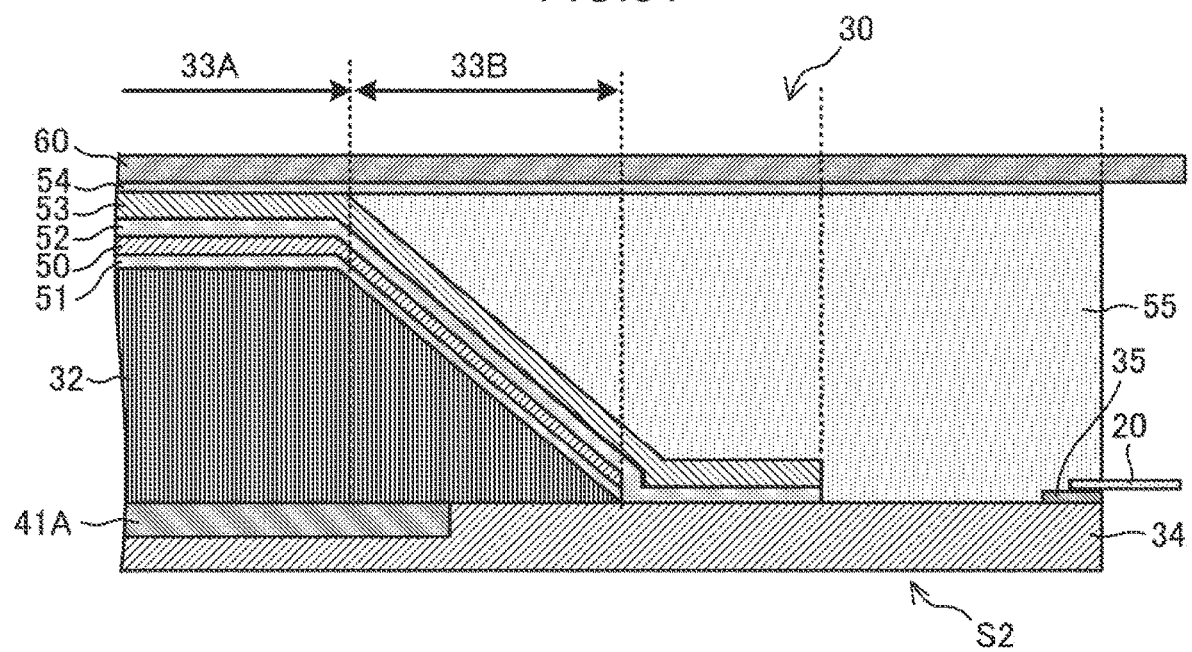
FIG. 31 is a cross-section illustrating an example of a configuration of a radiation detector according to an exemplary embodiment of technology disclosed herein.

In the example illustrated in FIG. 31, the filler 55 is filled into the space formed between the scintillator 32 (the protective layer 53) and the bending suppression member 60, and between the substrate 34 and the bending suppression member 60. In the present exemplary embodiment the connection portions between the cable 20 and the terminals 35 are covered by the filler 55. By filling the filler 55 into the space formed between the scintillator 32 (the protective layer 53) and the bending suppression member 60 and between the substrate 34 and the bending suppression member 60 in this manner, the bending suppression member 60 and the scintillator 32 (the protective layer 53) can be better suppressed from detaching from one another than in the embodiment illustrated in FIG. 29. Furthermore, due to the scintillator 32 having a structure fixed to the substrate 34 by both the bending suppression member 60 and the filler 55, the scintillator 32 and the substrate 34 can be suppressed from detaching from one another. Moreover, since the connection portions between the cable 20 and the terminals 35 are covered by the filler 55, detachment of the cable 20 can be suppressed.

Figure 32:
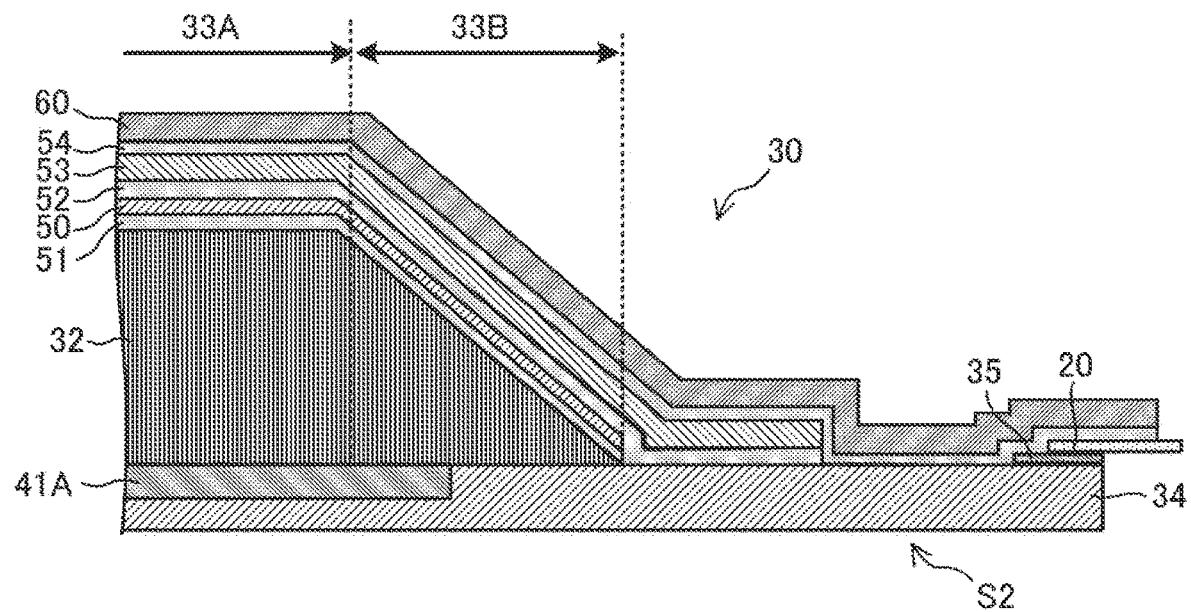
FIG. 32 is a cross-section illustrating an example of a configuration of a radiation detector according to an exemplary embodiment of technology disclosed herein.

In the example illustrated in FIG. 32, the outer peripheral portion of the bending suppression member 60 is angled so as to follow the slope of the peripheral edge portion 33B of the scintillator 32. The outer peripheral portion of the bending suppression member 60 also covers the portion where the bonding layer 52 and the protective layer 53 cover the substrate 34, the portion on the substrate at the outside thereof, and the connection portion between the cable 20 and the terminals 35. The portions of the bending suppression member 60 extending over the substrate 34 and over the cable 20 are respectively bonded to the substrate 34 and the cable 20 through the bonding layer 54. By covering the connection portions between the cable 20 and the terminals 35 with the bending suppression member 60, detachment of the cable 20 can be suppressed. Moreover, since the other end of the cable 20 is anticipated to be connected to a control board mounted with electronic components, there is a concern regarding comparatively large bending of the substrate 34 at the connection portions between the cable 20 and the terminals 35. The connection portions between the cable 20 and the terminals 35 are covered by the bending suppression member 60, enabling bending of the substrate 34 at these portions to be suppressed.

Figure 33:
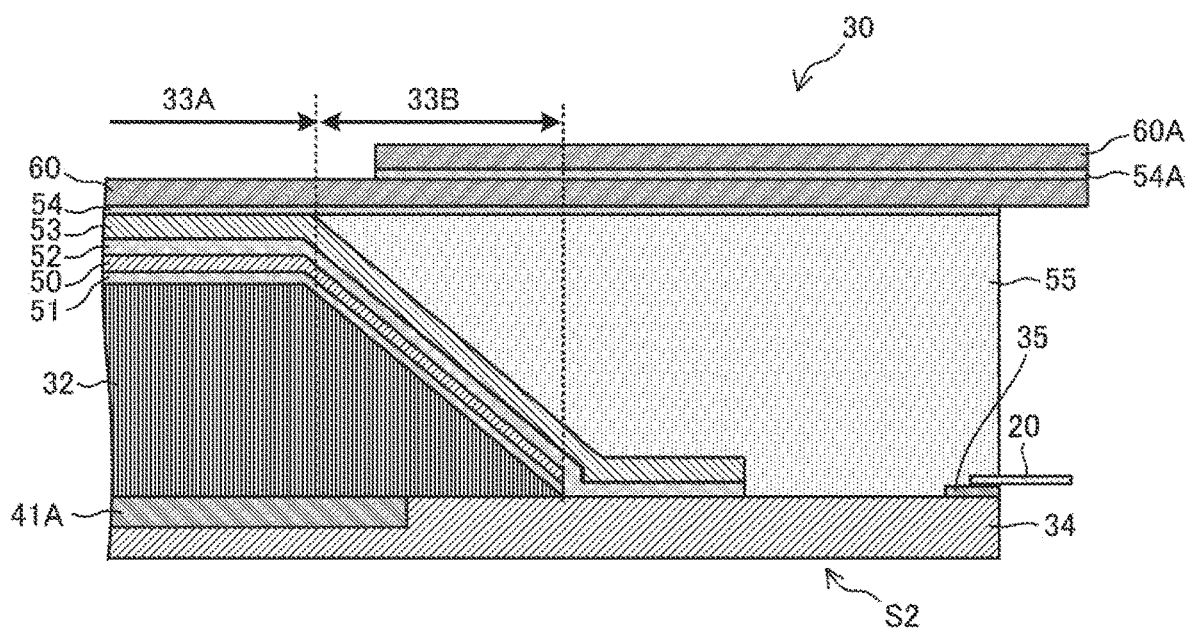
FIG. 33 is a cross-section illustrating an example of a configuration of a radiation detector according to an exemplary embodiment of technology disclosed herein.

In the example illustrated in FIG. 33, the filler 55 is filled into the space formed between the scintillator 32 (the protective layer 53) and the bending suppression member 60 and between the substrate 34 and the bending suppression member 60. Moreover, an additional and separate bending suppression member 60A is stacked on a front surface of the bending suppression member 60 at a region corresponding to the end portion of the scintillator 32, with a bonding layer 54A interposed therebetween. More specifically, the bending suppression member 60A is provided in a region straddling the end portion (outer edge, edge) of the scintillator 32. The bending suppression member 60A may be configured from the same materials as the bending suppression member 60. As illustrated in FIG. 9, the amount of bending of the substrate 34 is comparatively large at the end portions of the scintillator 32. Forming a multi-layer structure using the bending suppression members 60 and 60A at the region corresponding to the end portion of the scintillator 32 enables the effect of suppressing bending of the substrate 34 to be enhanced at the end portion of the scintillator 32.

In processes to manufacture the radiation detector 30, the flexible substrate 34 is stuck to a support body, such as a glass substrate or the like, and then after stacking the scintillator 32 onto the substrate 34, the support body is detached from the substrate 34. When this is performed bending occurs in the flexible substrate 34, and there is a concern that the pixels 41 formed on the substrate 34 might be damaged thereby. By stacking the bending suppression member 60 on the scintillator 32 as in the embodiments illustrated in the examples of FIG. 13 to FIG. 33 prior to detaching the support body from the substrate 34, the bending of the substrate 34 that occurs when the support body is being detached from the substrate 34 can be suppressed, enabling the risk of damage of the pixels 41 to be reduced.

FIG. 34 to FIG. 39 are cross-sections illustrating examples of installation embodiments of bending suppression members in cases in which bending suppression members are provided on the second surface S2 side of the substrate 34, this being the opposite side to the first surface S1 that contacts the scintillator 32.

In each of the examples of FIG. 34 to FIG. 39, substantially the entire second surface S2 of the substrate 34 is in contact with the bending suppression member 60 through the bonding layer 54. Namely, the surface area of the bending suppression member 60 is substantially the same as the surface area of the substrate 34. An additional and separate bending suppression member 60A is stacked on the face of the bending suppression member 60 that is on the opposite side to the face on the substrate 34 side of the bending suppression member 60, with a bonding layer 54A interposed therebetween. The bending suppression member 60A may be configured from the same materials as the bending suppression member 60. In cases in which an irradiation side sampling (ISS) approach is adopted as the imaging method of the radiation detector 30, the bending suppression member 60A is preferably provided only on the outer peripheral portion of the substrate 34 in order to keep the surface area of the overlapping portion between the bending suppression member 60A and the pixel region 41A as small as possible. Namely, the bending suppression member 60A may have a ring shape including an opening 61 at a portion corresponding to the pixel region 41A, as illustrated in FIG. 34 to FIG. 39. Thus forming a multi-layer structure using the bending suppression members 60 and 60A at the outer peripheral portion of the substrate 34 enables the rigidity of the outer peripheral portion of the substrate 34 that is comparatively susceptible to bending to be reinforced.

Figure 34:
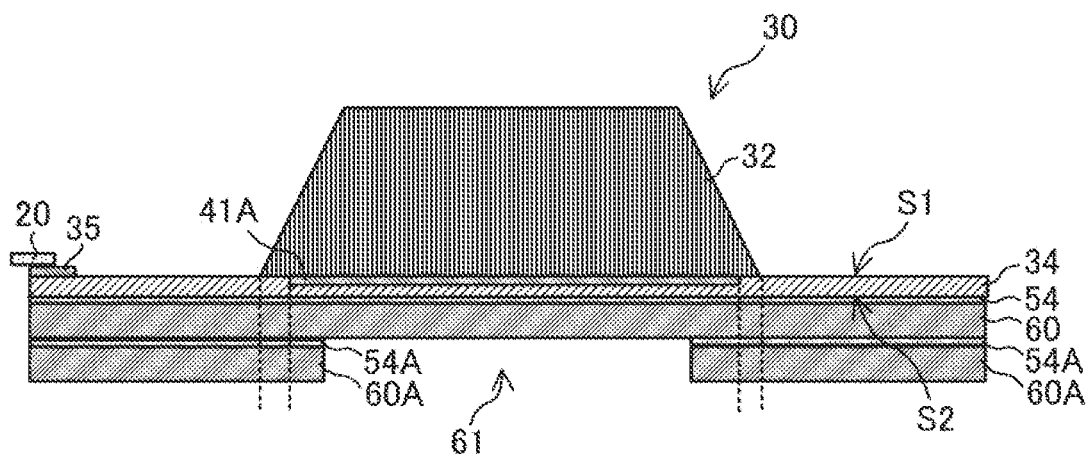
FIG. 34 is a cross-section illustrating an example of a configuration of a radiation detector according to an exemplary embodiment of technology disclosed herein.
Figure 35:
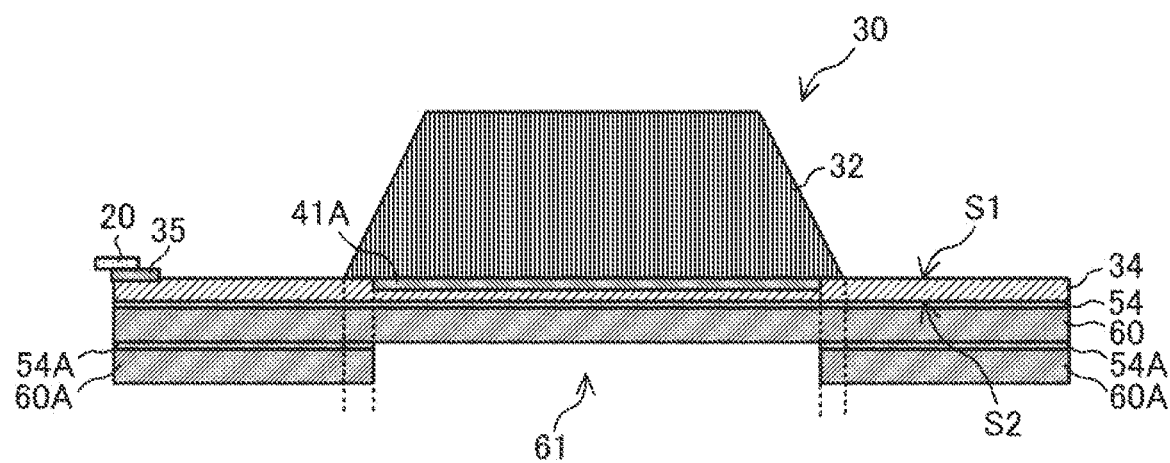
FIG. 35 is a cross-section illustrating an example of a configuration of a radiation detector according to an exemplary embodiment of technology disclosed herein.
Figure 36:
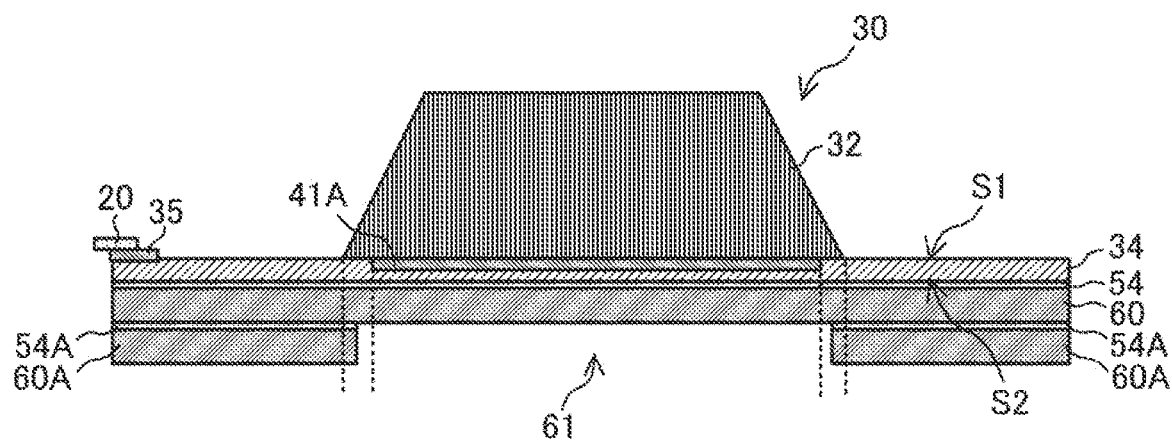
FIG. 36 is a cross-section illustrating an example of a configuration of a radiation detector according to an exemplary embodiment of technology disclosed herein.

In the examples illustrated in FIG. 34 to FIG. 36, the bending suppression member 60A is provided in a region straddling the end portion (outer edge, edge) of the scintillator 32. As illustrated in FIG. 9, the amount of bending of the substrate 34 is comparatively large at the end portions of the scintillator 32. Forming a multi-layer structure using the bending suppression members 60 and 60A at the region corresponding to the end portion of the scintillator 32 enables the effect of suppressing bending of the substrate 34 to be enhanced at the end portion of the scintillator 32.

In cases in which an irradiation side sampling (ISS) approach is adopted as the imaging method of the radiation detector 30, there is a concern that were a portion of the bending suppression member 60A to overlap with the pixel region 41A as illustrated in FIG. 34, depending on the substance employed in the bending suppression member 60A this might have an impact on the images. In cases in which a portion of the bending suppression member 60A overlaps with the pixel region 41A, a plastic is therefore preferably employed for the material of the bending suppression member 60A.

Most preferably an embodiment is adopted in which, as illustrated in FIG. 35 and FIG. 36, the bending suppression member 60A straddles the end portion (outer edge, edge) of the scintillator 32 but does not overlap with the pixel region 41A (namely, an embodiment in which an edge of the opening 61 of the bending suppression member 60A is disposed at the outside of the pixel region 41A). In the example illustrated in FIG. 35, the position of the edge of the opening 61 of the bending suppression member 60A is substantially aligned with the position of the end portion of the pixel region 41A. In the example illustrated in FIG. 36, the edge of the opening 61 of the bending suppression member 60A is disposed between the end portion of the pixel region 41A and the end portion of the scintillator 32.

Figure 37:
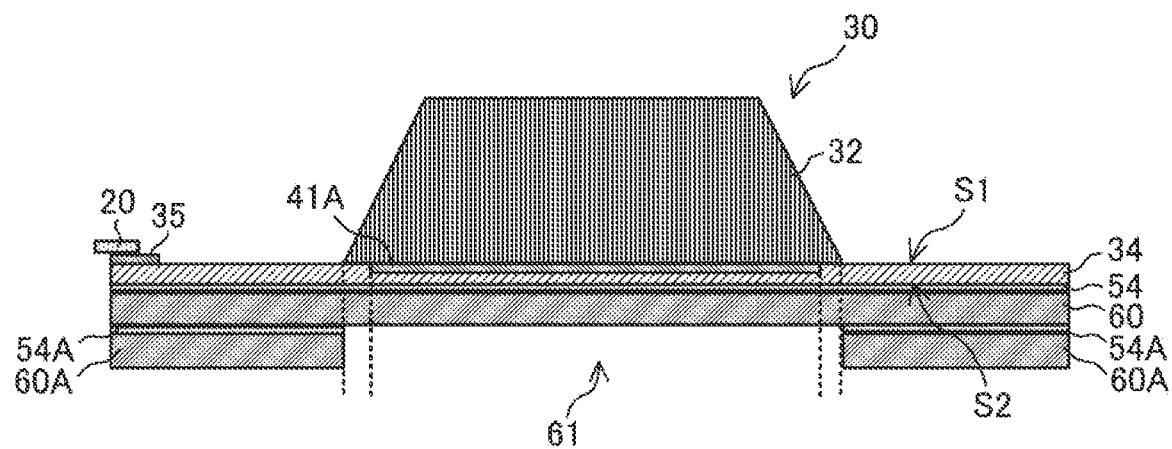
FIG. 37 is a cross-section illustrating an example of a configuration of a radiation detector according to an exemplary embodiment of technology disclosed herein.
Figure 38:
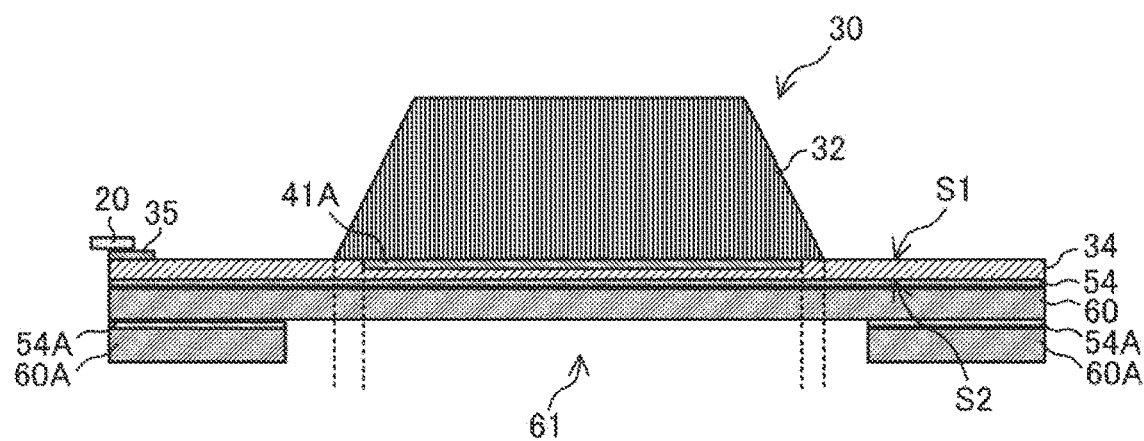
FIG. 38 is a cross-section illustrating an example of a configuration of a radiation detector according to an exemplary embodiment of technology disclosed herein.

Moreover, the position of the edge of the opening 61 of the bending suppression member 60A may be disposed so as to be substantially aligned with the position of the end portion of the scintillator 32 as illustrated in FIG. 37, or may be disposed so as to be further outside than the end portion of the scintillator 32 as illustrated in FIG. 38. In such cases there is no structure present where the bending suppression member 60A straddles the end portion (outer edge, edge) of the scintillator 32, and so there might be a concern regarding a lessening of the effect of suppressing bending of the substrate 34 at the end portion of the scintillator 32. However, due to forming a multi-layer structure using the bending suppression members 60 and 60A at the outer peripheral portion of the substrate 34 where the connection portions between the cable 20 and the terminals 35 are present, the effect of suppressing bending of the substrate 34 at the connection portions between the cable 20 and the terminals 35 is maintained.

Figure 39:
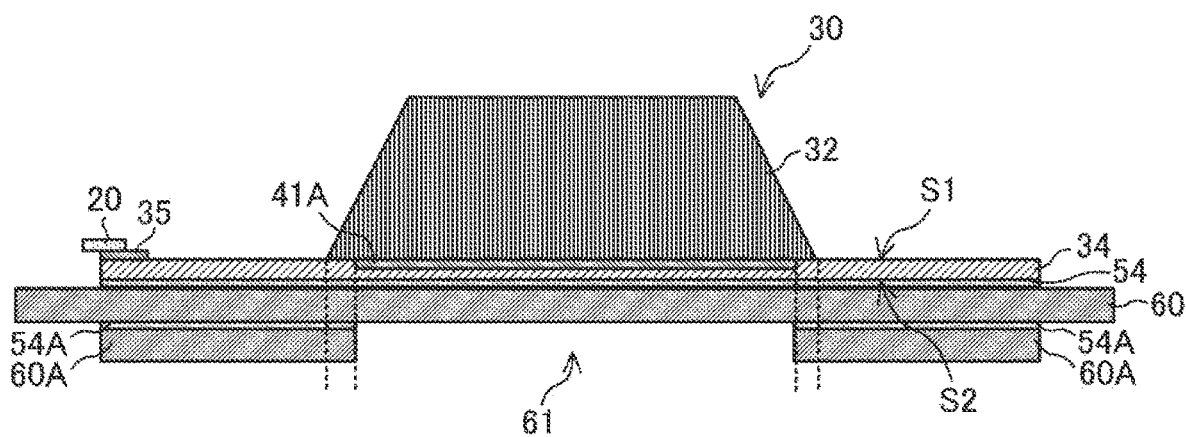
FIG. 39 is a cross-section illustrating an example of a configuration of a radiation detector according to an exemplary embodiment of technology disclosed herein.

In the example illustrated in FIG. 39, the surface area of the bending suppression member 60 is larger than the surface area of the substrate 34, and the end portion of the bending suppression member 60 is disposed further outside than the end portion of the substrate 34. Adopting such an embodiment enables the radiation detector 30 to be fixed to the inside of the case 14 by screwing a portion of the bending suppression member 60 that juts out from the substrate 34 to the case 14, or the like.

Note that although examples are illustrated in FIG. 34 to FIG. 39 of embodiments in which the position of the outside end portion of the bending suppression member 60A is substantially aligned with the position of the end portion of the substrate 34, there is no limitation to such embodiments. The outside end portion of the bending suppression member 60A may be disposed further to the outside or inside than the end portion of the substrate 34.

Although examples are illustrated in FIG. 34 to FIG. 39 of embodiments in which a multi-layer structure is formed using the bending suppression members 60 and 60A at the second surface S2 side of the substrate 34, there is no limitation to such embodiments. For example, in cases in which the bending suppression member 60 is provided at the scintillator 32 side as in the examples of embodiments illustrated in FIG. 13 to FIG. 33, the bending suppression member 60A may be provided alone at the second surface S2 side of the substrate 34 in order to reinforce the outer peripheral portion of the substrate 34.

Figure 40:
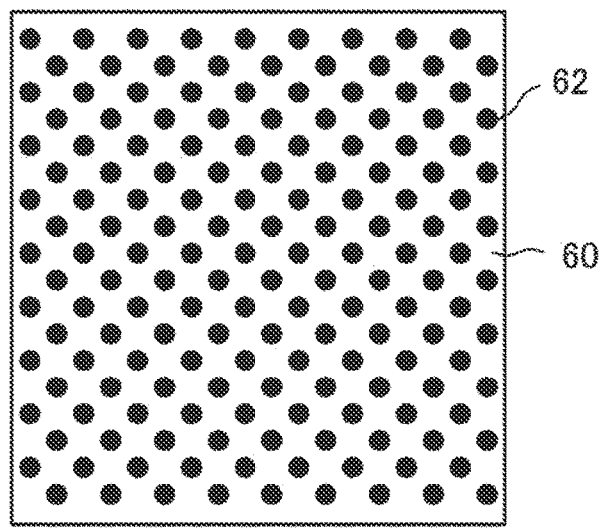
FIG. 40 is a plan view illustrating an example of a structure of a bending suppression member according to an exemplary embodiment of technology disclosed herein.

FIG. 40 is a plan view illustrating an example of a structure of the bending suppression member 60. A main face of the bending suppression member 60 may include plural through holes 62. The size and pitch of the through holes 62 is prescribed so as to obtain the desired rigidity of the bending suppression member 60.

Including the plural through holes 62 in the bending suppression member 60 enables air introduced at the joining face of the bending suppression member 60 to the scintillator 32 side or the substrate 34 side to escape through the through holes 62. This enables air bubbles to be suppressed from being generated at the joining face of the bending suppression member 60 to the scintillator 32 side or the substrate 34 side.

There is a concern that air bubbles might be generated at the joining face if no mechanism is provided to allow air introduced at the joining face of the bending suppression member 60 to the scintillator 32 side or the substrate 34 side to escape. For example, were air bubbles arising at the joining face to expand due to heat during operation of the radiographic imaging device 10, there would be a drop in the cohesion between the bending suppression member 60 and the scintillator 32 side or the substrate 34 side. This would lead to a concern that the bending suppression effect from the bending suppression member 60 might not be sufficiently exhibited. By using the bending suppression member 60 including the plural through holes 62 as illustrated in FIG. 40, the generation of air bubbles at the joining face of the bending suppression member 60 to the scintillator 32 side or the substrate 34 side can be suppressed as described above, enabling the cohesion between the bending suppression member 60 and the scintillator 32 side or the substrate 34 side to be maintained. This enables the bending suppression effect of the bending suppression member 60 to be maintained.

Figure 41:
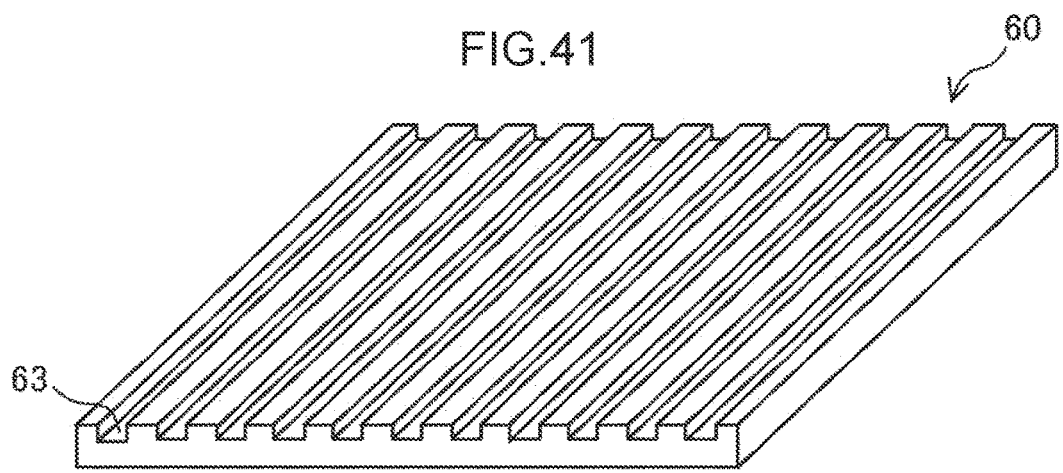
FIG. 41 is a perspective view illustrating an example of a structure of a bending suppression member according to an exemplary embodiment of technology disclosed herein.
Figure 42:
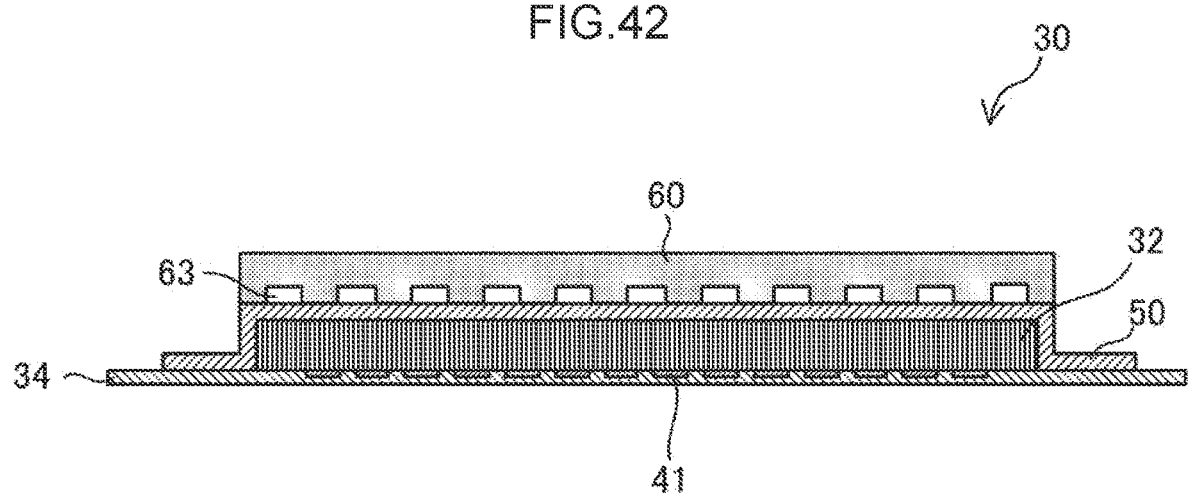
FIG. 42 is a cross-section illustrating an example of a configuration of a radiation detector according to an exemplary embodiment of technology disclosed herein.

FIG. 41 is a perspective view illustrating another example of the structure of the bending suppression member 60. In the example illustrated in FIG. 41, the bending suppression member 60 includes an indented and protruding structure on the joining face to the scintillator 32 side or the substrate 34 side. The indented and protruding structure may be configured including plural grooves 63 arranged parallel to each other, as illustrated in FIG. 41. The face of the bending suppression member 60 that includes the indented and protruding structure configured from the plural grooves 63 is, for example as illustrated in FIG. 42, joined to the scintillator 32 that has been covered by the reflective film 50. In this manner, due to the bending suppression member 60 including the indented and protruding structure on the joining face to the scintillator 32 side or the substrate 34 side, any air introduced to the joining portion of the bending suppression member 60 and the scintillator 32 side or the substrate 34 side is able to escape through the grooves 63. Similarly to in the embodiment illustrated in FIG. 40, this accordingly enables the generation of air bubbles at the joining face of the bending suppression member 60 to the scintillator 32 side or the substrate 34 side to be suppressed. This enables the cohesion between the bending suppression member 60 and the scintillator 32 side or the substrate 34 side to be maintained, and enables the bending suppression effect of the bending suppression member 60 to be maintained.

Figure 43:
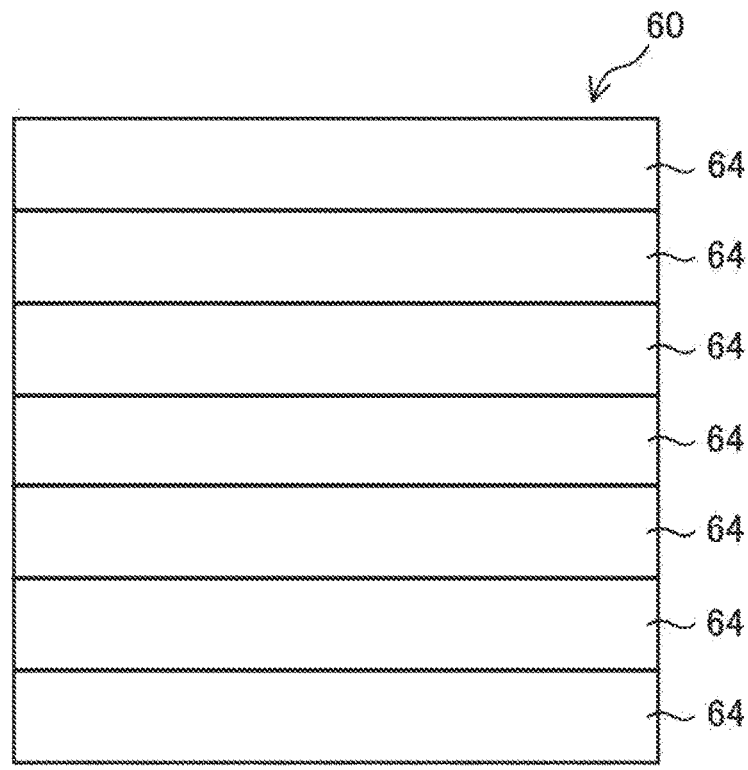
FIG. 43 is a plan view illustrating an example of a structure of a bending suppression member according to an exemplary embodiment of technology disclosed herein.
Figure 44:
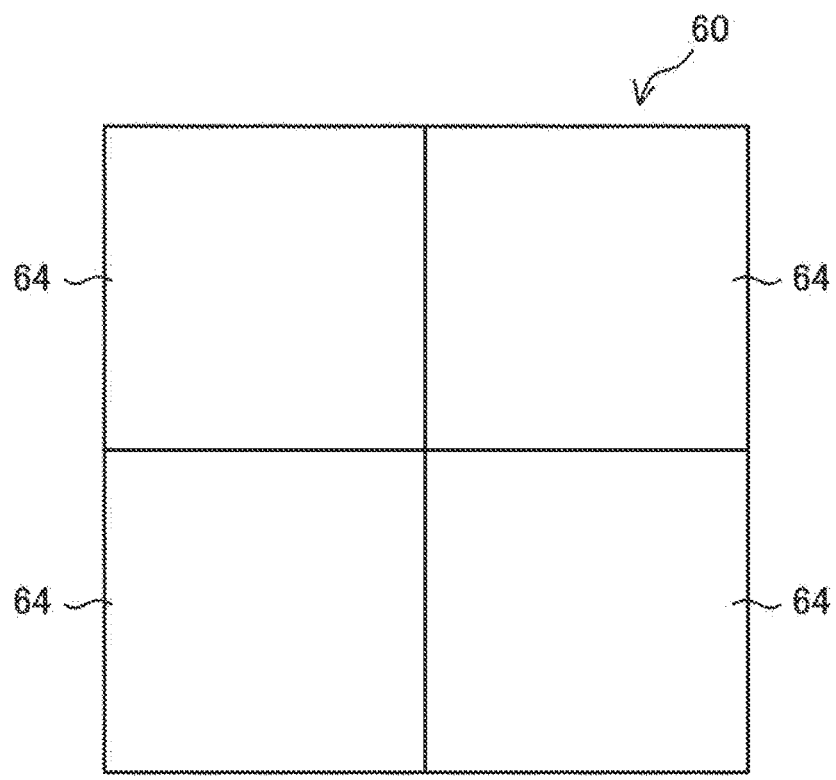
FIG. 44 is a plan view illustrating an example of a structure of a bending suppression member according to an exemplary embodiment of technology disclosed herein.

FIG. 43 and FIG. 44 are plan views illustrating other example of structures of the bending suppression member 60. As illustrated in FIG. 43 and FIG. 44, the bending suppression member 60 may be segmented into plural pieces 64. The bending suppression member 60 may, as illustrated in FIG. 43, be segmented into the plural pieces 64 arrayed along one direction. Moreover, the bending suppression member 60 may, as illustrated in FIG. 44, be segmented into the plural pieces 64 arrayed in both a longitudinal direction and a lateral direction.

The greater the surface area of the bending suppression member 60, the more readily air bubbles are generated at the joining face of the bending suppression member 60 to the scintillator 32 side or the substrate 34 side. As illustrated in FIG. 43 and FIG. 44, segmenting the bending suppression member 60 into the plural pieces 64 enables air bubbles to be suppressed from being generated at the joining face of the bending suppression member 60 to the scintillator 32 side or the substrate 34 side. This enables the cohesion between the bending suppression member 60 and the scintillator 32 side or the substrate 34 side to be maintained, and thereby enables the bending suppression effect of the bending suppression member 60 to be maintained.

Figure 45:
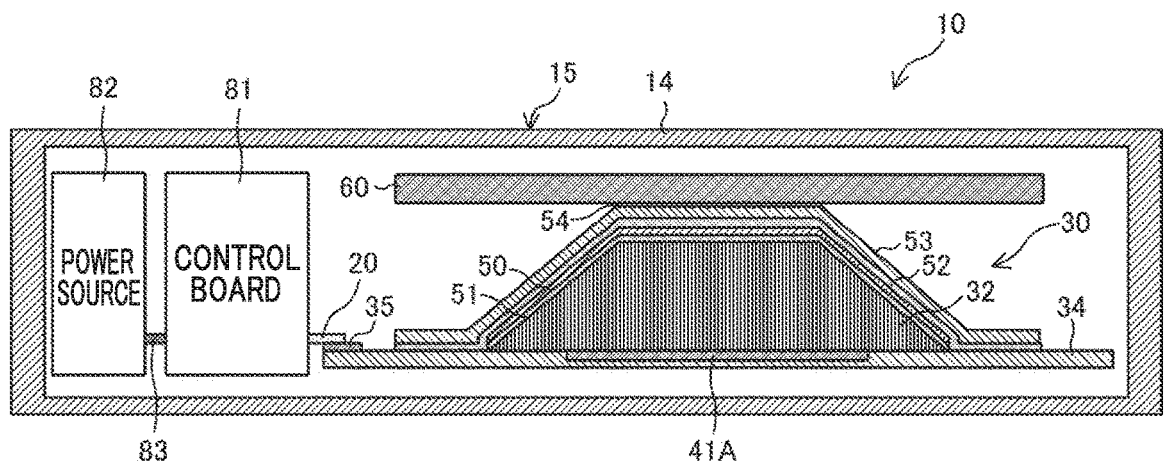
FIG. 45 is a cross-section illustrating an example of a configuration of a radiographic imaging device according to an exemplary embodiment of technology disclosed herein.
Figure 46:
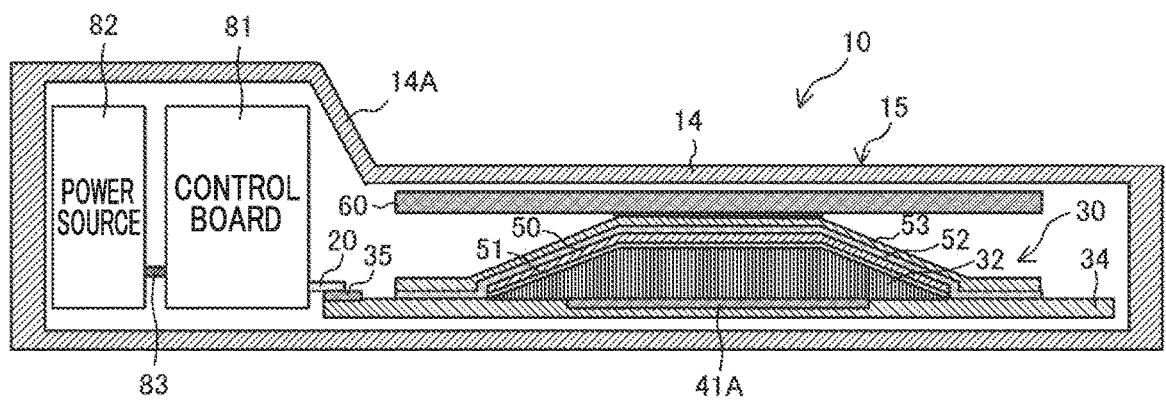
FIG. 46 is a cross-section illustrating an example of a configuration of a radiographic imaging device according to an exemplary embodiment of technology disclosed herein.
Figure 47:
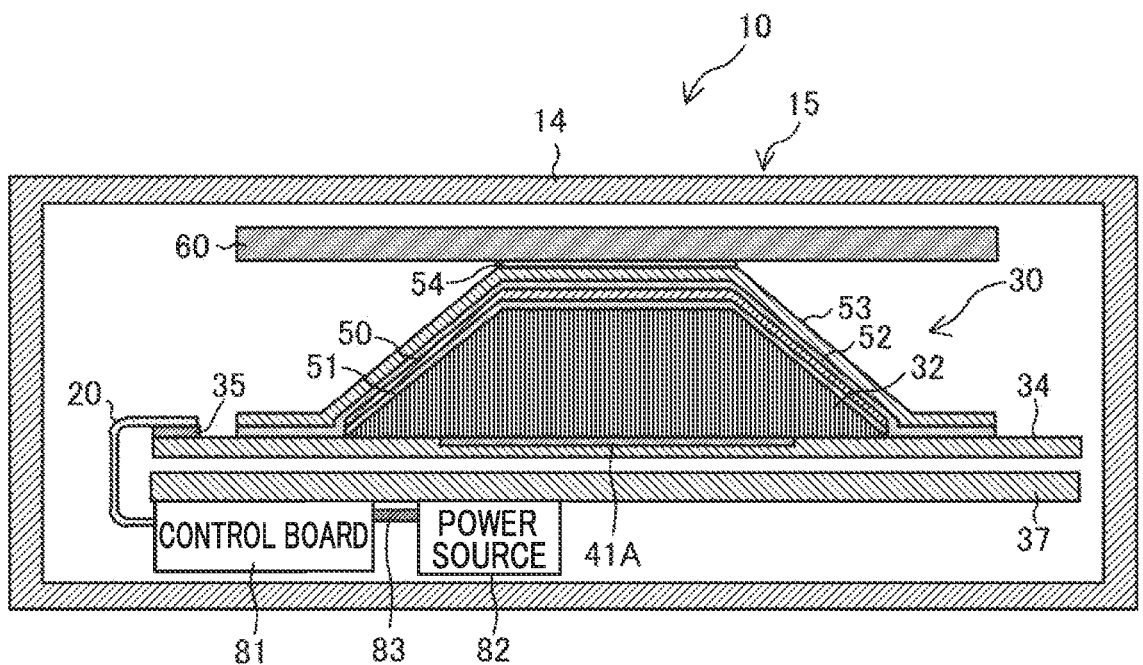
FIG. 47 is a cross-section illustrating an example of a configuration of a radiographic imaging device according to an exemplary embodiment of technology disclosed herein.

FIG. 45 to FIG. 47 are diagrams respectively illustrating other configuration examples of the radiographic imaging device 10. The radiographic imaging device 10 is configured including the case 14, the radiation detector 30 housed inside the case 14, and a control board 81 and a power source 82.

The control board 81 is aboard mounted with some or all of the electronic components configuring the controller 29, the image memory 28, the gate line driver 22, the charging amplifiers 24, and the signal processor 26 illustrated in FIG. 3. The control board 81 may be a rigid board having a higher rigidity than that of the flexible substrate 34. The power source 82 supplies power through power lines 83 to the electronic components mounted on the control board 81.

The case 14 is preferably lightweight, has a low absorption ratio to X-rays, and has high rigidity, and is preferably configured from a material that has an elastic modulus sufficiently higher than that of the bending suppression member 60. A material having a bending elastic modulus of at least 10000 MPa is preferably employed as the material of the case 14. Examples of materials suitably employed as the material of the case 14 include carbon or carbon fiber reinforced plastics (CFRP) having a bending elastic modulus of around 20,000 MPa to 60,000 MPa.

When radiographic images are imaged using the radiographic imaging device 10, load is applied to the radiation-incident face 15 of the case 14 by the imaging subject. In cases in which the bending suppression member 60 is, for example, configured from a material having a comparatively low elastic modulus, such as a soft plastic or the like, then there is a concern that were the rigidity of the case 14 to be insufficient, then bending might occur in the substrate 34 under the load from the imaging subject, resulting in problems such as damage to the pixels 41. By housing the radiation detector 30 equipped with the bending suppression member 60 inside the case 14 made from a material having a bending elastic modulus of not less than 10,000 MPa, bending of the substrate 34 under load from the imaging subject can be suppressed, even in cases in which the bending suppression member 60 is configured from a material having a comparatively low elastic modulus, such as a soft plastic or the like. By causing the bending suppression member 60 and an inner wall face of the case 14 to cohere, the effect of suppressing bending of the substrate 34 under the load from the imaging subject can be further enhanced. In such cases, the bending suppression member 60 and the inner wall face of the case 14 may be bonded through a bonding layer, or may simply be placed in contact with each other without interposing a bonding layer.

The examples illustrated in FIG. 45 and FIG. 46 are examples of configurations in which the radiation detector 30, the control board 81, and the power source 82 are arranged next to each other along a lateral direction in the drawings. As illustrated in FIG. 46, in the internal space of the case 14, the thickness of a region housing the radiation detector 30 may be made thinner than the thickness of a region housing the control board 81 and the power source 82. Adopting this approach enables configuration of an ultra-thin portable electronic cassette having a thickness appropriate to the thickness of the radiation detector 30. In order to soften a step formed between the region housing the radiation detector 30 and the region housing the control board 81 and the power source 82, the case 14 preferably includes a sloping portion 14A at a portion where these two regions are connected together. By including the sloping portion 14A in the case 14, any discomfort felt by a patient serving as the imaging subject can be reduced when the radiographic imaging device 10 is employed in a state inserted below the patient.

In the example illustrated in FIG. 47, a base 37 having substantially the same size as that of the substrate 34 of the radiation detector 30 is provided at a position overlapping with the substrate 34 within the internal space of the case 14, and the control board 81 and the power source 82 are provided on the base 37. Adopting such a configuration enables the size of the radiographic imaging device 10 in plan view to be decreased in comparison to cases in which the radiation detector 30, the control board 81, and the power source 82 are arranged next to each other along the lateral direction in the drawings.

The entire content of the disclosures of Japanese Patent Application Nos. 2018-051692, 2018-219698, and 2019-022082 are incorporated by reference in the present specification.

All publications, patent applications and technical standards mentioned in the present specification are incorporated by reference in the present specification to the same extent as if each individual publication, patent application, or technical standard was specifically and individually indicated to be incorporated by reference.

In a radiation detector according to a second aspect of technology disclosed herein, the scintillator is stacked on a first surface side of the substrate, and the bending suppression member is stacked on at least one side of a second surface side of the substrate that is on the opposite side to the first surface side, or a side corresponding to a surface of the scintillator on the opposite side to a surface of the scintillator contacting the substrate.

In a radiation detector according to a third aspect of technology disclosed herein, the bending suppression member is stacked on both the second surface side of the substrate and the side corresponding to the surface of the scintillator on the opposite side to the surface of the scintillator contacting the substrate.

In a radiation detector according to a fourth aspect of technology disclosed herein, the bending suppression member has a higher rigidity than the substrate.

In a radiation detector according to a fifth aspect of technology disclosed herein, the bending suppression member extends so as to span a wider range than an extension range of the scintillator.

In a radiation detector according to a sixth aspect of technology disclosed herein, the substrate includes a connection region for a flexible wiring connection, and the bending suppression member is provided in a region covering at least a portion of the connection region and also covering the scintillator.

In a radiation detector according to a seventh aspect of technology disclosed herein, the bending suppression member has a bending elastic modulus of from 1000 MPa to 3500 MPa.

In a radiation detector of according to an eighth aspect of technology disclosed herein, a ratio of a coefficient of thermal expansion of the bending suppression member against a coefficient of thermal expansion of the scintillator is from 0.5 to 2.

In a radiation detector according to a ninth aspect of technology disclosed herein, a coefficient of thermal expansion of the bending suppression member is from 30 ppm/K to 80 ppm/K.

In a radiation detector according to a tenth aspect of technology disclosed herein, the bending suppression member is configured including at least one out of acrylic, polycarbonate, or polyethylene terephthalate.

A radiation detector according to an eleventh aspect of technology disclosed herein further includes a reinforcement member that is provided in a region straddling an end portion of the scintillator so as to reinforce a bending suppression effect of the bending suppression member.

In a radiation detector according to a twelfth aspect of technology disclosed herein, the reinforcement member has a higher rigidity than the substrate.

In a radiation detector according to a thirteenth aspect of technology disclosed herein, the reinforcement member is configured from a material that is the same as a material of the bending suppression member.

In a radiation detector according to a fourteenth aspect of technology disclosed herein, the substrate is configured including a resin film.

In a radiation detector according to a fifteenth aspect of technology disclosed herein, the substrate is configured including a base member made from a resin material including a fine particle layer containing fine particles of an inorganic material having a mean particle size of from 0.05 μm to 2.5 μm. The fine particle layer is provided on a second surface side of the substrate that is on the opposite side to a first surface of the substrate provided with the plural pixels.

In a radiation detector according to a sixteenth aspect of technology disclosed herein, the fine particles include an element having an atomic number that is greater than an atomic number of elements configuring the resin material and that is an atomic number not exceeding 30.

In a radiation detector according to a seventeenth aspect of technology disclosed herein, the substrate has a coefficient of thermal expansion not greater than 20 ppm/K in a temperature range from 300° C. to 400° C.

In a radiation detector according to an eighteenth aspect of technology disclosed herein, the substrate satisfies at least one condition out of having a heat shrinkage ratio in a machine direction at 400° C. and at a substrate thickness of 25 μm of not greater than 0.5%, or having a modulus of elasticity at 500° C. of not less than 1 GPa.

A radiation detector according to a nineteenth aspect of technology disclosed herein further includes a buffer layer that is provided between the substrate and the scintillator and that has a coefficient of thermal expansion lying between the coefficient of thermal expansion of the substrate and the coefficient of thermal expansion of the scintillator.

In a radiation detector according to a twentieth aspect of technology disclosed herein, the scintillator includes a non-columnar portion on one end side of the columnar crystals, and the non-columnar portion is in contact with the substrate.

A radiographic imaging device according to a twenty-first aspect of technology disclosed herein includes the radiation detector of any one of the first to twentieth aspects, a reading section configured to perform reading of electrical charge accumulated in the pixels, and a generation section configured to generate image data based on the electrical charge read from the pixels.

A radiographic imaging device according to a twenty-second aspect of technology disclosed herein further includes a case that houses the radiation detector and that includes a radiation-incident face to which radiation is incident, and out of the substrate and the scintillator, the substrate is disposed on a side corresponding to the radiation-incident face.

A radiation detector manufacturing method according to a twenty-third aspect of technology disclosed herein includes a process of forming plural pixels on a flexible substrate such that each pixel includes a photoelectric conversion element, a process of forming a scintillator including plural columnar crystals on the substrate, and a process of arranging a bending suppression member configured to suppress bending of the substrate. Rigidity of the bending suppression member is adjusted according to a height of the columnar crystals, a radius of the columnar crystals, a tip angle of the columnar crystals, and an interval between the columnar crystals.

In a manufacturing method according to a twenty-fourth aspect of technology disclosed herein, the bending suppression member has a rigidity satisfying $R \geq L - r/\tan(+4r \times \{(L-r/\tan \Phi^2 - (d/2)^2\}^{1/2}/d$, wherein L is an average height of the columnar crystals, r is an average radius of the columnar crystals, d is an average interval between the columnar crystals, $\Phi$ is an average tip angle of the columnar crystals, and R is a radius of curvature of bending of the substrate due to the weight of the scintillator.

In a manufacturing method according to a twenty-fifth aspect of technology disclosed herein, the process of forming the scintillator includes a process of growing the columnar crystals on a front surface of the substrate using a vapor phase epitaxial method.

Advantageous Effects of Invention

The first aspect of technology disclosed herein enables the risk of damage to the scintillator caused by bending occurring in the substrate due to the weight of the scintillator to be reduced in comparison to cases lacking a bending suppression member having a rigidity prescribed according to the height, radius, and tip angle of the columnar crystals as well as the interval between the columnar crystals.

The second aspect of technology disclosed herein enables a bending suppression effect to be effectively exhibited by the bending suppression member.

The third aspect of technology disclosed herein enables the risk of damage to the scintillator caused by bending of the substrate to be further reduced.

The fourth aspect of technology disclosed herein enables a bending suppression effect to be effectively exhibited by the bending suppression member.

The fifth aspect of technology disclosed herein enables a bending suppression effect to be effectively exhibited by the bending suppression member.

The sixth aspect of technology disclosed herein enables a bending suppression effect to be effectively exhibited by the bending suppression member.

The seventh aspect of technology disclosed herein enables a preferable rigidity to be achieved for the bending suppression member.

The eighth aspect of technology disclosed herein enables the risk of the substrate and the scintillator detaching from one another to be suppressed in comparison to cases in which the ratio of the coefficient of thermal expansion of the bending suppression member against the coefficient of thermal expansion of the scintillator does not lie in the stated range.

The ninth aspect of technology disclosed herein enables the risk of the substrate and the scintillator detaching from one another to be suppressed in comparison to cases in which the coefficient of thermal expansion of the bending suppression member does not lie in the stated range.

The tenth aspect of technology disclosed herein enables a bending suppression effect to be more effectively exhibited by the bending suppression member, and the risk of the substrate and the scintillator detaching from one another to be suppressed, in comparison to cases in which a configuration is adopted in which the bending suppression member is configured including another material.

The eleventh aspect of the technology disclosed herein enables bending of a portion of the substrate corresponding to the end portion of the scintillator to be suppressed in comparison to cases in which no reinforcement member is provided.

In the twelfth aspect of technology disclosed herein, an effect of reinforcing the bending suppression effect of the bending suppression member is effectively exhibited.

In the thirteenth aspect of technology disclosed herein, an effect of reinforcing the bending suppression effect of the bending suppression member is effectively exhibited.

The fourteenth aspect of technology disclosed herein enables a more lightweight and lower cost radiation detector to be achieved compared with cases in which a glass substrate is employed as the material for the substrate, and moreover enables the risk of impact damage to the substrate to be reduced.

The fifteenth aspect of technology disclosed herein enables back scattering radiation to be suppressed from being generated in the substrate in comparison to cases in which the substrate does not include a fine particle layer.

The sixteenth aspect of technology disclosed herein enables effective suppression of back scattering radiation while also enabling absorption of radiation in the fine particle layer to be suppressed in comparison to cases in which the atomic number of the fine particles is not within the stated range.

The seventeenth aspect of technology disclosed herein enables more appropriate pixel formation on the substrate than in cases in which the coefficient of thermal expansion of the substrate is not within the stated range.

The eighteenth aspect of technology disclosed herein enables more appropriate pixel formation on the substrate than in cases in which the heat shrinkage ratio and modulus of elasticity of the substrate are not within the stated ranges.

The nineteenth aspect of technology disclosed herein enables thermal stress to be suppressed from acting at the interface between the substrate and the scintillator in comparison to cases in which a buffer layer is not included.

In the twentieth aspect of technology disclosed herein, the non-columnar portion of the scintillator contacts the substrate, and the tips of the columnar crystals are on the front surface side of the scintillator. The technology disclosed herein is thus particularly effective in cases in which the tips of the columnar crystals are on the front surface side of the scintillator.

The twenty-first aspect of technology disclosed herein enables the risk of damage to the scintillator caused by bending occurring in the substrate due to the weight of the scintillator to be reduced in comparison to cases lacking a bending suppression member having a rigidity prescribed according to the height, radius, and tip angle of the columnar crystals as well as the interval between the columnar crystals.

The twenty-second aspect of technology disclosed herein enables a higher resolution of radiographic images to be achieved than in cases in which, from out of the substrate and the scintillator, the scintillator is disposed on the side of the radiation-incident face.

The twenty-third aspect of technology disclosed herein enables the risk of damage to the scintillator caused by bending occurring in the substrate due to the weight of the scintillator to be reduced in comparison to cases lacking a bending suppression member where the rigidity of the bending suppression member is a rigidity prescribed according to the height, radius, and tip angle of the columnar crystals as well as the interval between the columnar crystals.

The twenty-fourth aspect of technology disclosed herein enables a reduction in the risk of damage to the scintillator caused by bending occurring in the substrate due to the weight of the scintillator to be secured.

The twenty-fifth aspect of technology disclosed herein enables stable formation of the columnar crystals.

What is claimed is:

1. A radiation detector comprising:
   a flexible substrate;
   a plurality of pixels provided on the substrate and each including a photoelectric conversion element;
   a scintillator stacked on the substrate and including a plurality of columnar crystals; and
   a bending suppression member configured to suppress bending of the substrate;
   the bending suppression member having a rigidity that satisfies $R \geq L - r/\tan \Phi + 4r \times \{(L - r/\tan \Phi)^2 - (d/2)^2\}^{1/2}/d$ wherein L is an average height of the columnar crystals, r is an average radius of the columnar crystals, d is an average interval between the columnar crystals, $\Phi$ is an average tip angle of the columnar crystals, and R is a radius of curvature of bending occurring in the substrate due to the weight of the scintillator.

2. The radiation detector of claim 1, wherein:
   the scintillator is stacked on a first surface side of the substrate; and
   the bending suppression member is stacked on at least one side of a second surface side of the substrate that is on the opposite side to the first surface side, or a side corresponding to a surface of the scintillator on the opposite side to a surface of the scintillator contacting the substrate.

3. The radiation detector of claim 2, wherein the bending suppression member is stacked on both the second surface side of the substrate and the side corresponding to the surface of the scintillator on the opposite side to the surface of the scintillator contacting the substrate.

4. The radiation detector of claim 1, wherein the bending suppression member has a higher rigidity than the substrate.

5. The radiation detector of claim 1, wherein the bending suppression member extends so as to span a wider range than an extension range of the scintillator.

6. The radiation detector of claim 1, wherein:
   the substrate includes a connection region for a flexible wiring connection; and
   the bending suppression member is provided in a region covering at least a portion of the connection region and also covering the scintillator.

7. The radiation detector of claim 1, wherein the bending suppression member has a bending elastic modulus of from 1000 MPa to 3500 MPa.

8. The radiation detector of claim 1, wherein a ratio of a coefficient of thermal expansion of the bending suppression member against a coefficient of thermal expansion of the scintillator is from 0.5 to 2.

9. The radiation detector of claim 1, wherein a coefficient of thermal expansion of the bending suppression member is from 30 ppm/K to 80 ppm/K.

10. The radiation detector of claim 1, wherein the bending suppression member is configured including at least one out of acrylic, polycarbonate, or polyethylene terephthalate.

11. The radiation detector of claim 1, further comprising a reinforcement member that is provided in a region straddling an end portion of the scintillator so as to reinforce a bending suppression effect of the bending suppression member.

12. The radiation detector of claim 11, wherein the reinforcement member has a higher rigidity than the substrate.

13. The radiation detector of claim 1, wherein the substrate is configured including a resin film.

14. The radiation detector of claim 1, wherein the substrate has a coefficient of thermal expansion not greater than 20 ppm/K in a temperature range from 300° C. to 400° C.

15. The radiation detector of claim 1, further comprising a buffer layer that is provided between the substrate and the scintillator and that has a coefficient of thermal expansion lying between the coefficient of thermal expansion of the substrate and the coefficient of thermal expansion of the scintillator.

16. The radiation detector of claim 1, wherein:
    the scintillator includes a non-columnar portion on one end side of the columnar crystals; and
    the non-columnar portion is in contact with the substrate.

17. A radiographic imaging device comprising:
    the radiation detector of claim 1;
    a reading circuit configured to perform reading of electrical charge accumulated in the pixels; and
    a signal processor configured to generate image data based on the electrical charge read from the pixels.

18. The radiographic imaging device of claim 17, further comprising:
    a case that houses the radiation detector and that includes a radiation-incident face to which radiation is incident; and
    out of the substrate and the scintillator, the substrate is disposed on a side corresponding to the radiation-incident face.

19. A manufacturing method for a radiation detector comprising:
    forming a plurality of pixels on a flexible substrate such that each pixel includes a photoelectric conversion element;
    forming a scintillator including a plurality of columnar crystals on the substrate; and
    arranging a bending suppression member configured to suppress bending of the substrate;
    rigidity of the bending suppression member being adjusted according to a height of the columnar crystals, a radius of the columnar crystals, a tip angle of the columnar crystals, and an interval between the columnar crystals.

20. The manufacturing method of claim 19, wherein the bending suppression member has a rigidity satisfying $R \geq L - r/\tan \Phi + 4r \times \{(L - r/\tan \Phi)^2 - (d/2)^2\}^{1/2}/d$ wherein L is an average height of the columnar crystals, r is an average radius of the columnar crystals, d is an average interval between the columnar crystals, $\Phi$ is an average tip angle of the columnar crystals, and R is a radius of curvature of bending of the substrate due to the weight of the scintillator.

* * * * *